(12) United States Patent
Felix et al.

(10) Patent No.: US 8,016,862 B2
(45) Date of Patent: Sep. 13, 2011

(54) SPINAL STABILIZING SYSTEM

(75) Inventors: Brent A. Felix, Sandy, UT (US);
Brandon Timothy Walker, Layton, UT (US); Ronald Kenneth Groberg, Clearfield, UT (US)

(73) Assignee: Innovasis, Inc., Salt Lake City, UT (US)

( * ) Notice: Subject to any disclaimer, the term of this patent is extended or adjusted under 35 U.S.C. 154(b) by 465 days.

(21) Appl. No.: 11/863,133

(22) Filed: Sep. 27, 2007

(65) Prior Publication Data
US 2008/0243185 A1    Oct. 2, 2008

Related U.S. Application Data

(60) Provisional application No. 60/847,996, filed on Sep. 27, 2006.

(51) Int. Cl.
*A61B 17/70* (2006.01)
(52) U.S. Cl. ........ 606/270; 606/266; 606/268; 606/273; 606/306
(58) Field of Classification Search .............. 606/60, 606/246, 250–279, 300–331; 215/346, 341, 215/283, 280, 276, 274, 273, 360; 220/293, 220/324, 325, 315, 328, 327, 297
See application file for complete search history.

(56) References Cited

U.S. PATENT DOCUMENTS

| | | | |
|---|---|---|---|
| 4,753,189 A * | 6/1988 | Mastman et al. | 116/308 |
| 5,449,078 A * | 9/1995 | Akers | 215/222 |
| 5,466,237 A | 11/1995 | Byrd, III et al. | |
| 5,474,555 A | 12/1995 | Puno et al. | |
| 5,934,492 A * | 8/1999 | Jones | 215/222 |
| 6,063,090 A | 5/2000 | Schlapfer | |
| 6,077,262 A * | 6/2000 | Schlapfer et al. | 606/305 |
| 6,248,105 B1 | 6/2001 | Schlapfer et al. | |
| 6,280,442 B1 | 8/2001 | Barker et al. | |
| 6,371,957 B1 | 4/2002 | Amrein et al. | |
| 6,471,705 B1 | 10/2002 | Biedermann et al. | |
| 6,478,797 B1 * | 11/2002 | Paul | 606/305 |
| 6,540,749 B2 * | 4/2003 | Schafer et al. | 606/270 |
| 6,565,567 B1 | 5/2003 | Haider | |
| 6,585,737 B1 * | 7/2003 | Baccelli et al. | 606/278 |
| 6,641,586 B2 | 11/2003 | Varieur | |
| 6,660,004 B2 | 12/2003 | Barker et al. | |

(Continued)

OTHER PUBLICATIONS

*VLS System Variable Locking Screw*, Interpore Cross International, 2001.

(Continued)

Primary Examiner — Eduardo C Robert
Assistant Examiner — Jerry Cumberledge
(74) Attorney, Agent, or Firm — Workman Nydegger

(57) ABSTRACT

A bone stabilizing system includes a collar that has a tubular sidewall with an interior surface and an exterior surface each extending between a first end and an opposing second end, the interior surface at least partially bounding a longitudinal passage extending therethrough. The collar also includes a pair of opposing spaced apart channels transversely extending through the sidewall at the first end thereof and a pair of spaced apart bayonet prongs projecting from the first end of the tubular sidewall. A screw has a threaded portion and a head disposed on an end thereof, the head of the screw being disposed within the longitudinal passage of the collar. A locking cap has a hole extending therethrough and a pair of spaced apart bayonet slots formed thereon, the bayonet slots being configured to receive and engage with the pair of bayonet prongs.

23 Claims, 38 Drawing Sheets

U.S. PATENT DOCUMENTS

| | | |
|---|---|---|
| 6,740,086 B2 | 5/2004 | Richelsoph |
| 7,081,116 B1* | 7/2006 | Carly .................... 606/264 |
| 2002/0010467 A1* | 1/2002 | Cooper et al. ............ 606/61 |
| 2002/0116001 A1* | 8/2002 | Schafer et al. ........... 606/61 |
| 2003/0004511 A1* | 1/2003 | Ferree .................... 606/61 |
| 2003/0075519 A1* | 4/2003 | Miceli et al. ............ 215/228 |
| 2003/0187434 A1* | 10/2003 | Lin ....................... 606/61 |
| 2004/0030337 A1* | 2/2004 | Alleyne et al. .......... 606/61 |
| 2004/0097926 A1* | 5/2004 | Kim ....................... 606/61 |
| 2004/0097933 A1* | 5/2004 | Lourdel et al. .......... 606/61 |
| 2004/0116929 A1* | 6/2004 | Barker et al. ............ 606/61 |
| 2004/0158247 A1* | 8/2004 | Sitiso et al. ............ 606/61 |
| 2004/0267264 A1* | 12/2004 | Konieczynski et al. ... 606/73 |
| 2005/0056314 A1* | 3/2005 | Lin ....................... 137/223 |
| 2005/0072124 A1* | 4/2005 | Jaycox ................... 53/490 |
| 2005/0145629 A1* | 7/2005 | Herr ...................... 220/293 |
| 2005/0171542 A1* | 8/2005 | Biedermann et al. ..... 606/61 |
| 2005/0177154 A1* | 8/2005 | Moumene et al. ........ 606/61 |
| 2005/0187548 A1* | 8/2005 | Butler et al. ............ 606/61 |
| 2005/0199572 A1* | 9/2005 | Brozell .................. 215/218 |
| 2005/0252877 A1* | 11/2005 | Moller ................... 215/222 |
| 2006/0025767 A1* | 2/2006 | Khalili ................... 606/61 |
| 2006/0085072 A1 | 4/2006 | Funk et al. |
| 2006/0161152 A1* | 7/2006 | Ensign et al. ........... 606/61 |
| 2006/0161153 A1* | 7/2006 | Hawkes et al. .......... 606/61 |
| 2006/0173456 A1* | 8/2006 | Hawkes et al. .......... 606/61 |
| 2006/0264933 A1* | 11/2006 | Baker et al. ............ 606/61 |
| 2006/0289377 A1* | 12/2006 | Miceli et al. ............ 215/332 |

OTHER PUBLICATIONS

EBI Spine Systems, *EBI Ωmega2l Spinal Fixation System, Surgical Technique*, published at least as early as Sep. 1, 2006.

*Click'X Top Loading System, Technique Guide*, Synthes Spine 2003.

*Synergy IQ, Low Back Surgical Technique*, Interpore Cross International, 2003.

* cited by examiner

SPINAL STABILIZING SYSTEM

CROSS-REFERENCE TO RELATED APPLICATIONS

The present application claims priority to U.S. Provisional Application No. 60/847,996, filed Sep. 27, 2006, which application is incorporated herein by specific reference.

BACKGROUND OF THE INVENTION

1. The Field of the Invention

The present invention relates to systems and methods for stabilizing a portion of a spine. More specifically, the invention relates to anchors and related components that are selectively mounted on a spine for stabilizing the spine.

2. The Relevant Technology

There are many surgical procedures and treatments that require the immobilization of a portion of the spine. For example, vertebral fusion is a medical procedure where adjacent vertebrae of the spine are fused together. As part of this procedure, a mechanical stabilizing system is implanted in the patient which immobilizes the adjacent vertebrae. Such stabilizing systems can also be used in the treatment of spinal trauma and spinal curvature such as scoliosis.

A typical spinal stabilizing system includes, in part, a pair of anchors and a rigid rod that extends between the anchors. The anchors are fixed to the adjacent vertebrae such that when the rod is connected to the anchors, the adjacent vertebrae become immobilized. A typical anchor includes a cylindrical tubular body having a longitudinal passage extending therethrough and a transverse passage extending therethrough. The exterior surface of the tubular body is round and has threads thereon to receive a nut.

The anchor also includes an elongated screw having an enlarged head formed on one end thereof. The head has a polygonal socket formed thereon in alignment with the longitudinal axis of the screw. The enlarged head of the screw is seated within the tubular body such that the tubular body can freely rotate and pivot relative to the screw. Once the screws are screwed into the corresponding vertebrae, the rod is positioned within the transverse passage of each tubular body. A nut is then screwed onto the exterior of the tubular body. The nut biases the rod against the head of the screw so as to rigidly secure the rod to the anchor.

Although spinal stabilizing systems are commonly used, conventional systems have a number of shortcomings. For example, mounting of the screw into the bone requires a thin elongated driver that mates with the polygonal socket on the head of the screw. Conventional drivers can be difficult and awkward to use resulting in misalignment of the screws. Furthermore, on occasion it is necessary to remove a screw after it has been implanted for an extended period of time. While the screw is implanted, however, tissue and/or bone typically grow over the head of the screw, thereby making it difficult to access the screw and couple the driver with the screw.

In addition, because the socket is formed on the top of the head of the screw, the top surface of the head is flat. During use, the rod rests on top of the head of the screw. However, the tubular body is often pivoted relative to the longitudinal axis of the screw so that the rod can be received within the transverse passage. As a result of the tubular body being pivoted, the rod often rests irregularly on the corner of the flat surface formed on the head of the screw. This irregular seating of the rod on the head of the screw can produce a weak connection, produce undesired pivoting of the screw or tubular body, and/or produce unwanted stress on the spine.

Furthermore, as the nut is tightened on the tubular body, the remainder of the anchor needs to be stabilized so that undue loads are not applied to the spine. To accomplish this, an anti-torque device is passed over the tubular body so as to engage only the rod passing therethrough. An opposing force is then applied by the anti-torque device to the rod as the nut is tightened onto the tubular body, thereby minimizing undue stress on the spine. One difficulty with this approach, however, is that the rod is often disposed directly on or adjacent to the bone and/or tissue. As such, it is often difficult and time consuming to adequately place the anti-torque device over the rod.

As mentioned above, a nut is screwed onto the exterior of the tubular body to bias the rod against the head of the screw so as to rigidly secure the rod to the anchor. This also simultaneously secures the tubular body to the screw. In other words, the collar is not secured to the screw until the rod is biased against the head of the screw, and in fact can rotate or pivot with respect to the screw. This points out another shortcoming with current systems. There are times a doctor wants to first secure the tubular body to the screw to form a rigid anchor, and then adjust the resulting rigid anchor with respect to the rod before the anchor is secured to the rod. For example, a doctor may desire to further separate or bring together vertebrae that have been crushed or otherwise affected. In most conventional systems this is not possible because, as pointed out above, the tubular body is not secured to the screw until the rod is secured using the nut. To solve this problem, included in some conventional systems is a separate set screw that allows the doctor to secure the tubular body to the screw independent of the rod being secured to the screw. While this helps solve the problem, having two screws instead of one makes the system more complex and exacerbates the problems mentioned above relating to drivers and unwanted torque being applied to the spine.

Accordingly, it would be beneficial to have spinal stabilizing systems that address some or all of the foregoing shortcomings.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
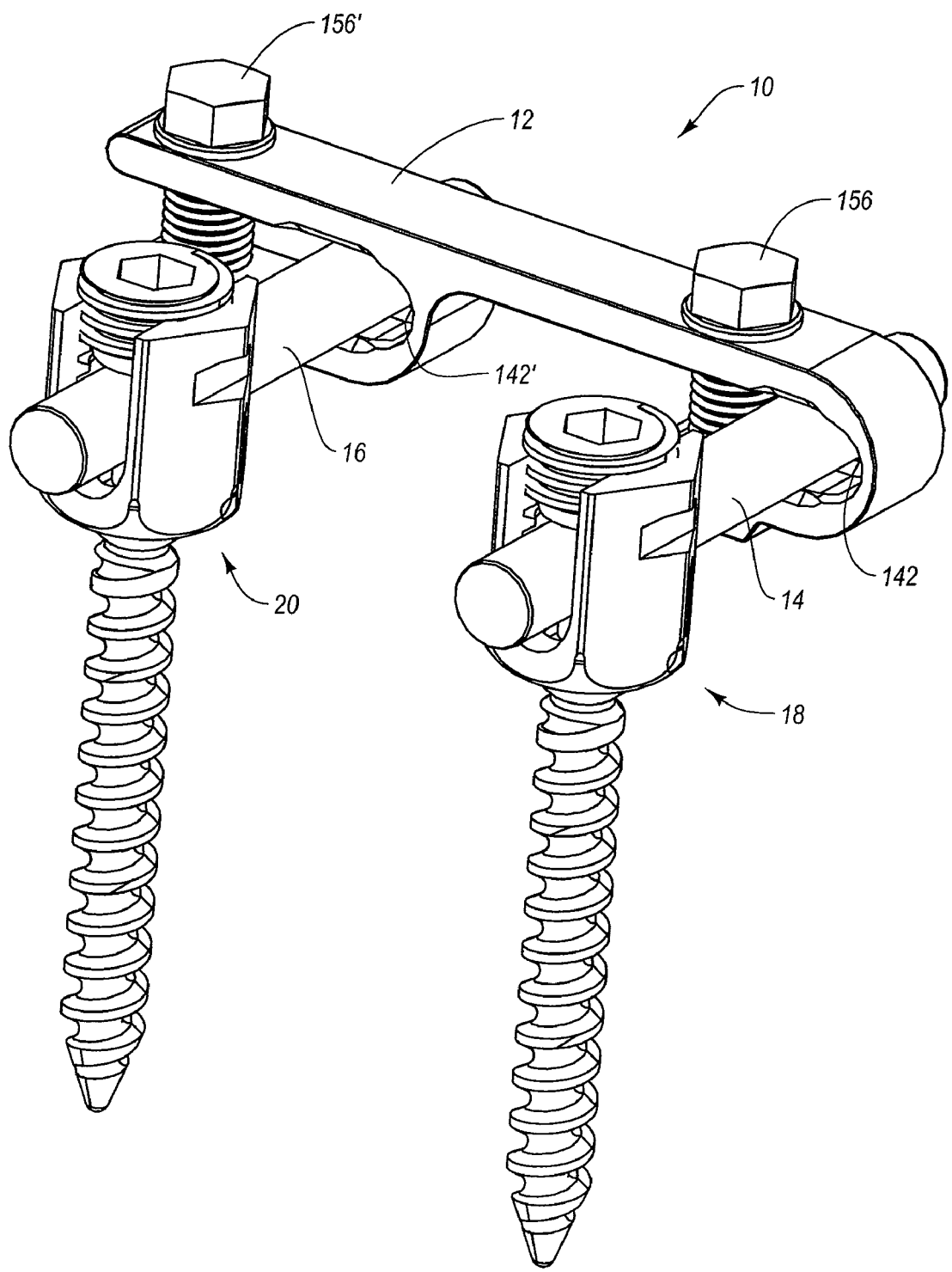
FIG. 1 is a perspective view of one embodiment of a spinal stabilizing system.

Depicted in FIG. 1 is one embodiment of a spinal stabilizing system 10 incorporating features of the present invention. In one embodiment, spinal stabilizing system 10 can be used for stabilizing adjacent vertebrae of a spine as part of a procedure for fusing together the adjacent vertebrae. Spinal stabilizing system 10 can also be used for stabilizing a series of consecutive vertebrae for manipulation of the spine to correct spinal deformities such as scoliosis. It is appreciated that spinal stabilizing system 10 and/or discrete elements thereof can also be used in other procedures for anchoring, manipulating, and/or stabilizing various bones.

Spinal stabilizing system 10 generally comprises a cross link 12 having a first stabilizing rod 14 and a second stabilizing rod 16 mounted on and projecting therefrom. A first anchor assembly 18 is mounted on first stabilizing rod 14 while a second anchor assembly 20 is mounted on second stabilizing rod 16. Anchor assemblies 18 and 20 are identical. Thus, all disclosure with regard to first anchor assembly 18 is also applicable to second anchor assembly 20.

Figure 2:
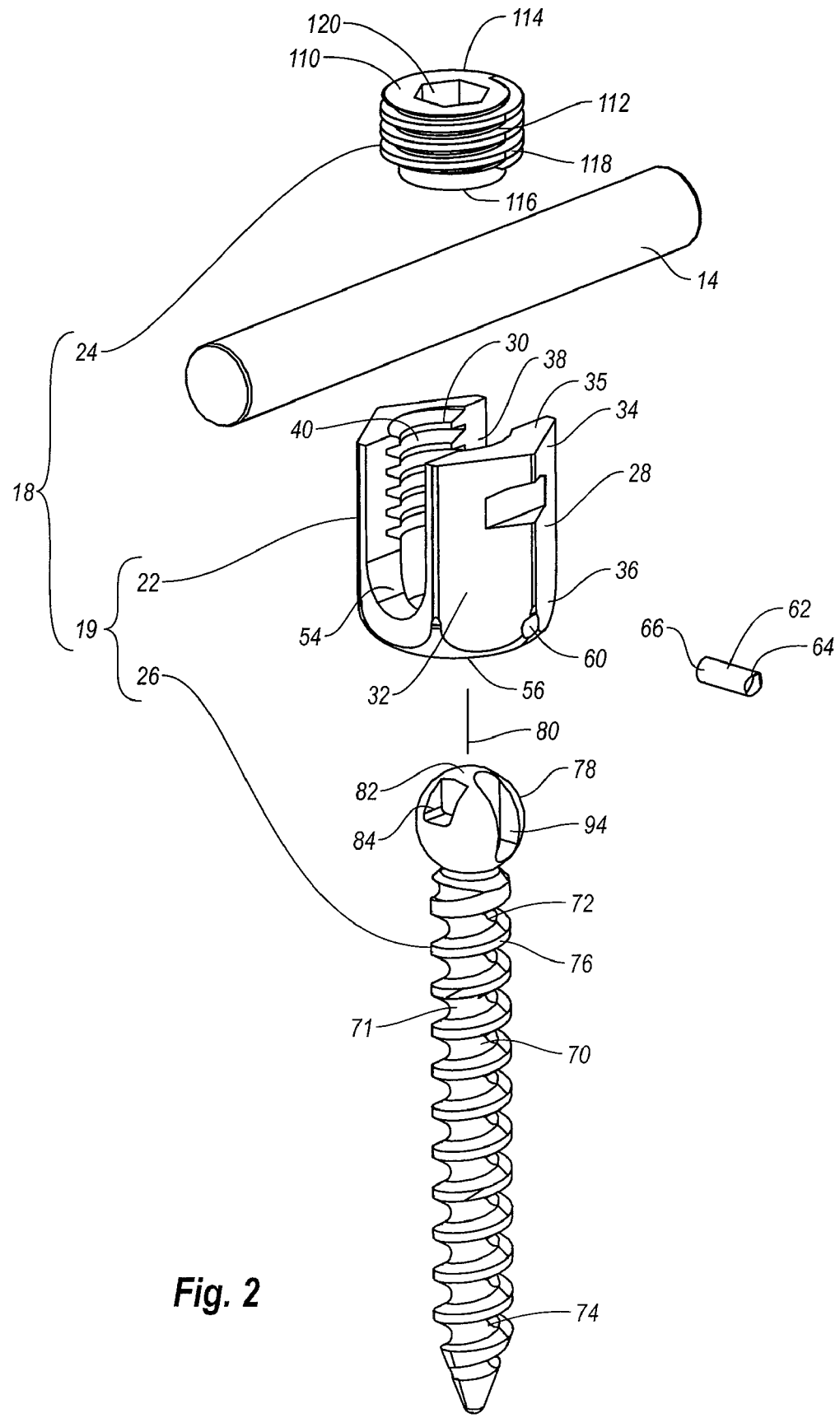
FIG. 2 is an exploded perspective view of an anchor assembly of the spinal stabilizing system depicted in FIG. 1.

As depicted in FIG. 2, anchor assembly 18 comprises an anchor 19 on which a fastener 24 selectively engages. Anchor 19 comprises an elongated screw 26, a collar 22 pivotally mounted on screw 26, and a pin 62 that extends between screw 26 and collar 22. Collar 22 comprises a tubular side wall 28 having an interior surface 30 and an exterior surface 32 that each extend between a first end 34 and an opposing second end 36. First end 34 terminates at a terminal end face 35. Interior surface 30 bounds a longitudinal passage 38 that longitudinally extends through collar 22. Internal threads 40 are formed on interior surface 30 at or toward first end 34.

Figure 3:
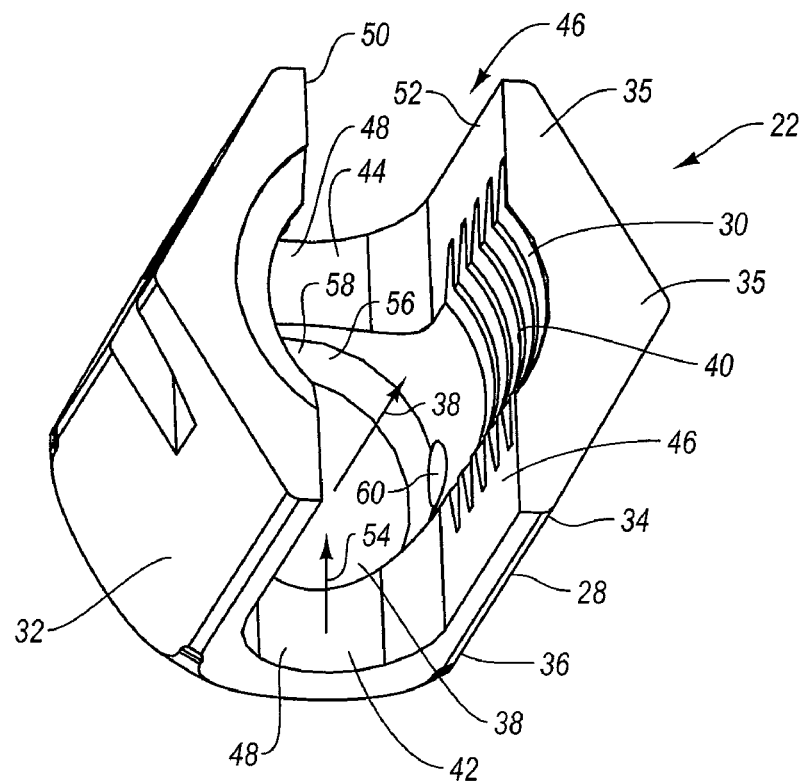
FIG. 3 is a perspective view of the collar of the anchor assembly shown in FIG. 2.
Figure 9:
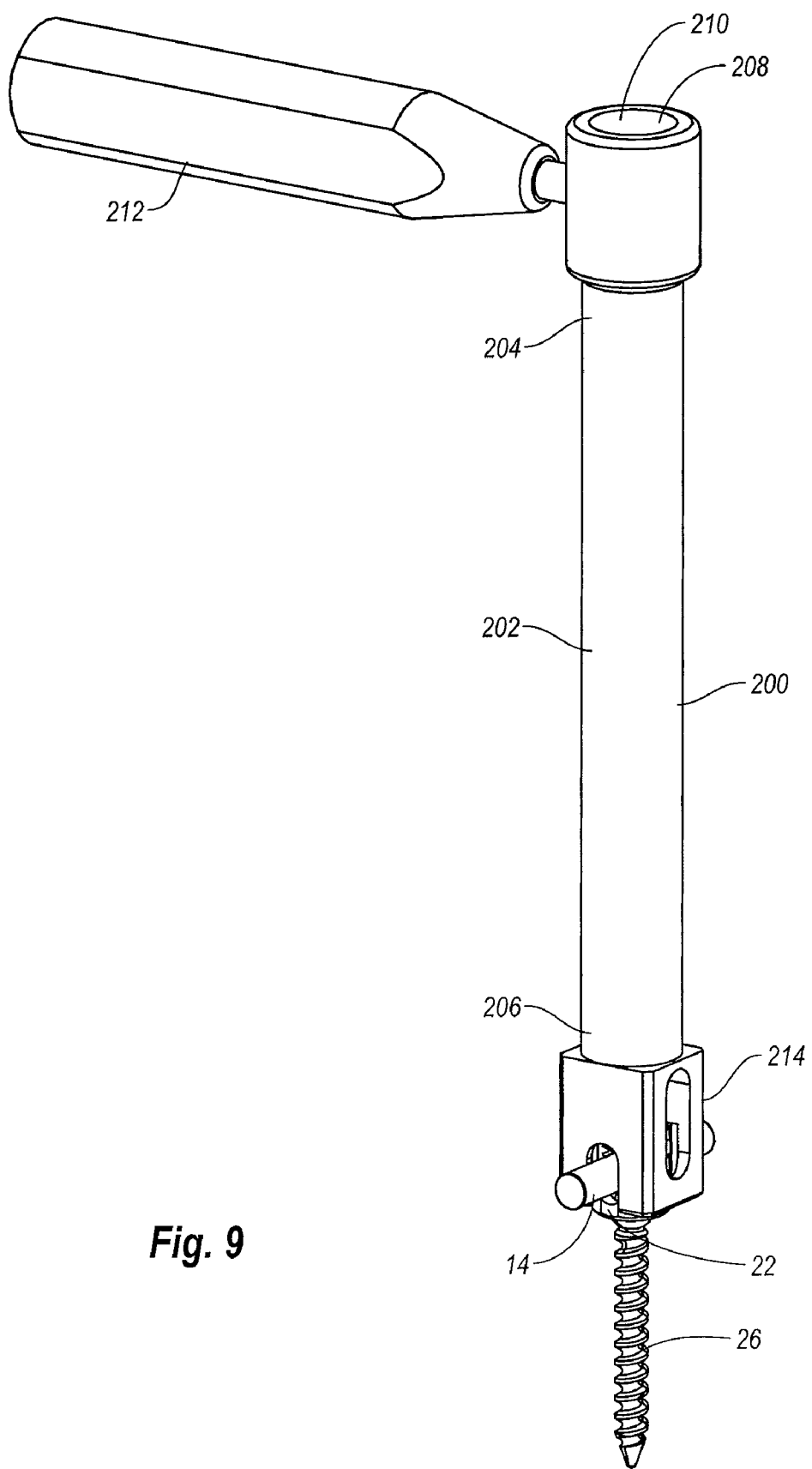
FIG. 9 is a perspective view of an anti-torque device coupling with the anchor assembly of FIG. 1.
Figure 10:
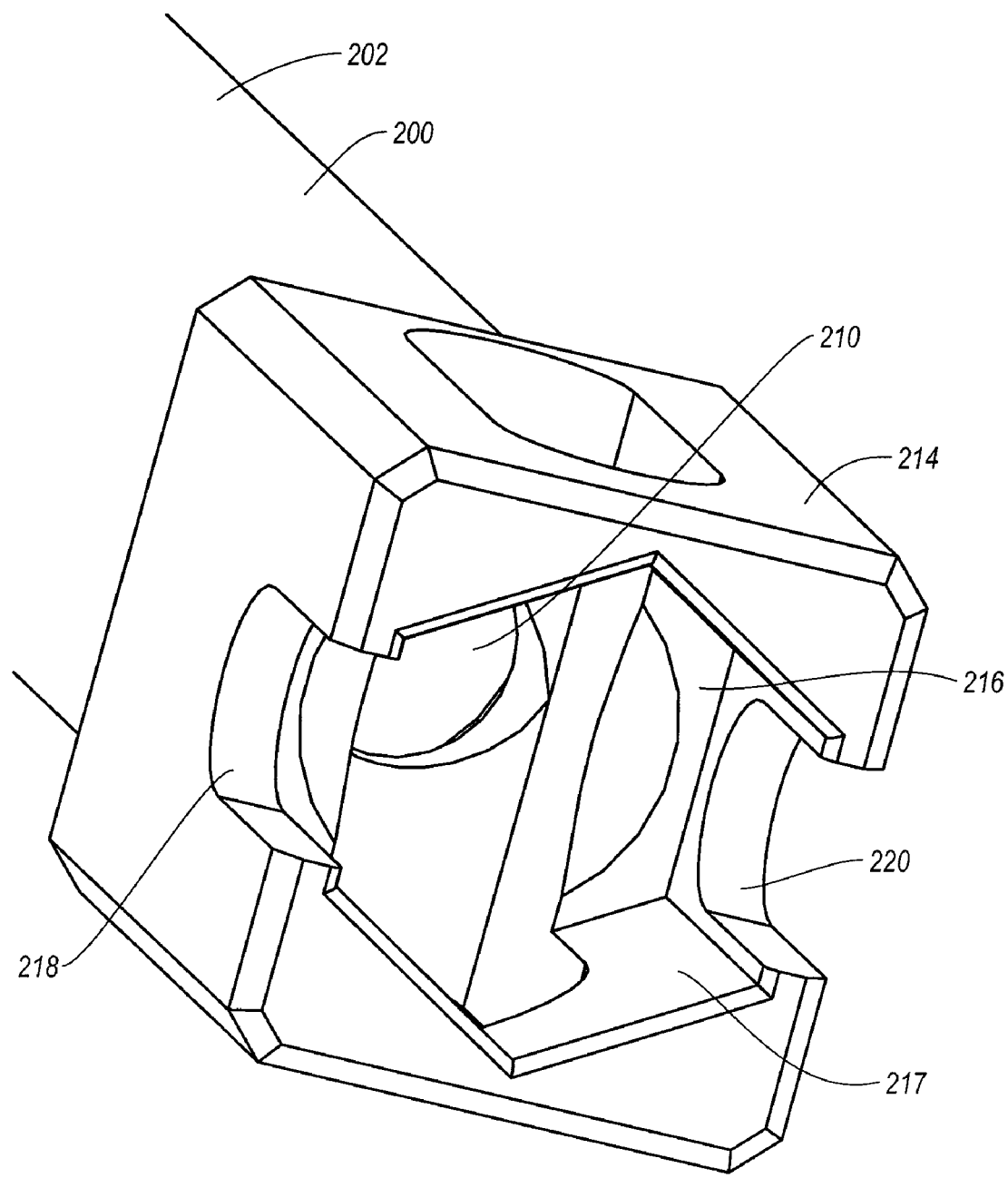
FIG. 10 is a perspective end view of the anti-torque device shown in FIG. 9.

As perhaps best depicted in FIG. 3, exterior surface 32 of side wall 28 has a substantially polygonal transverse cross section. As a result of having a polygonal configuration, an engagement tool, such as depicted in FIGS. 9 and 10, can easily engage exterior surface 32 of collar 22 so as to either rigidly hold collar 22 or facilitate selective rotation of collar 22. In the embodiment depicted, exterior surface 32 has a six sided polygonal configuration. In alternative embodiments, it is appreciated that exterior surface 32 can have a variety of alternative polygonal configurations such as four sided, eight sided, twelve sided, or any other polygonal configuration. In still other embodiments, exterior surface 32 can have any non-circular transverse cross section. As a result of being non-circular, a corresponding socket of an engagement tool can be placed over first end 34 of collar 22 to mechanically engage collar 22.

Furthermore, in the embodiment depicted the polygonal transverse cross section is substantially constant along the length of side wall 28. In an alternative embodiment the polygonal configuration need only extend along a length of side wall 28. The remainder of side wall 28 can be circular or any other desired configuration.

Side wall 28 is formed having a pair of channels 42 and 44 that are disposed on opposing sides of side wall 28 and that transversely extend through side wall 28. In the embodiment depicted, channels 42 and 44 each have a substantially U-shaped configuration. Each channel 42 and 44 has an open mouth 46 that extends through end face 35 and an opposing floor 48 that is rounded. As will be discussed below in greater detail, each channel 42 and 44 is configured so that stabilizing rod 14 can be received therein. In alternative embodiments, floor 48 need not be rounded but can be flat, V-shaped, or have other configurations. Each of channels 42 and 44 are also bounded by opposing side surfaces 50 and 52. Although side surfaces 50 and 52 are shown as being in substantially parallel alignment, in alternative embodiments side surfaces 50 and 52 can be designed to diverge or converge as they project away from floor 48. Other configurations can also be used. Channels 42 and 44 form a portion of a transverse passage that transversely extends through collar 22, as identified by arrow 54, so as to intersect with the longitudinal passage that also extends through collar 22, as identified by arrow 38.

As also depicted in FIG. 3, collar 22 further comprises a shoulder 56 that radially inwardly projects from second end 36 of side wall 28 so as to encircle longitudinal passage 38. Shoulder 56 has a tapered interior surface that forms an annular seat 58. As will be discussed below in greater detail, a portion of screw 26 rests against seat 58 so that collar 22 can pivot relative to screw 26. In alternative embodiments, seat 58 need not completely encircle passage 38. Seat 58 can also comprise two or more spaced apart portions. Finally, a pin hole 60 transversely extends through side wall 28 and/or shoulder 56 at second end 36 of side wall 50. Although not required, pin hole 60 is typically disposed orthogonal to transverse passage 54. As will also be discussed below in greater detail, pin hole 60 is adapted to receive pin 62 (FIG. 2) which has a first end 64 and an opposing second end 66.

Returning to FIG. 2, screw 26 comprises an elongated shaft 70 having an exterior surface 71 extending between a first end 72 and an opposing second end 74. A thread 76 helically encircles and radially outwardly projects from shaft 70 along the length thereof. In one embodiment one or more helical threads can be formed on shaft 70. Thread 76 can have a variety of different pitches and configurations, and, if desired, can be self-tapping.

Figure 4:
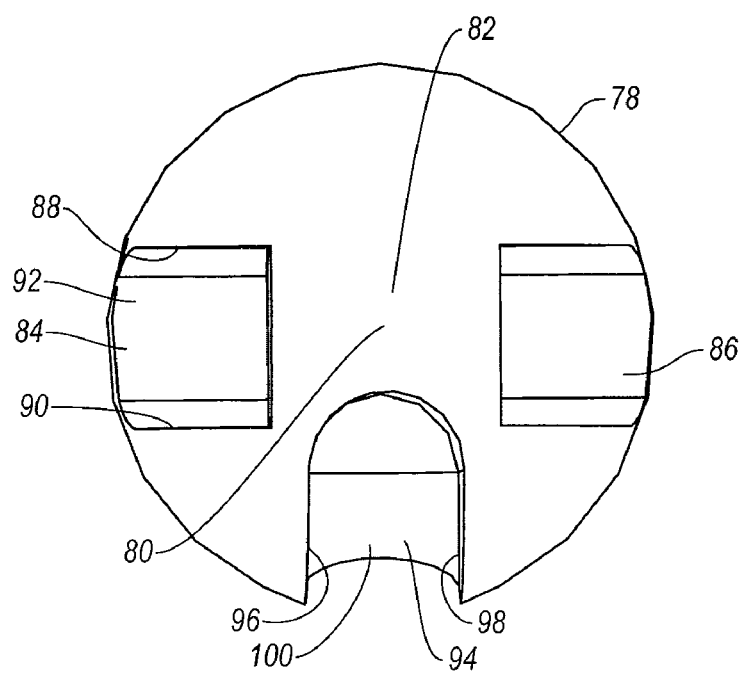
FIG. 4 is a top plan view of the screw of the anchor assembly shown in FIG. 2.

An enlarged head 78 is disposed on first end 72 of shaft 70. Although not required, in the embodiment depicted head 78 has a substantially spherical configuration. It is also noted that shaft 70 has a central longitudinal axis 80 extending therethrough which axis 80 passes through head 78. Head 78 has a rounded crown 82 in the form of a convex dome disposed on a side of head 78 opposite of shaft 70 and through which central longitudinal axis 80 extends. As depicted in FIG. 4, a pair of spaced apart engagement slots 84 and 86 is formed on opposing sides of head 78 at spaced apart locations from central longitudinal axis 80. Each engagement slot 84 and 86 has a pair of opposing inside faces 88 and 90 that are disposed in substantially parallel alignment and which extend down to a floor 92.

As shown in FIGS. 2 and 4, also formed on head 78 at a location spaced apart from central longitudinal axis 80 is an elongated locking slot 94. Locking slot 94 also has a pair of opposing inside faces 96 and 98 which extend to a floor 100. Although not required, inside faces 96 and 98 are shown as being disposed in substantially parallel alignment. In the embodiment depicted, locking slot 94 extends over half the length of head 78 while engagement slots 84 and 86 extend less than half the length of head 78. In alternative embodiments, however, engagement slots 84, 86 and locking slot 94 can be different lengths.

Figure 5:
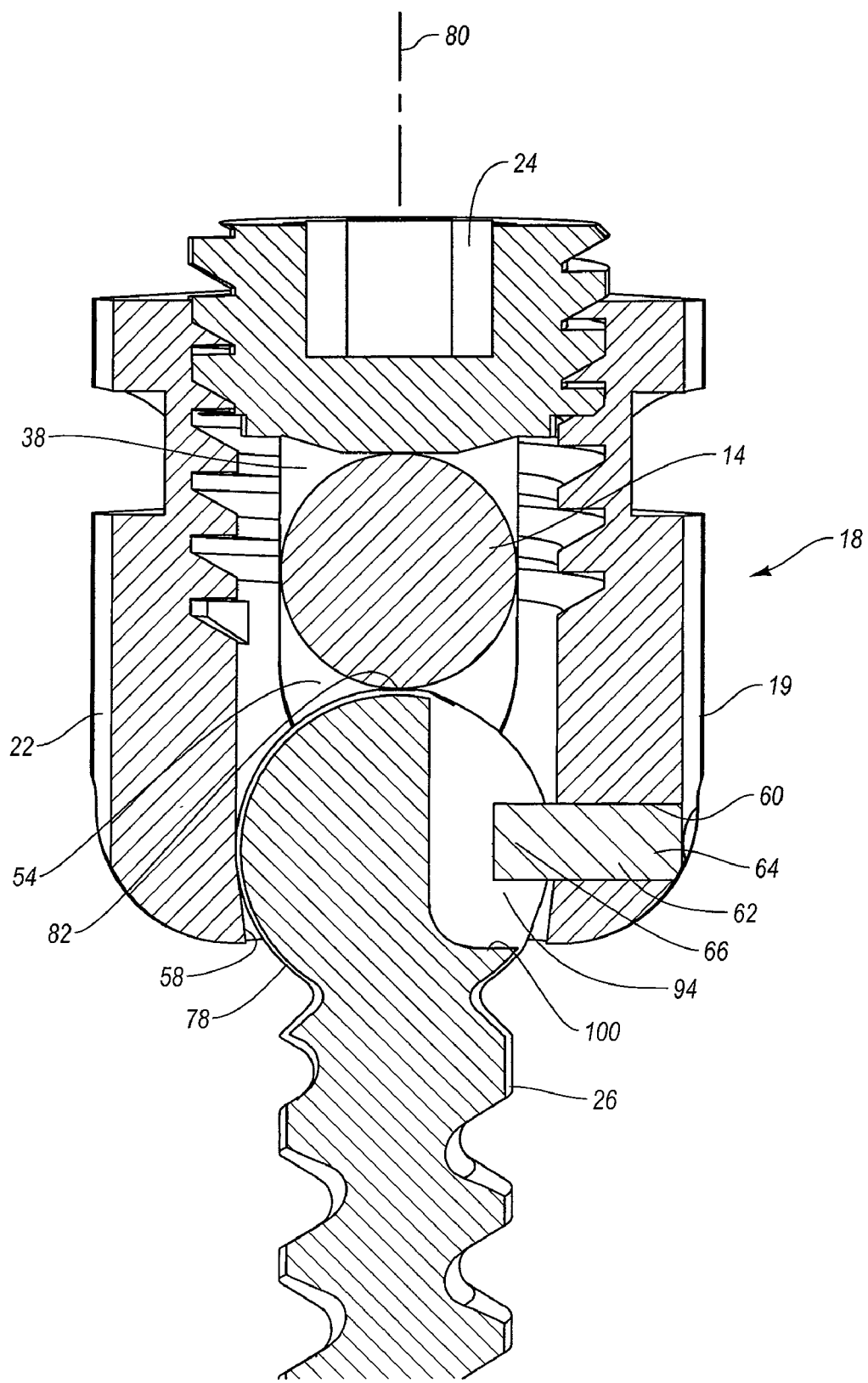
FIG. 5 is a cross sectional side view of the anchor assembly shown in FIG. 1.

Turning to FIG. 5, during assembly of anchor 19, second end 74 of screw 26 is passed down through longitudinal passage 38 of collar 22. Head 78 of screw 26, however, has a maximum diameter that is greater than the minimum diameter of longitudinal passage 38 extending through seat 58 of collar 22. As such, head 78 of screw 26 rests on seat 58 of collar 22 and is prevented from passing through longitudinal passage 38. As a result of the spherical configuration of head 78 and the tapered sloping of seat 58, head 78 can freely slide on seat 58 such that screw 26 and collar 22 can freely pivot relative to each other. Specifically, relative to longitudinal axis 80, collar 22 can pivot any 360° direction. The amount of pivot in one direction from longitudinal axis 80 is typically greater than 10° and more commonly greater than 15°. Other angles can also be formed.

Once screw 26 is seated within collar 22, pin 62 is advanced into pin hole 60. First end 64 of pin 62 is secured within pin hole 60 such as by welding, adhesive, press fit, or other mechanical engagements, such as threaded engagement. In this position, second end 66 of pin 62 projects into locking slot 94 of screw 26. It is noted that pin 62 is spaced apart above floor 100 of locking slot 94. As a result, screw 26 and collar 22 can continue to freely pivot relative to each other. However, because pin 62 extends over floor 100, head 78 is prevented from passing back up through collar 22. Pin 62 also functions to couple screw 26 and collar 22 together so that rotation of collar 22 also facilitates rotation of screw 26. As such, screw 26 can be implanted or removed simply by rotating collar 22. In one embodiment of the present invention means are provided for locking screw 26 to collar 22 so that collar 22 can freely pivot on head 78 of screw 26 and so that rotation of collar 22 facilitates rotation of screw 26. One example of such means comprises pin 62 with corresponding locking slot 94. In alternative embodiments, it is appreciated that pin 62 can come in a variety of different configurations and can be mounted at a variety of different orientations and locations.

Returning to FIG. 2, stabilizing rod 14 typically has a substantially cylindrical configuration and is sized to fit within transverse passage 54 of collar 22. In one embodiment stabilizing rod 14 has a diameter in a range between about 3 mm to about 8 mm. However, in alternative embodiments, stabilizing rod 14 can have a variety of different diameters and can have other transverse cross sections such as polygonal, elliptical, irregular, or the like. However, having a circular transverse cross section provides for uniform engagement and seating with screw 26, fastener 24, and cross link 12. It is appreciated that stabilizing rod 14 can come in a variety of different lengths depending on its intended use. For example, stabilizing rods 14 and 16 will be considerably longer if intended for use in a system for stabilizing four sequential vertebrae in a spine as opposed to stabilizing only two adjacent vertebrae in a spine. Likewise, depending on their intended use, stabilizing rods 14 and 16 can be precontoured along their length. For example, stabilizing rods 14 and 16 can be contoured complementary to the curvature of the portion of the spine to which they will be stabilizing.

As also depicted in FIG. 2, fastener 24 comprises a body 110 having an encircling side wall 112 that extends between a top end face 114 and an opposing bottom end face 116. Radially outwardly projecting from side wall 112 so as to encircle body 110 is a helical thread 118. Recessed on top surface 114 is a polygonal socket 120 adapted to receive a driver. Threads 118 of fastener 24 are configured to threadedly engage with internal threads 40 of collar 22. Accordingly, as depicted in FIG. 5 and as will be discussed below in greater detail, once stabilizing rod 14 is disposed within transverse passage 54 of collar 22, fastener 24 can be screwed into longitudinal passage 38 of collar 22 so that fastener 24 biases stabilizing rod 14 against head 78 of screw 26. In this configuration, stabilizing rod 14 is secured from unwanted movement by being compressed between fastener 24 and head 78 of screw 26. Furthermore, as stabilizing rod 14 pushes against head 78, head 78 is wedged against seat 58 of collar 22, thereby also locking collar 22 relative to screw 26.

Figure 6:
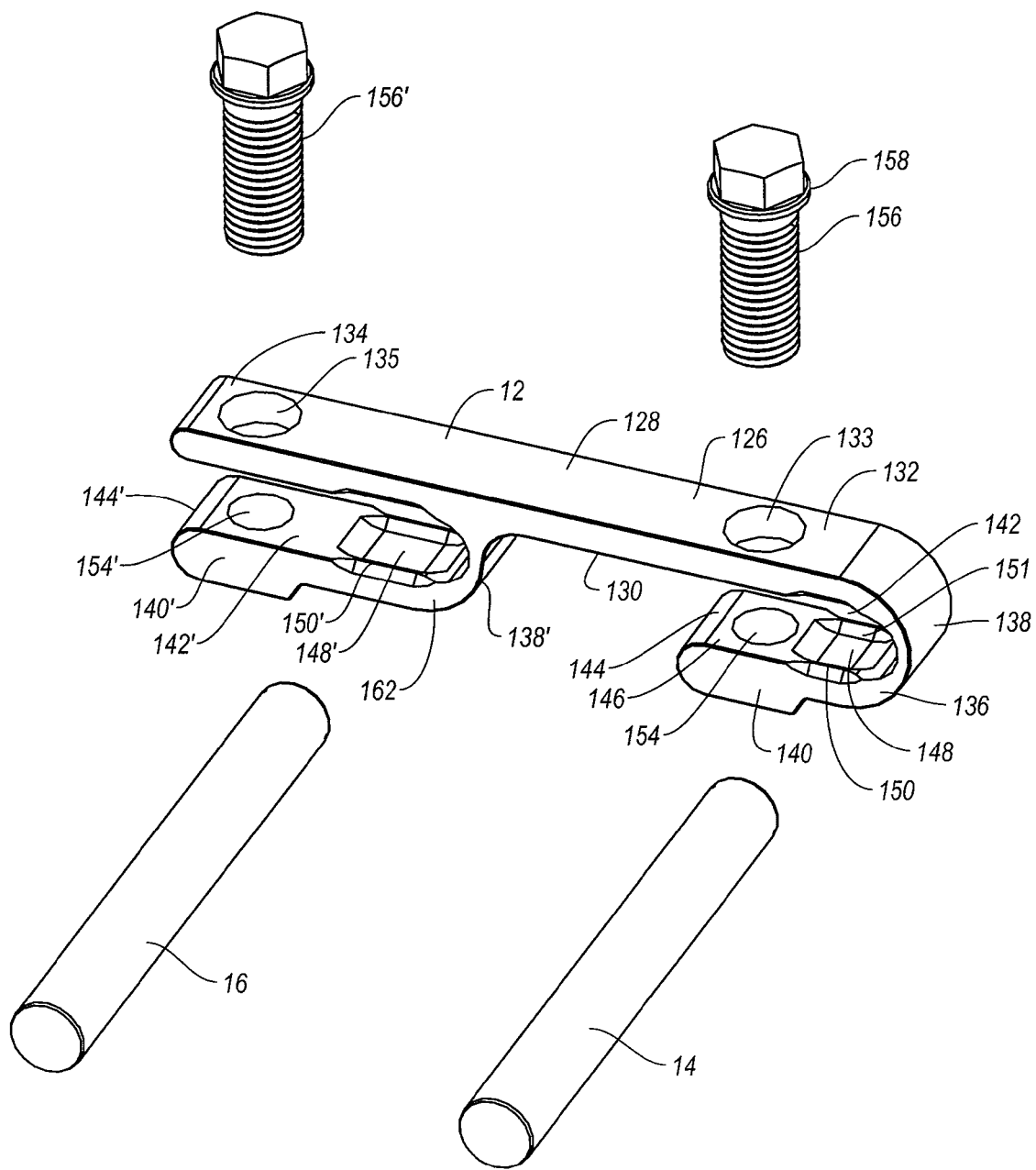
FIG. 6 is an exploded perspective view of the cross link and stabilizing rods of the spinal stabilizing system shown in FIG. 1.

Turning to FIG. 6, cross link 12 comprises a cross bar 126 having a top surface 128 and an opposing bottom surface 130 each extending between a first end 132 and an opposing second end 134. In the embodiment depicted, top surface 128 and bottom surface 130 are substantially flat and are substantially parallel to each other. A first hole 133 extends through cross bar 126 at first end 132 while a second hole 135 extends through cross bar 126 at second end 134. Disposed at first end 132 of cross bar 126 is a first retainer 136. First retainer 136 comprises a first leg 138 that projects downwardly away from bottom surface 130 of cross bar 126 at first end 132 and a second leg 140 that projects from the end of first leg 138 toward second end 134 of cross bar 126 in generally parallel alignment with cross bar 126. First retainer 136 and cross bar 126 combine to form a first slot 142 having a substantially U-shaped configuration with an open mouth 144 formed towards second end 134.

Second leg 140 has an interior surface 146 which in one embodiment can be substantially flat. In the depicted embodiment, however, a pocket 148 is formed on interior surface 146 of second leg 140. As a result of pocket 148, a pair of narrow engagement ridges 150 and 151 is formed on interior surface 146 on opposing sides of pocket 148. Engagement ridges 150 and 151 provide improved biting contact with stabilizing rod 14 so as to improve engagement between cross link 12 and stabilizing rod 14. A similar pocket 148 and engagement ridges 150 and 151 can also be opposingly formed on bottom surface 130 of cross bar 126.

Formed on and/or extending through second leg 140 in alignment with hole 133 is a threaded aperture 154. Once stabilizing rod 14 is positioned within slot 142, a screw 156 is passed down through hole 133 and engaged with threaded aperture 154. Screw 156 has an enlarged head 158 that seats against top surface 128 of cross bar 126 such that by threading screw 156 into aperture 154, stabilizing rod 14 is clamped within slot 142.

A second retainer 162 is also mounted on cross bar 126 so as to project from bottom surface 130 of cross bar 126 at a location between first end 132 and second end 134. Second retainer 162 has substantially the same configuration and component elements as first retainer 130. As such, the same reference characters associated with first retainer 126 with the addition of "'" are used to identify the corresponding elements of second retainer 162. The primary distinction between first retainer 136 and second retainer 162 is that second leg 140' has an extended length. This extended length allows for a tolerance in fit for different spacings for stabilizing rods 14 and 16.

In one embodiment each of the elements of bone stabilizing system 10 is comprised of a metal such as titanium, stainless steel, alloys, or other biocompatible metals. In alternative embodiments, other biocompatible materials such as composites or high strength plastics can also be used. Furthermore, different components of system 10 can be formed from different materials.

Bone stabilizing system 10 will now be discussed with regard to stabilizing a pair of adjacent vertebrae of a spine. Initially, the soft tissue is resected from around the adjacent vertebrae. Two holes are then formed in each vertebra with each hole extending through a corresponding pedicle of the vertebra. An anchor 19 that is sized for the corresponding vertebra is then selected. Second end 74 of screw 26 of anchor 19 is then positioned within the preformed hole and a driver is used to secure screw 25 within the hole in the vertebra.

Figure 7:
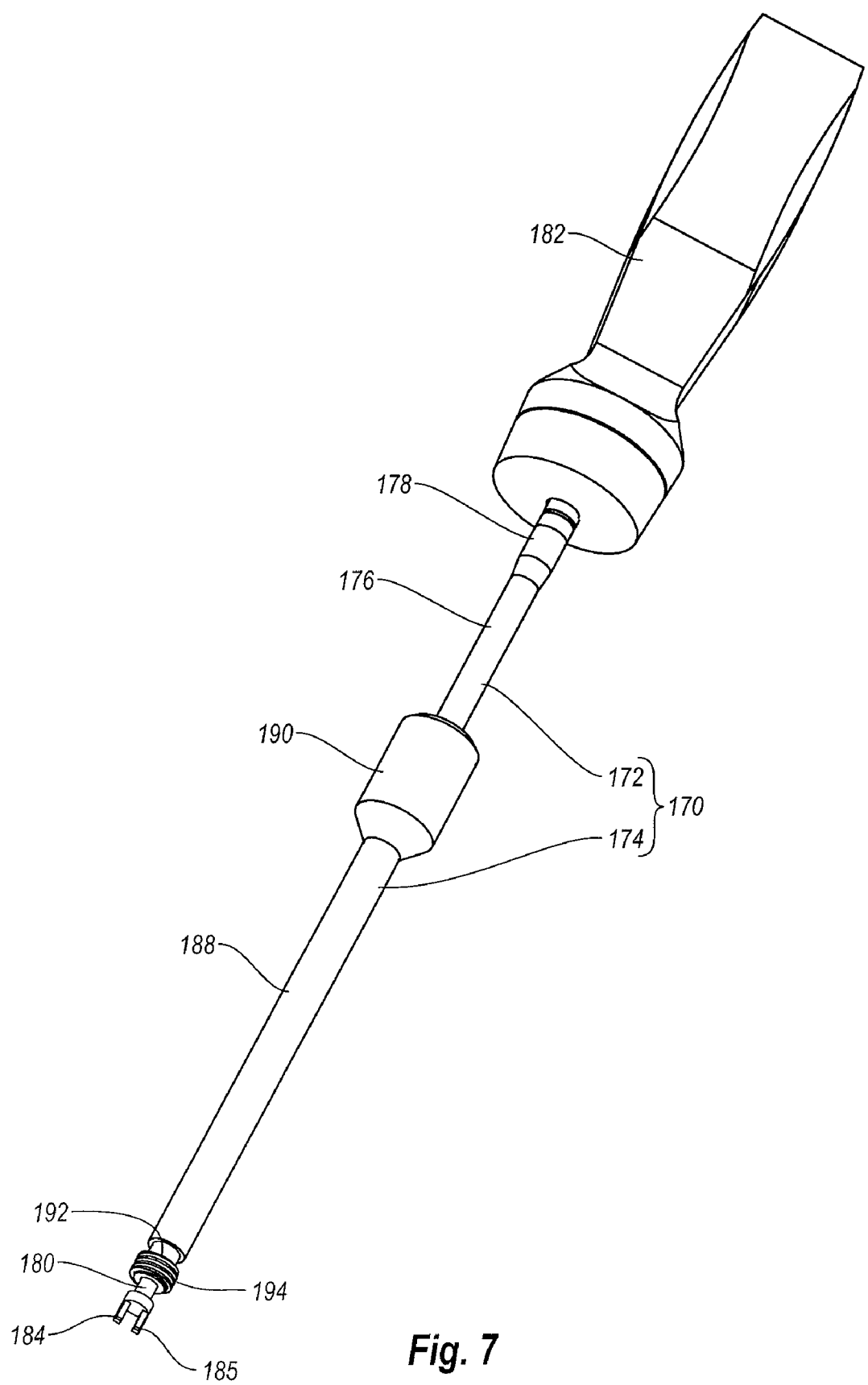
FIG. 7 is a perspective view of a driver assembly.

Depicted in FIG. 7 is one embodiment of a driver assembly 170 that can be used for mounting anchor 19. Driver assembly 170 comprises a driver 172 and a stabilizer 174. Driver 172 comprises an elongated shaft 176 having a first end 178 and opposing second end 180. A handle 182 is mounted at first end 178 while forked prongs 184 and 185 are mounted on second end 180. Stabilizer 174 comprises an elongated sleeve 188 having a first end 190 and an opposing second end 192. Sleeve 188 freely encircles shaft 176 such that sleeve 188 can freely rotate about shaft 176. Encircling and radially outwardly projecting from second end 192 of sleeve 188 is a helical biasing thread 194.

Figure 8:
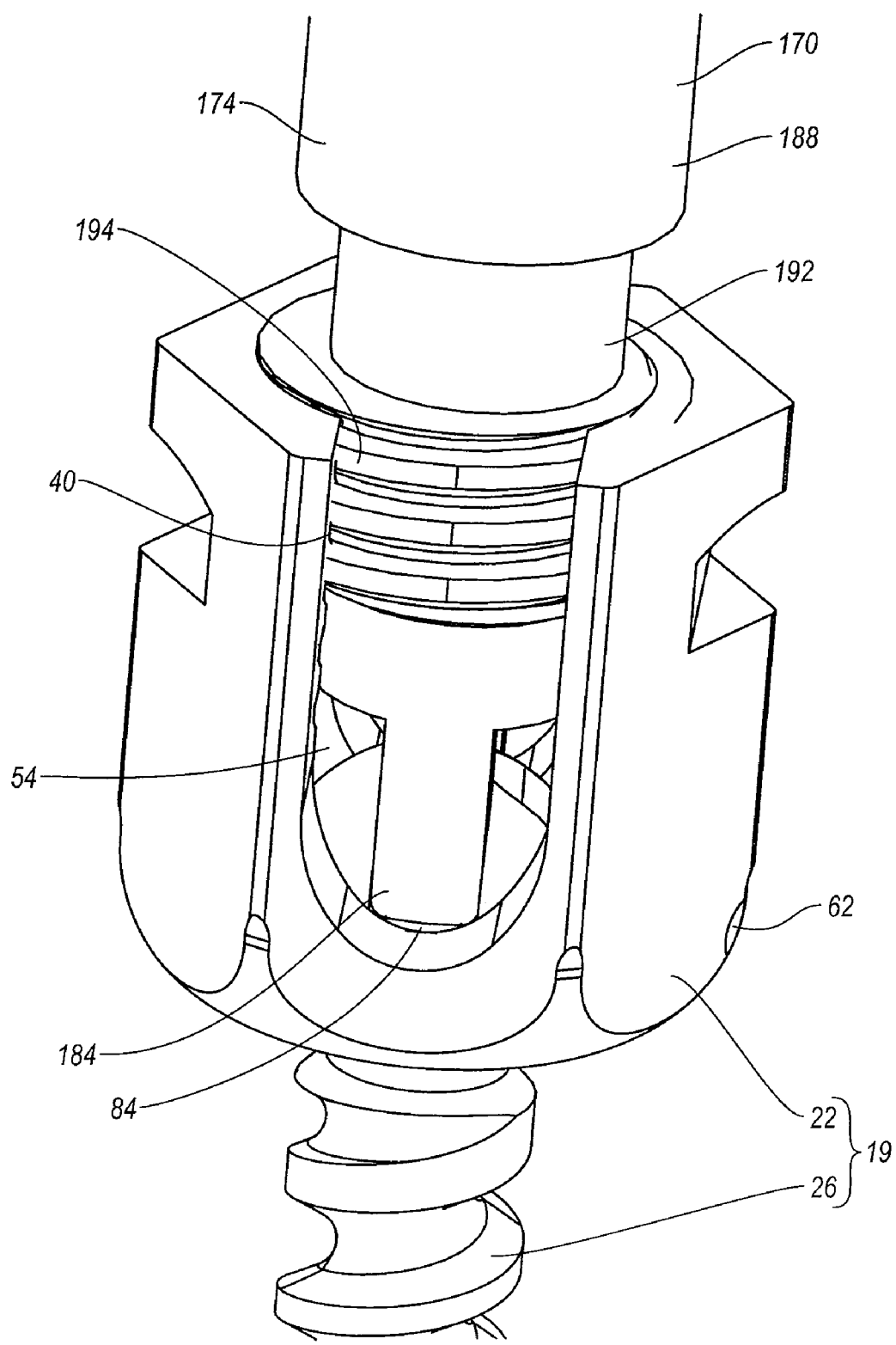
FIG. 8 is an enlarged perspective view of an end of the driver assembly shown in FIG. 7 engaging the anchor of FIG. 1.

Turning to FIG. 8, prior to implanting anchor 19, prongs 184 and 185 are advanced down through collar 22 and are received within engagement slots 84 and 86 on screw 26. In turn, second end 192 of sleeve 188 is also advanced into collar 22. By rotating sleeve 188, biasing threads 194 threadedly engage with internal threads 40 of collar 22, thereby securing stabilizer 174 to collar 22. In this assembled configuration, screw 26 is now held by driver assembly 170 such that screw 26 is prevented from pivoting relative to collar 22. By using driver assembly 170, the surgeon can position the tip of screw 26 into the hole formed in the pedicle of the vertebra. Screw 26 can then be advanced and secured within the hole by simply rotating handle 182. Once screw 26 is advanced to the desired depth, stabilizer 174 is unscrewed from collar 22 and driver assembly 170 is removed from anchor 19.

As previously discussed, collar 22 is prevented from rotating relative to screw 26 as a result of pin 62. In the present case, this fixed relationship between collar 22 and screw 26 aids in the easy attachment and removal of biasing threads 194 into and out of collar 22. Furthermore, it is appreciated that driver assembly 170 is only one embodiment of a driver that can be used for mounting anchor 19. In an alternative embodiment, an elongated driver can be used that simply has a socket formed on the end thereof that is complimentary to the exterior surface of collar 22. One example of such a driver is discussed below with regard to FIGS. 9 and 10. Again, because pin 62 prevents rotation of collar 22 relative to screw 26, rotation of the driver that engages collar 22 facilitates rotation of collar 22 which in turns facilitates rotation of screw 26.

This latter described driver is especially useful in situations where it is needed to remove anchor 19 after having been previously implanted. That is, after anchor 19 has been implanted for an extended period of time, soft tissue and/or bone can grow into transverse passage 54 and engagement slots 84 and 86. As a result, attempting to slide prongs 184 and 185 into engagement slots 84 and 86 may require significant time and effort. By using the present embodiment, a driver can simply be slid over first end 34 of collar 22. Rotation of the driver would then facilitate removal of anchor 19 without having to directly engage screw 26. Having collar 22 with the polygonal configuration also aids in the manipulation and use of anchor 19 during minimally invasive procedures.

The above described process is used to mount a separate anchor 19 into each of the holes of the two adjacent vertebrae. As such, an anchor 19 is mounted on the lateral side of each vertebra and the medial side of each vertebra. The two laterally disposed anchors 19 are orientated so that the transverse passages 54 thereof are substantially aligned. The two medially disposed anchors 19 are similarly orientated. First stabilizing rod 14 is then positioned within transverse passages 54 of the two laterally disposed anchors 19 while second stabilizing rod 16 is disposed within transverse passages 54 of the two medially disposed anchors 19. Here it is appreciated that collar 22 of each anchor 19 is free to pivot relative to screw 26 as previously discussed. By pivoting collar 22, stabilizing rods 14 and 16 can be easily received within transverse passage 54 of each collar 22.

Once the stabilizing rods 14 and 16 are positioned, fastener 24 is mounted within first end 34 of each collar 22. As previously discussed, this is accomplished by inserting a driver into socket 120 of fastener 24 and then screwing fastener 24 into first end 34 of collar 22. During the mounting of fastener 24, it is desirable to minimize unwanted torque on collar 22 so as to prevent unwanted movement thereof and prevent unwanted stress on the spine.

Depicted in FIGS. 9 and 10 is one embodiment of an anti-torque device 200 that can be used to minimize torque on collar 22 during mounting of fastener 24. Anti-torque device 200 comprises a tubular sleeve 202 having a first end 204 and an opposing second end 206. Sleeve 202 has an interior surface 208 that bounds the passageway 210 longitudinally extending through sleeve 202. A handle 212 orthogonally projects out from first end 204 of sleeve 202.

Formed at second end 206 of sleeve 202 is an engagement head 214. As depicted in FIG. 10, head 214 at least partially bounds a socket 216 having an interior surface 217 with a configuration complimentary to exterior surface 32 of collar 22. Socket 216 communicates with passageway 210 extending through sleeve 202. Channels 218 and 220 transversely extend through head 214 on opposing sides of socket 216 so that each channel 218 and 220 communicates with socket 216. Channels 218 and 220 are shown having a configuration substantially the same as channels 42 and 44 previously discussed with regard to collar 22. Other designs can also be used.

To prevent unwanted forces on collar 22 and the spine during attachment and tightening of fastener 24, engagement head 214 is advanced over first end 34 of collar 22 so that stabilizing rod 14 is received within channels 218 and 220. In this position, engagement head 214 is directly engaging both collar 22 and stabilizing rod 14. A driver, not shown, having a polygonal end complimentary to socket 120 of fastener 24 is advanced down through passageway 210 of sleeve 202. The driver engages with fastener 24 and is used to rotate fastener 24. Concurrently with rotating fastener 24, the operator applies an opposing resistance force by holding and/or pulling handle 212 of anti-torque device 200. In the depicted embodiment, head 214 is designed to pass over stabilizing rod 14. In alternative embodiments, however, channels 218 and 220 can be eliminated. In these embodiments, head 214 need only extend down to stabilizing rod 14 but not over stabilizing rod 14. This is because engagement head 214 directly engages collar 22 and thus need not engage stabilizing rod 14 to apply the opposing anti-torque force.

Figure 14:
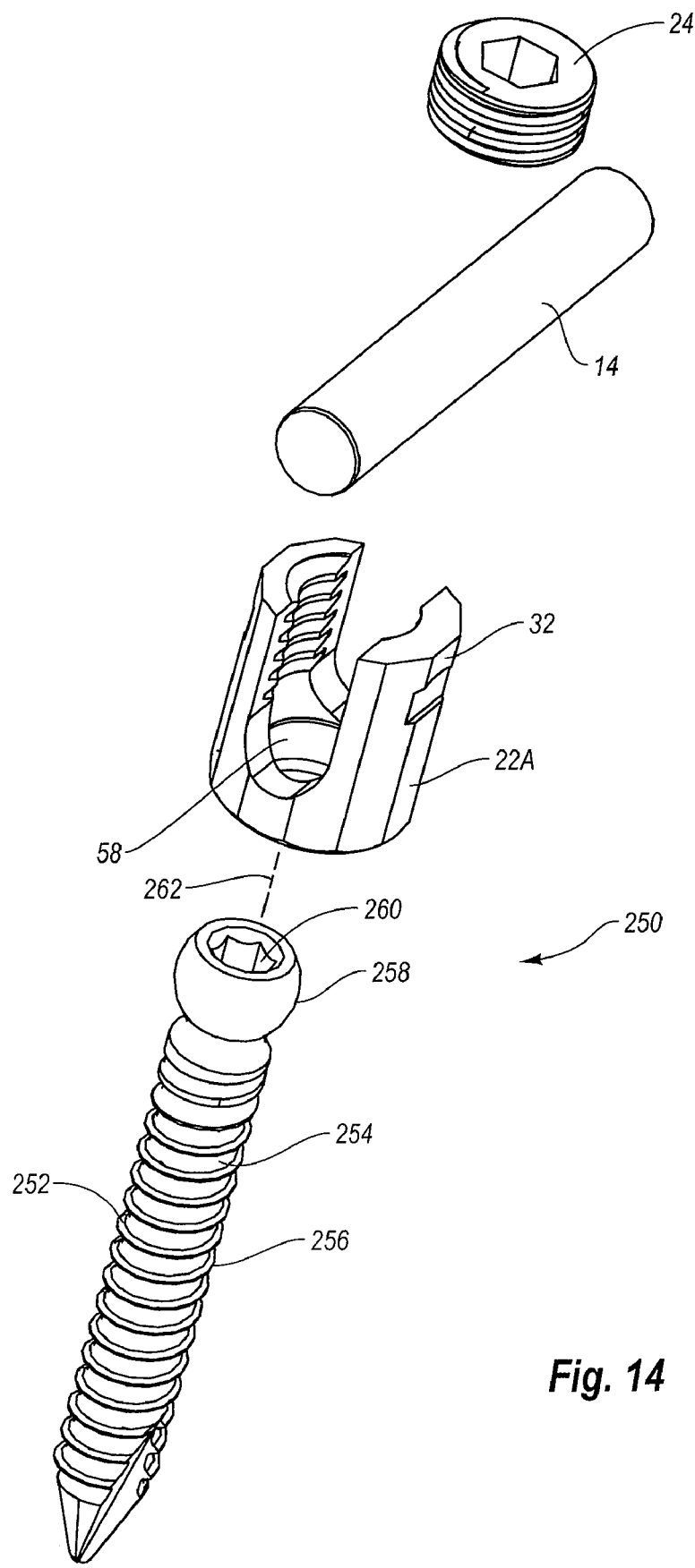
FIG. 14 is an exploded perspective view of an alternative embodiment of an anchor assembly.

As previously discussed with regard to FIG. 5, as fastener 24 is screwed down into collar 22, stabilizing rod 14 biases against rounded crown 82 of screw 26. It is appreciated that depending upon the placement of screws 26, collars 22 may need to be pivoted out of linear alignment with screws 26 so that stabilizing rod 14 can be positioned within transverse passageway 54 of each anchor 19. As a result of crown 82 being rounded, uniform engagement is formed between stabilizing rod 14 and head 78 independent of the orientation of collar 22. In contrast, if crown 82 were flattened, such as by forming a central aperture on head 78 as depicted in FIG. 14, an asymmetrical force may be applied by stabilizing rod 14 against head 78 tending to further pivot collar 22.

Once fastener 24 is secured within collar 22, anti-torque device 200 and the corresponding driver are removed. This process is then repeated for each of the other anchors 19. Finally, one or more cross links 12 are secured to each of stabilizing rods 14 and 16 so as to prevent lateral movement of stabilizing rods 14 and 16. Specifically, with screws 156 and 156' removed, cross link 12 is simply slid over stabilizing rods 14 and 16 so that stabilizing rods 14 and 16 are received within slots 142 and 142'. Screws 156 and 156' are then passed down through holes 133 and 135 and engaged with threaded apertures 154 and 154', thereby crimping cross link 12 onto stabilizing rods 14 and 16 as shown in FIG. 1. Mounting of bone stabilizing system 10 is then complete.

Figure 11:
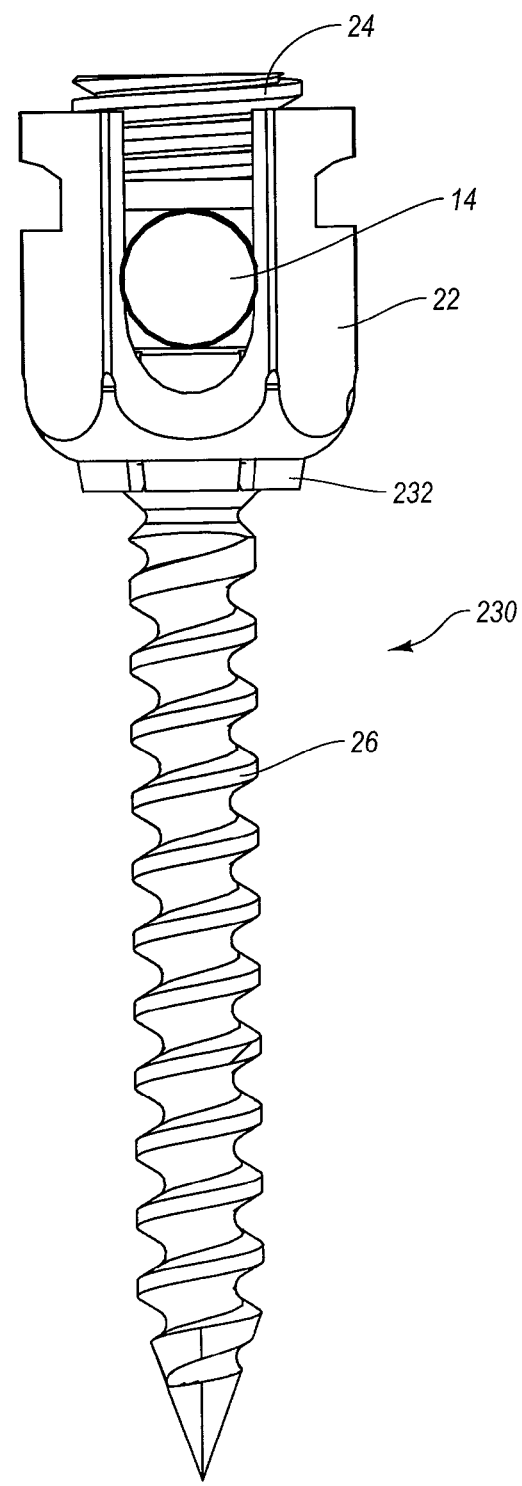
FIG. 11 is an elevated side view of an alternative embodiment of an anchor assembly having a collet.
Figure 12:
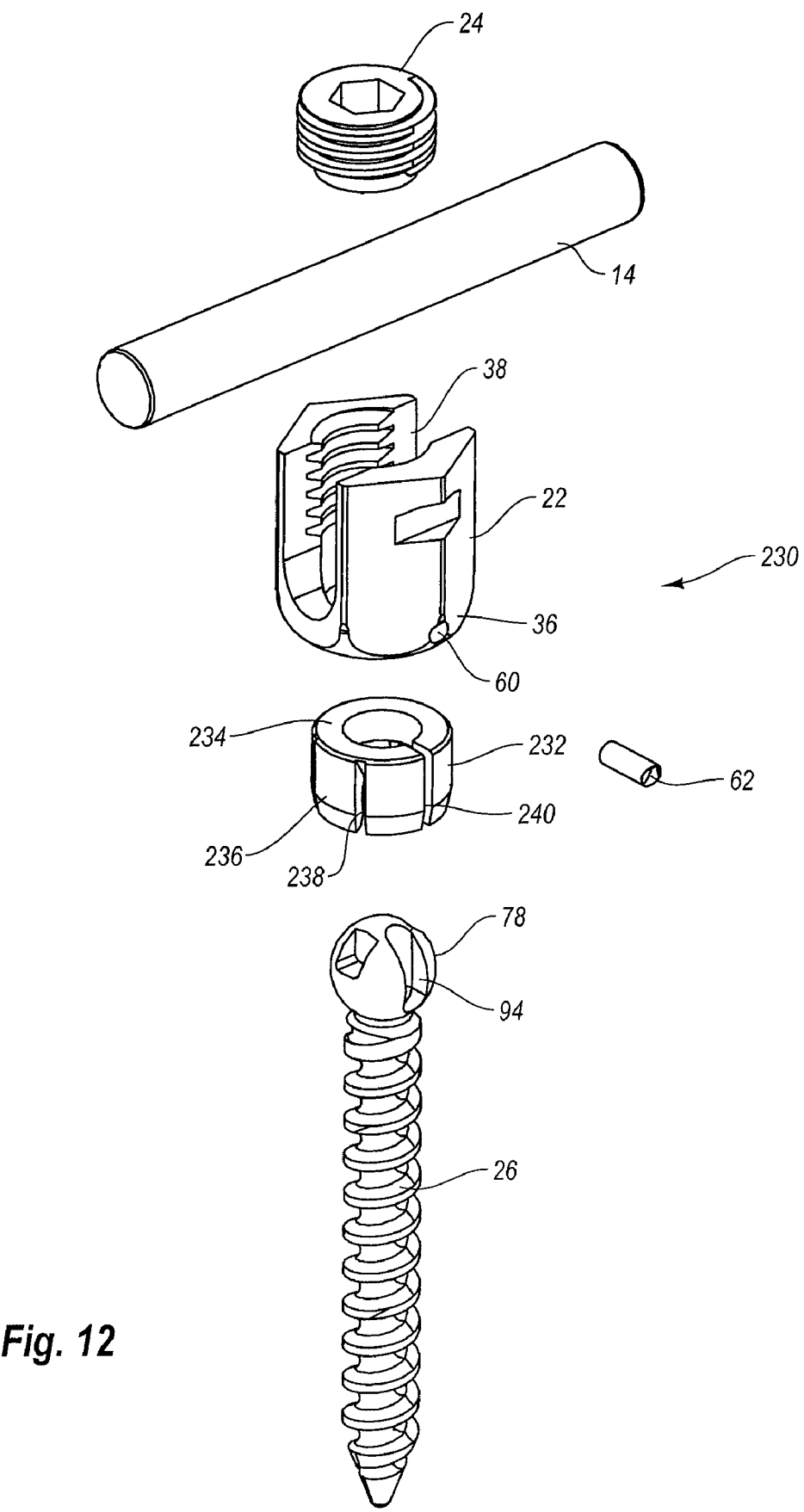
FIG. 12 is an exploded perspective view of the anchor assembly shown in FIG. 11.
Figure 13:
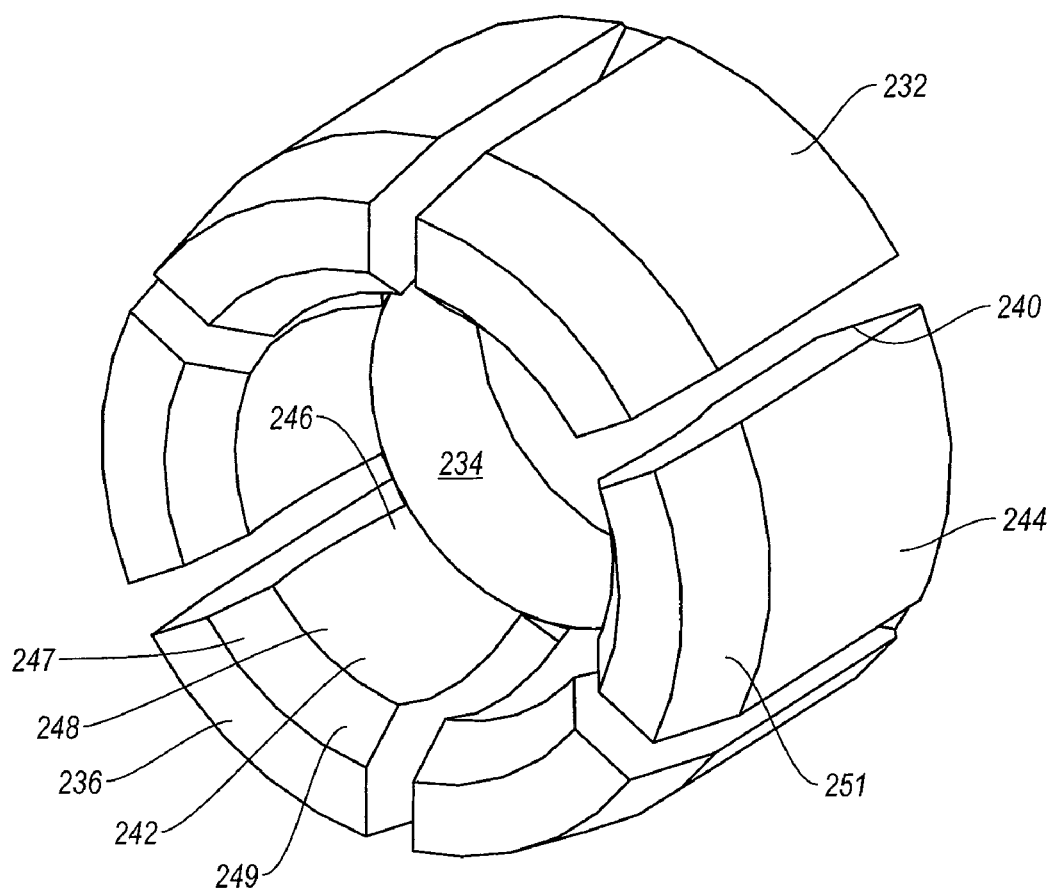
FIG. 13 is a perspective view of the collet of the anchor assembly shown in FIG. 12.

It is appreciated that anchor assembly 18 can come in a variety of different configurations. For example, depicted in FIG. 11 is an alternative embodiment of an anchor assembly 230 incorporating features of the present invention. Common features between anchor assembly 230 and anchor assembly 18 are identified by like reference characters. For example, anchor assembly 230 comprises collar 22, screw 26, and fastener 24. However, in contrast to anchor assembly 18, anchor assembly 230 further comprises an annular collet 232. As depicted in FIGS. 12 and 13, collet 232 comprises an annular ring 234 having a plurality of spaced apart fingers 236 downwardly projecting therefrom. In view of the spacing between fingers 236, a slot 238 is formed between adjacent fingers 236. One slot 240 also extends through ring 234 such that ring 234 has a substantially C-shaped configuration. The formation of slot 240 enables collet 232 to be resiliently constricted for mounting within collar 22.

Each finger 236 has an interior surface 242 and an exterior surface 244 that each extends between a first end 246 and an opposing second end 247. Interior surface 242 comprises a retention portion 248 formed at first end 246 having a concave curvature extending along the length thereof and a concave curvature transversely extending across the width thereof. Interior surface 242 also has a tapered portion 249 formed at second end 248 that slopes radially outward. A radially inwardly sloping tapered portion 251 is also formed on exterior surface 244 at second end 247.

During assembly, collet 232 is radially constricted and then advanced into longitudinal passage 38 of collar 22 from second end 36. As collet 232 is released, it resiliently, radially outwardly extends to its prior configuration so that tapered portion 251 on exterior surface 244 of collet 232 rests against seat 58 (FIG. 6) of collar 22. Head 78 of screw 26 is then pressed into collet 232 so as to seat against retention portions 248 of fingers 236. Any attempts to draw screw 26 out of collet 232 causes fingers 236 to biases against seat 58 of collar 22 which in turn radially constricts fingers 236 so as to further engage head 78, thereby preventing screw 26 from disengaging from collar 22. In this configuration, however, collet 232 and collar 22 can pivot about head 78 of screw 26. Furthermore, if desired, pin 62 can be secured within pin hole 60 of collar 22 so as to pass through slot 240 on collet 232 and rest within locking slot 94. As a result of pin 62, collar 22 would be prevented from rotating relative to screw 26. In alternative embodiments, however, pin 62 can be eliminated and collar 22 can be free to rotate relative to screw 26. During use, stabilizing rod 14 biases against collet 232 as opposed to head 78 of screw 26.

Depicted in FIG. 14 is another alternative embodiment of an anchor assembly 250 incorporating features of the present invention. Like elements between anchor assembly 18 and anchor assembly 250 are identified by like reference characters. Anchor assembly 250 comprises a collar 22A which is substantially identical to collar 22 except that exterior surface 32 thereof has 12 sides as opposed to 6 sides. A screw 252 is shown having a shaft 264 with self-tapping helical thread 256 projecting therefrom. Mounted at the end of shaft 254 is a rounded head 258. Head 258 has a polygonal socket 260 formed on a top end thereof in alignment with the central longitudinal axis 262 of screw 252. Socket 260 is configured to receive a driver for threading screw 252 into bone.

During assembly, screw 252 is advanced down through collar 22A so that head 258 rests against seat 58. As a result, collar 22A can pivot relative to head 258. However, in this embodiment a pin does not extend between collar 22A and head 258, as such collar 22A can freely rotate relative to screw 254. Stabilizing rod 14 and fastener 24 function as with other embodiments. In yet another alternative embodiment, it is appreciated that head 78 of screw 26 shown in the anchor assembly 230 of FIG. 12 can be replaced with head 258 of anchor assembly 250.

Figure 15:
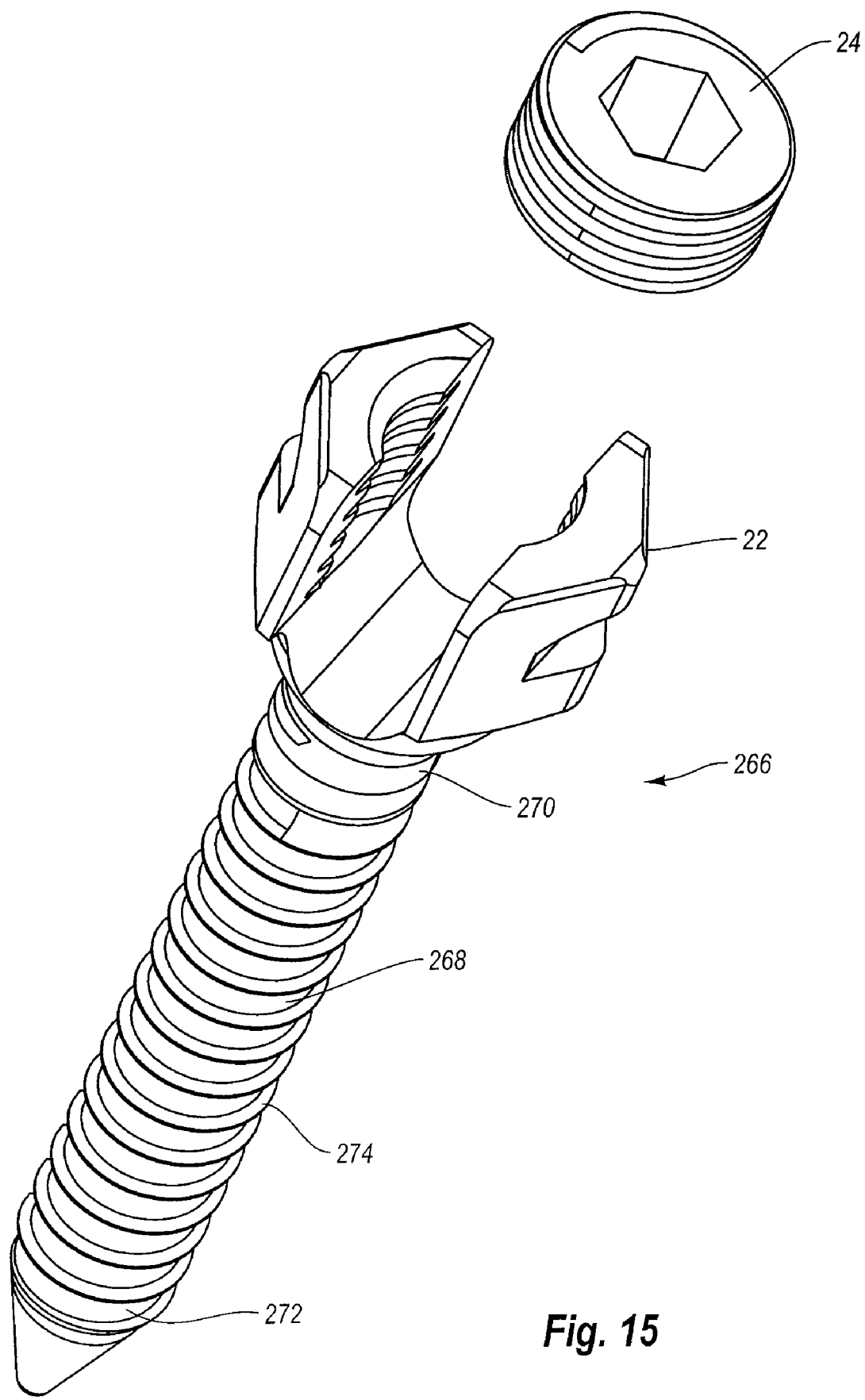
FIG. 15 is a perspective view of another alternative embodiment of an anchor assembly where the collar is integrally formed with the screw.

Depicted in FIG. 15 is another embodiment of an anchor assembly 266. Anchor assembly 266 substantially comprises collar 22 and screw 26 being integrally formed together with the removal of head 78. Specifically, anchor assembly 266 comprises a shaft 268 having a first end 270 and an opposing second end 272. Helical threads 274 encircle shaft 268 and extend along the length thereof. Collar 22 is integrally formed on first end 270 of shaft 268. As a result, collar 22 cannot pivot or rotate independent of shaft 268. Fastener 24 selectively engages collar 22 as with prior embodiments.

Figure 16:
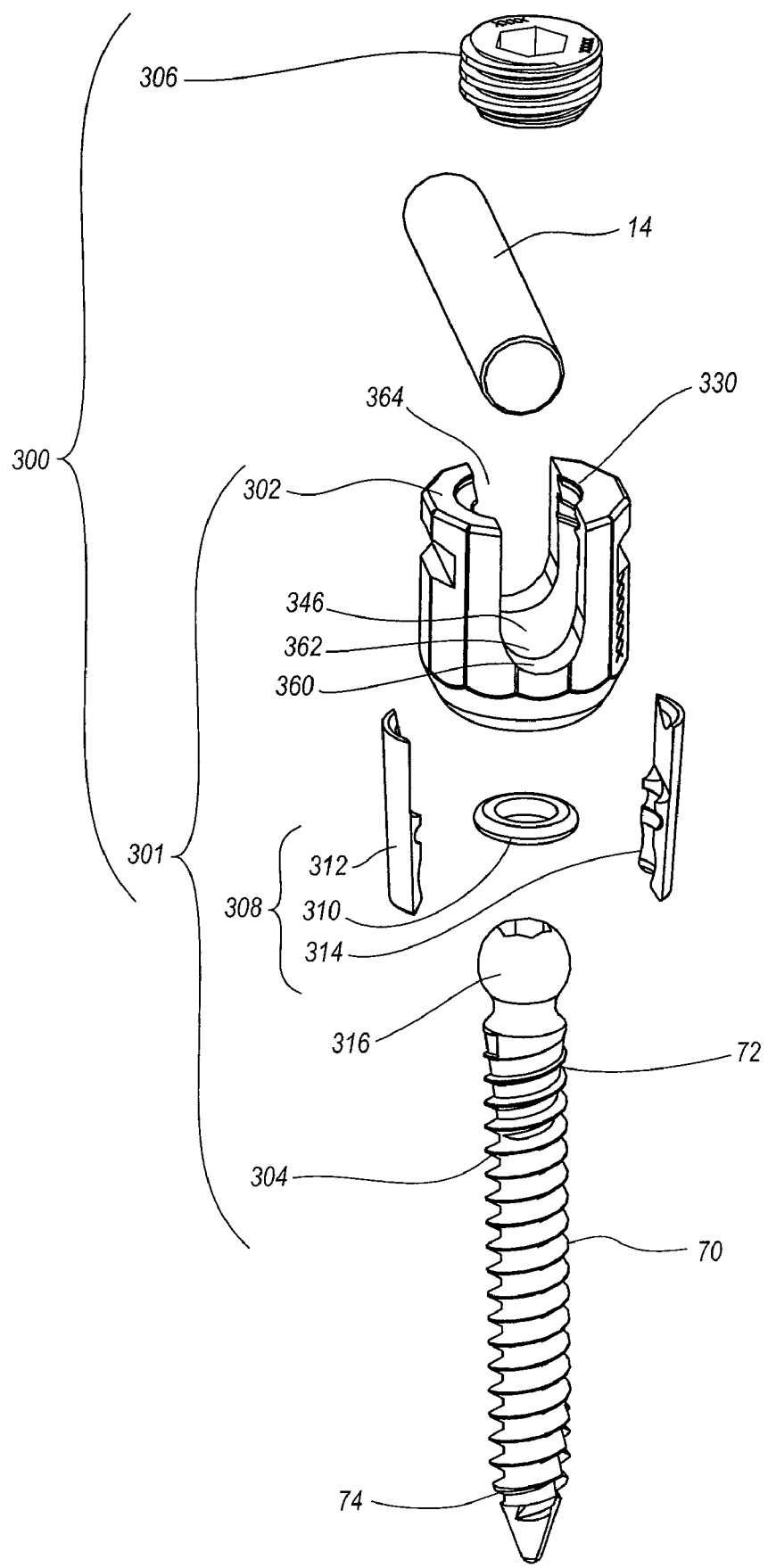
FIG. 16 is an exploded perspective view of another alternative embodiment of an anchor assembly that uses a clamping assembly.

Anchor assembly 18 (FIG. 2) can also be configured to secure the collar to the screw and prevent the collar from moving relative to the screw yet simultaneously allow the rod to freely rotate and move transversely within the transverse passage. This allows a doctor more flexibility when the doctor desires to further separate or bring together vertebrae that have been crushed or otherwise affected because the doctor can move the anchor assembly relative to the rod after the anchor assembly has been rigidly attached to the vertebra, causing the vertebra to move with the anchor assembly. For example, depicted in FIG. 16 is an alternative embodiment of an anchor assembly 300 incorporating features of the present invention. Common features between anchor assembly 300 and anchor assembly 18 are identified by like reference characters. Similar to anchor assembly 18, anchor assembly 300 comprises an anchor 301 on which a fastener 306 selectively engages. Similar to anchor 19, anchor 301 comprises a collar 302 and a screw 304. In contrast to anchor 19, however, anchor 301 further comprises a clamping assembly 308 having a ring 310 and a pair of spaced apart clamp arms 312 and 314.

Similar to previous embodiments, screw 304 comprises a head 316 disposed on a first end 72 of a shaft 70, the shaft extending to an opposing second end 74. In some embodiments, screw 304 is substantially similar to screw 252 (FIG. 14) except that screw 304 is not self-tapping and screw head 316 is smaller than screw head 258. It is appreciated that in the present embodiment, screw 304 can alternatively be self-tapping and head 316 can be the same size or larger than head 258. Screw 304 can also be identical to screw 26 (FIG. 2).

Figure 17:
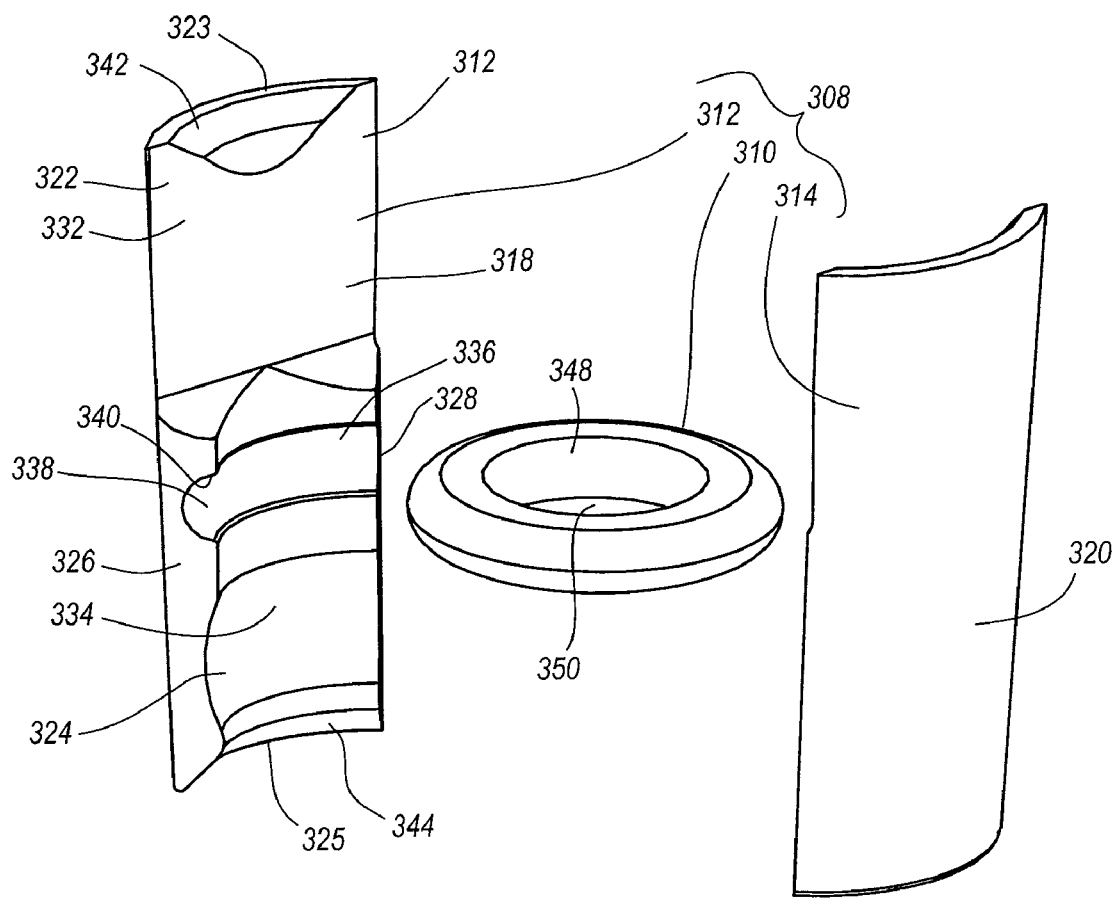
FIG. 17 is an exploded perspective view of the clamping assembly of the anchor assembly shown in FIG. 16.

Turning to FIG. 17, clamp arms 312 and 314 are substantially identical. Thus, all disclosure with regard to clamp arm 312 is also applicable to clamp arm 314. Clamp arm 312 has an interior surface 318 and an exterior surface 320 that each extends between a first end 322 and an opposing second end 324. First end 322 terminates at a first end face 323 while second end 324 terminates at a second end face 325. A first sidewall 326 and a second sidewall 328 extend between interior surface 318 and exterior surface 320 along at least a portion of the length of clamp arm 312. Exterior surface 320 is curved to substantially bias against interior surface 330 of collar 302, as explained in more detail below.

Interior surface 318 of clamp arm 312 comprises a top portion 332 at first end 322, a head retention portion 334 formed at second end 324, and a ring retention portion 336 formed therebetween. Top portion 332 of interior surface 318 is substantially flat and intersects curved exterior surface 320 on both sides of interior surface 318. Head retention portion 334 has a concave curvature extending along the length thereof and a concave curvature transversely extending across the width thereof. Ring retention portion 336 comprises a curved channel 338 defined by an edge wall 340 extending transversely between sidewalls 326 and 328, curved channel 338 being sized and shaped to receive ring 310, as discussed below. Interior surface 318 of clamp arm 312 also has a first tapered portion 342 that tapers outward from first end face 323 to top portion 332 and a second tapered portion that tapers outward from second end face 325 to head retention portion 334.

Clamp arm 312 is made so as to be able to flex at channel 338. This is typically accomplished by making clamp arm 312 out of titanium and by making clamp arm 312 thinnest at channel 338 (see FIG. 18). Although clamp arm 312 is typically made of titanium, other biocompatible metals, alloys, composites and the like can also be used.

Ring 310 functions as a fulcrum and aids in the placement and retention of clamp arms 312 and 314 within longitudinal passage 346. Ring 310 comprises an annular body 348 that encircles and bounds an opening 350 extending completely through ring 310, the ring substantially forming a toroid. Ring 310 is shaped to be received within channels 338 in clamp arms 312 and 314.

Figures 18, 19:
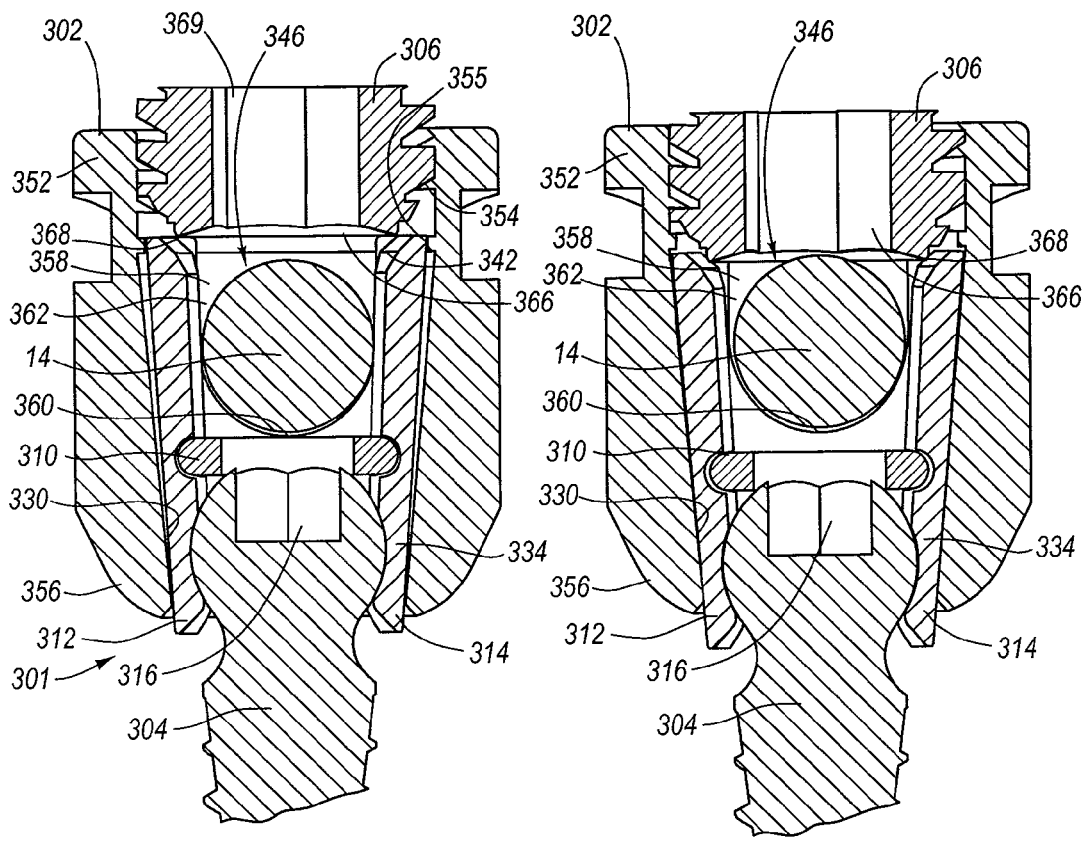
FIG. 18 is a cross sectional side view of the anchor assembly shown in FIG. 16 showing the fastener in a first position in which the fastener begins biasing against the clamping assembly.
FIG. 19 is another cross sectional side view of the anchor assembly shown in FIG. 16 showing the fastener in a second position in which the fastener biases against the clamping assembly and the head of the screw is prevented from pivoting or rotating relative to the clamping assembly.

As depicted in FIG. 18, collar 302 is substantially similar to collar 22 (FIG. 2) except that the inner longitudinal passage 346 is shaped to accommodate clamp arms 312 and 314. As such, longitudinal passage 346 differs somewhat from longitudinal passage 38. For example, internal threads 354 do not extend as far into collar 302 from first end 352 as threads 40 extend into collar 22. Interior surface 330 of collar 302 uniformly tapers inward along the length of the body from the lower end of internal threads 354 to the second end 356 of collar 302, causing longitudinal passage 346 to continuously constrict. An annular lip 355 radially inwardly projects from interior surface 300 just below internal threads 354. As discussed below, annular lip 355 functions in part as a lock to retain clamp arms 312 and 314 within collar 302. Collar 302 does not include pin hole 60 (FIG. 2) but does include a transverse passage 358 substantially similar to transverse passage 54 of collar 22, except that transverse passage 358 does not extend as far into collar 302, causing the floors 360 of the U-shaped channels 362 and 364 to be closer to first end 352 of collar 302.

Longitudinal passage 346 is sized such that it has a diameter at second end 356 of collar 302 that is less than the diameter of assembled clamping assembly 308 where the ring is disposed so as to prevent clamping assembly from being able to be removed from collar 302 through second end 356 of collar. In some embodiments, head 316 of screw 304 has a maximum diameter that is less than the minimum diameter of longitudinal passage 346 extending through second end 356 of collar 302. For these embodiments, collar 302 can be positioned over screw head 316 after screw 304 has been screwed into the vertebra, allowing the doctor more flexibility.

Fastener 306 is substantially similar to fastener 24 (FIG. 2) except that bottom end face 366 is radially inwardly tapered at the outer edge 368. Note that polygonal socket 369 can pass all the way through fastener 306, as depicted, or only part way, as it does in fastener 24.

During assembly of anchor 301, clamp arms 312 and 314 are disposed on opposite sides of ring 310 such that ring body 348 is received within channels 338 on ring retention portions 336 of each clamp arm 312 and 314. Screw 304 is then positioned so that head 316 of screw 304 is placed between clamp arms 312 and 314 so as to seat against head retention portions 334 of clamp arms 312 and 314, and shaft 70 extends outward and away from clamping assembly 308. Although head 316 is seated against head retention portions 334, there is no attachment and screw 304 is pivotable relative to clamping assembly 308.

Screw 304 and clamp arms 312 and 314 are then advanced into longitudinal passage 346 of collar 302 from first end 352 and advanced towards second end 356 with head 316 of screw 304 remaining disposed between clamp arms 312 and 314 and shaft 70 extending outward toward second end 356 of collar 302. Ring 310 keeps clamp arms 312 and 314 spaced apart from each other during assembly and allows clamp arms 312 and 314 to be at least partially disposed on opposite sides of longitudinal passage 346 of collar 302. As screw 304 and clamping assembly 308 are advanced through longitudinal passage 346 toward second end 356 of collar 302, second end 74 of shaft 70 of screw 304 extends beyond second end 356. Also, the narrowing of longitudinal passage 346 causes the exterior surfaces 320 of clamp arms 312 and 314 to substantially bias against interior surface 330 of collar 302 on opposite sides of longitudinal passage 346, while the interior surfaces 318 of clamp arms 312 and 314 bias against ring 310 at ring retention portions 336. This prevents clamping assembly 308 from passing completely through longitudinal passage 346 at second end 356 of collar 302 while still allowing shaft 70 of screw 304 to extend beyond second end 356.

The biasing of clamp arms 312 and 314 against ring 310 and interior surface 330 of collar 302 also causes head retention portions 334 of clamp arms 312 and 314 to further engage opposite sides of head 316, thereby clamping head 316 between clamp arms 312 and 314 and preventing screw 304 from disengaging from clamping assembly 308. In this configuration the clamping action of clamping assembly 308 is such as to allow collar 302 to be pivotable about head 316 of screw 304. Any attempts to draw screw 304 out of clamping assembly 308 by pulling on second end 74 of shaft 70 causes clamp arms 312 and 314 to be drawn further toward second end 356 of collar 302 within longitudinal passage 346. Because longitudinal passage 346 tapers inwardly towards second end 356, clamp arms 312 and 314 are pushed inward towards each other, which causes head retention portions 334 to further engage head 316, thereby preventing head 316 from disengaging from clamp arms 312 and 314.

Figure 20:
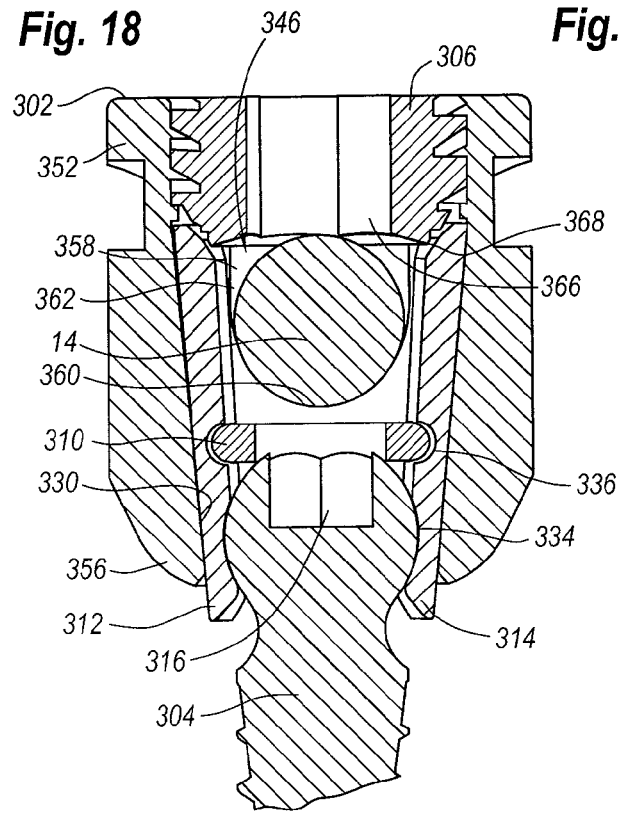
FIG. 20 is another cross sectional side view of the anchor assembly shown in FIG. 16 showing the fastener in a third position in which the fastener biases against the stabilizing rod.

A method of inserting and using anchor 301 is now described and depicted in FIGS. 18-20.

Initially, anchor 301 is mounted onto a vertebra in a similar manner to previous embodiments discussed above, using a driver or other type of attaching mechanism to secure screw 304 within a hole in the vertebra. Methods and drivers discussed previously can also be used with anchor 301.

After anchor 301 has been secured to a vertebra, rod 14 is received within transverse passage 358 of collar 302. Because collar 302 can pivot about head 316 of screw 304, collar 302 can be pivoted to allow correct alignment of collar 302 to rod 14.

Once stabilizing rod 14 is positioned within transverse passage 358 of collar 302, fastener 306 is positioned at first end 352 of collar 302, similar to previous embodiments discussed above, and screwed into first end 352 of collar 302. As fastener 306 is screwed down into first end 352, fastener 306 comes to a first position, as depicted in FIG. 18, at which edge portion 368 of bottom end face 366 comes into contact with first tapered portion 342 of both clamp arms 312 and 314. When fastener 306 is at this first position, collar 302 remains pivotable about head 316 of screw 304 and rod 14 is movable and rotatable within transverse passage 358.

As fastener 306 is further screwed into first end 352, fastener 306 continues to bias against clamp arms 312 and 314, pushing clamp arms 312 and 314 further towards second end 356 of collar 302. Because longitudinal passage 346 tapers inwardly towards second end 356, clamp arms 312 and 314 are pushed inward with more force, which causes head retention portions 334 to further engage and clamp head 316 of screw 304. At a certain point before fastener 306 comes into contact with rod 14, fastener 306 comes to a second position, as depicted in FIG. 19, at which the clamping force between head retention portions 334 of clamp arms 312 and 314 is sufficient to fixedly secure screw 304 to clamping assembly 308 and the outward force exerted by clamp arms 312 and 314 causes clamp arms 312 and 314 to be fixedly secured to collar 302. Thus, when fastener 306 is at this second position, collar 302 is fixedly secured to screw 304 and thus prevented from rotating or pivoting relative to screw 304 under reasonable force. However, rod 14 can still be freely moved and rotated within transverse passage 358.

Although in the foregoing discussion rod 14 is inserted into transverse passage 358 before fastener 306 is attached to collar 302, it is appreciated that fastener 306 alternatively can be attached to collar 302 before rod 14 is inserted into transverse passage 358. In fact, in some embodiments rod 14 can be inserted even after collar 302 has been secured to screw 304.

As fastener 306 is further screwed into first end 352 of collar 302, edge portion 368 of bottom end face 366 further pushes against clamp arms 312 and 314. At a certain point, however, clamp arms 312 and 314 are prevented from moving further toward second end 356 of collar 302 due to the sloping of interior surface 330 of collar 302. To allow fastener 306 to be further screwed into first end 352 of collar 302, the upper end of clamp arms 312 and 314, that have now passed annular lip 355, flex outwardly toward interior surface 330 as edge portion 368 of fastener 306 pushes against first tapered portions 342. This may occur before or after screw 304 is secured to clamp arms 312 and 314. Lip 355 can thus function as a lock to prevent unwanted removal of claim arms 312 and 314.

Eventually, fastener 306 comes to a third position, as depicted in FIG. 20, at which at least a portion of bottom end face 366 biases stabilizing rod 14 against floors 360 of channels 362 and 364 of transverse passage 358. When fastener 306 is at this third position, stabilizing rod 14 is secured from unwanted movement by being compressed between fastener 306 and floors 360 of collar 302. Thus, at the third position, the anchor assembly is rigidly interconnected and rigidly secured to rod 14. Note that as opposed to previous embodiments, the fastener 306 does not bias rod 14 against screw 304.

The depicted embodiment offers a significant advantage over current anchor systems. There are times that a doctor desires to further separate or bring together vertebrae that have been crushed or otherwise affected. Using anchor assemblies according to the depicted embodiment, this can easily be accomplished. Once screws 304 have been attached to different vertebrae and collars 302 have been secured to respective screws 304, corresponding rigid anchor assemblies 300 can be moved longitudinally along rod 14 relative to each other. This is easily done using the depicted embodiment because each vertebra and correspondingly attached anchor assembly 300 can be moved as a solid, secure unit before anchor assembly 300 is secured to rod 14. Once a plurality of anchor assemblies 300 are in desired positions, each anchor assembly 300 is then secured to rod 14 by screwing fastener 306 further into longitudinal passage 346, as described above. Thus, this double securing system can be performed using a single fastener 306.

Figure 21:
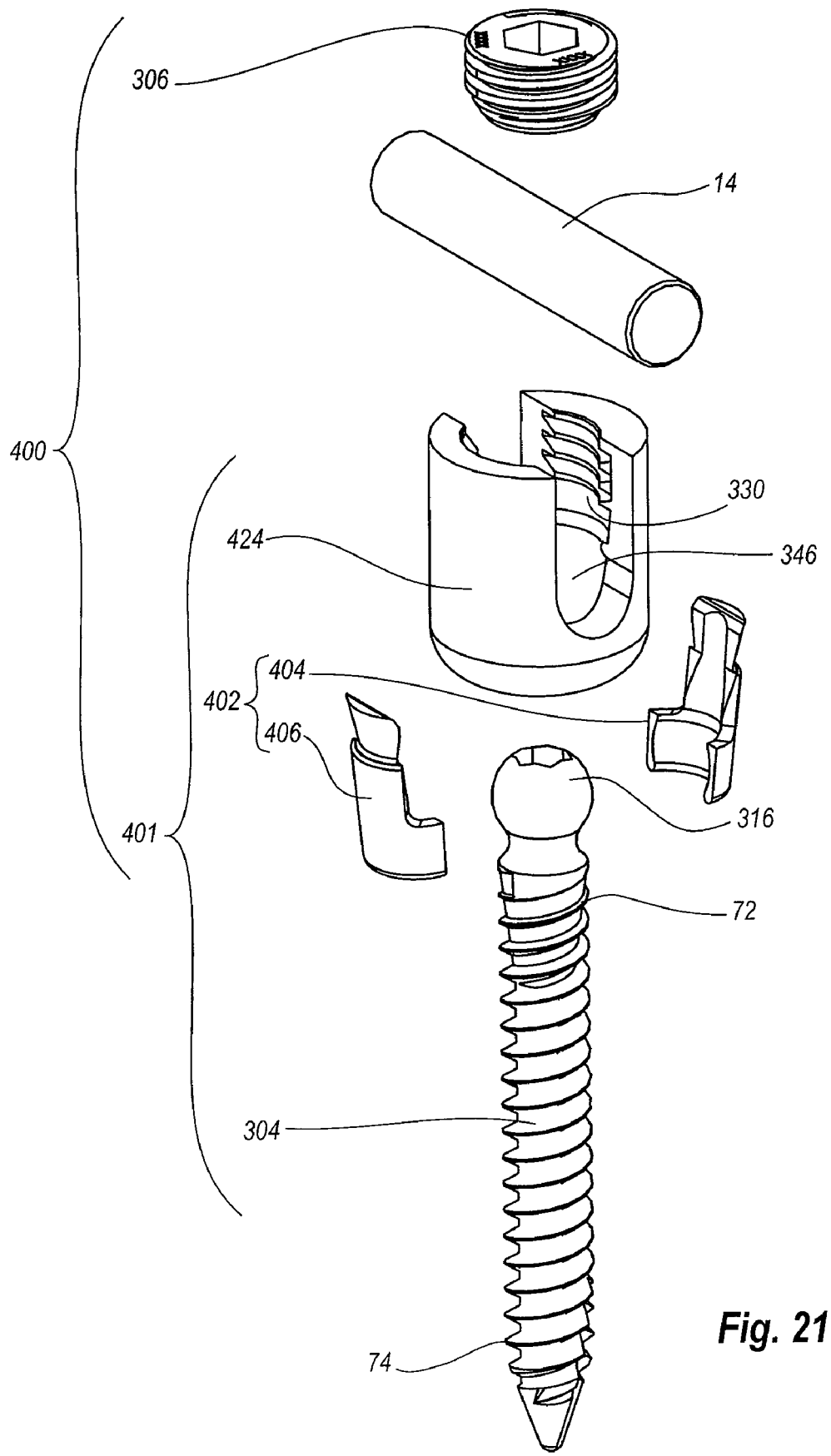
FIG. 21 is an exploded perspective view of another alternative embodiment of an anchor assembly that uses an alternative clamping assembly.

Depicted in FIG. 21 is an alternative embodiment of an anchor assembly 400 which also uses a clamping assembly to secure the collar to the screw and prevent the collar from moving with respect to the screw while allowing the rod to freely rotate and move transversely within the transverse passage. Common features between anchor assembly 400 and anchor assembly 300 are identified by like reference characters. Similar to anchor assembly 300, anchor assembly 400 comprises an anchor 401 on which a fastener 306 selectively engages. Similar to anchor 301, anchor 401 comprises a collar 424, a screw 304 and a clamping assembly 402 having a pair of spaced apart clamp arms 404 and 406. However, unlike clamping assembly 308 clamping assembly 402 does not have a ring.

Figure 22:
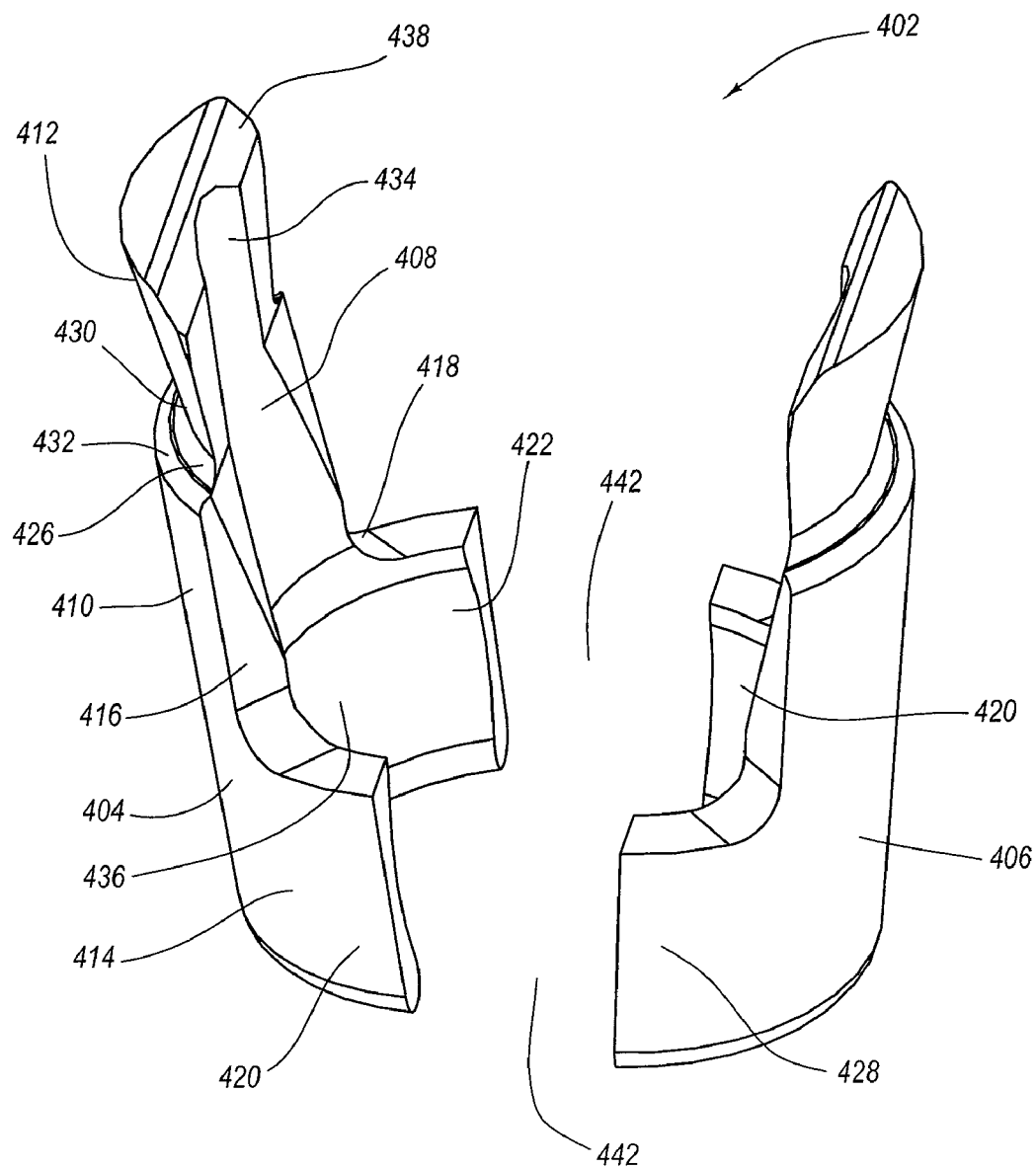
FIG. 22 is an exploded perspective view of the clamping assembly of the anchor assembly shown in FIG. 21.

Turning to FIG. 22, discrete clamp arms 404 and 406 are substantially identical. Thus, all disclosure with regard to clamp arm 404 is also applicable to clamp arm 406. Clamp arm 404 has an interior surface 408 and an exterior surface 410 that each extend between a first end 412 and an opposing second end 414. A first sidewall 416 and a second sidewall 418 extend between interior surface 408 and exterior surface 410 along at least a portion of the length of clamp arm 404. At second end 414, clamp arm 404 has a first extension 420 and a second extension 422 which annularly extend further out from opposite sides of clamp arm 404.

Figure 23:
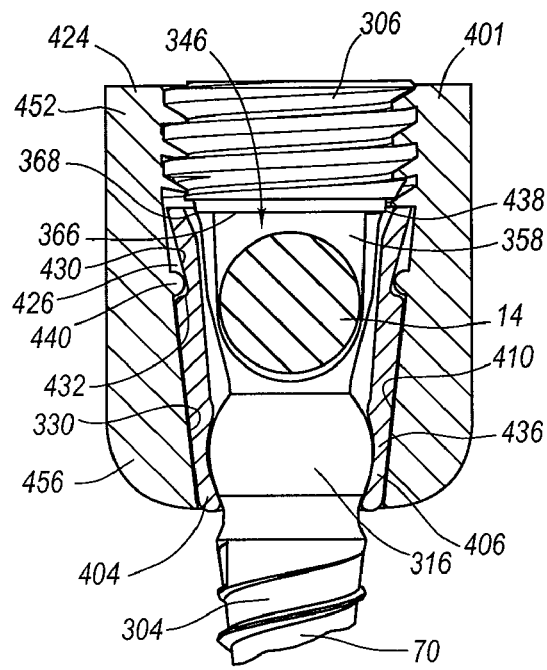
FIG. 23 is a cross sectional side view of the anchor assembly shown in FIG. 21 showing the fastener in a first position in which the fastener begins biasing against the clamping assembly.

Exterior surface 410 is curved to substantially bias against interior surface 330 of collar 424, as explained in more detail below. An annular channel 426 is formed on exterior surface 410, extending transversely between sidewalls 416 and 418. Channel 426 is bound by an upper sidewall 430 and a lower sidewall 432 that protrude into exterior surface 410 and meet at the deepest portion of channel 426. Upper sidewall 430 is disposed nearer to first end 412 than lower sidewall 432. As shown in FIG. 23, lower sidewall 432 is shorter and has a steeper angle than upper sidewall 430 with respect to the exterior surface 410, thus forming a substantial "L" cross-sectional shape.

Returning to FIG. 22, interior surface 408 of clamp arm 404 comprises a top portion 434 disposed at first end 412 and a head retention portion 436 formed at second end 414. Similar to head retention portion 334 of interior surface 318 of clamp arm 312 (FIG. 17), head retention portion 436 has a concave curvature extending along the length thereof and a concave curvature transversely extending across the width thereof. Head retention portion 436 includes extensions 420 and 422, so head retention portion 436 has a larger surface area than head retention portion 334. Interior surface 408 also has a first tapered portion 438 substantially similar to first tapered portion 342 of clamp arm 312, formed at first end 412 that slopes radially outward.

Similar to clamp arm 312, clamp arm 404 is designed to be able to flex. This flexing is designed to occur at the thinnest part of clamp arm 404. As shown in FIG. 23, clamp arm 404 is thinnest where channel 426 protrudes into the exterior surface 410 thereof. As such, the flexing of clamp arm 404 is designed to occur at channel 426. As with clamp arm 312, clamp arm 404 is typically made out of titanium but other materials approved for use in the human body can alternatively be used.

As depicted in FIG. 23, collar 424 is substantially similar to collar 302 except that collar 424 has a single uniform taper inward extending along the length of the body from the lower end of internal threads 354 to the second end 356 of collar 424. Collar 424 also includes an annular ring 440 formed on interior surface 330 that at least partially encircles longitudinal passage 346. Annular ring 440 is positioned on interior surface 330 such that ring 440 can be generally received within channel 426 on clamp arms 404 and 406.

Assembly of anchor 401 occurs in much the same manner as detailed above with regard to anchor 301, with some differences. During assembly, clamp arms 404 and 406 are placed opposite each other. Screw 304 is positioned so that head 316 of screw 304 is placed between clamp arms 404 and 406 so as to seat against head retention portions 436 of clamp arms 404 and 406, and shaft 70 extends outward and away from clamping assembly 402. Gaps 442 are formed between clamp arms 404 and 406 between respective extensions 420 and 422 of each clamp arm (see FIG. 22). Similar to anchor 301, screw 304 is pivotable relative to clamping assembly 402.

Screw 304 and clamp arms 404 and 406 are advanced into longitudinal passage 346 of collar 424 from first end 352 and advanced towards second end 356 with head 316 of screw 304 remaining disposed between clamp arms 404 and 406 and shaft 70 extending outward toward second end 356 of collar 302. As screw 304 and clamp arms 404 and 406 are advanced through longitudinal passage 346 toward second end 356, second end 74 of shaft 70 of screw 304 extends beyond second end 356, and exterior surfaces 410 of clamp arms 404 and 406 bias against annular ring 440 of collar 424, and are pushed inward. At a certain point, channels 426 of clamp arms 404 and 406 align with annular ring 440 of collar 424. When this occurs, the outward force of clamp arms 404 and 406 on interior surface 330 of collar 424 causes clamp arms 404 and 406 to snap outwardly when annular ring 440 is received within channels 426 of clamp arms 404 and 406.

As screw 304 and clamping assembly 402 are further advanced through longitudinal passage 346 toward second end 356 of collar 424, the narrowing of passage 346 causes the exterior surfaces 410 of clamp arms 404 and 406 to substantially bias against interior surface 330 of collar 424 on opposite sides of longitudinal passage 346. This prevents clamping assembly 402 from passing completely through passage 346 at second end 356 of collar 424 while still allowing shaft 70 of screw 304 to extend beyond second end 356. Annular ring 440 prevents clamp arms 404 and 406 from being removed from the opposite end of collar 424.

The biasing of clamp arms 404 and 406 against interior surface 330 of collar 424 also causes head retention portions 436 of clamp arms 404 and 406 to further engage opposite sides of head 316, thereby clamping head 316 between clamp arms 404 and 406 and preventing screw 304 from disengaging from clamping assembly 402. There still remains a gap 442 (FIG. 22) between extensions 420 and 422, so as not to hamper the clamping action. Gap 442 is about 20/1000" when head 316 is snugly clamped between clamp arms 404 and 406. In this configuration the clamping action of clamping assembly 402 is such as to allow collar 424 to be pivotable about head 316 of screw 304. Similar to clamping assembly 308, any attempts to draw screw 304 out of clamping assembly 402 causes clamp arms 404 and 406 to be drawn further toward second end 356 of collar 424 within longitudinal passage 346. Because longitudinal passage 346 uniformly tapers inwardly towards second end 356, clamp arms 404 and 406 are pushed further inward, which causes head retention portions 436 to further engage head 316, thereby preventing screw 304 from disengaging from clamp arms 404 and 406.

Figure 24:
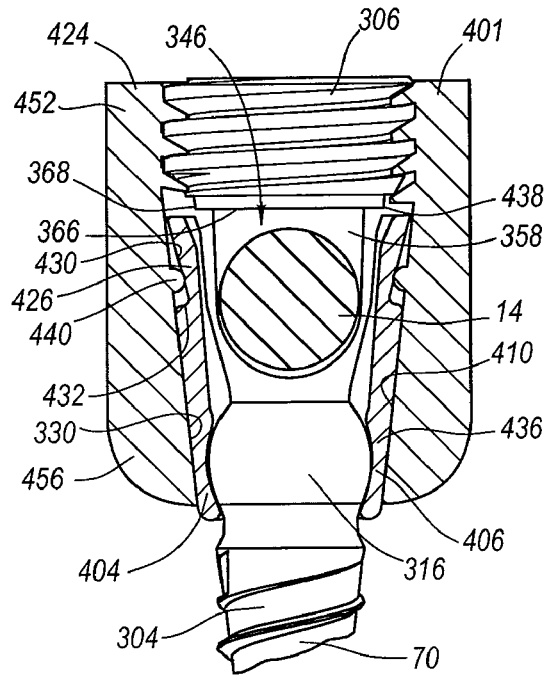
FIG. 24 is another cross sectional side view of the anchor assembly shown in FIG. 21 showing the fastener in a second position in which the fastener biases against the clamping assembly and the head of the screw is prevented from pivoting or rotating relative to the clamping assembly.
Figure 25:
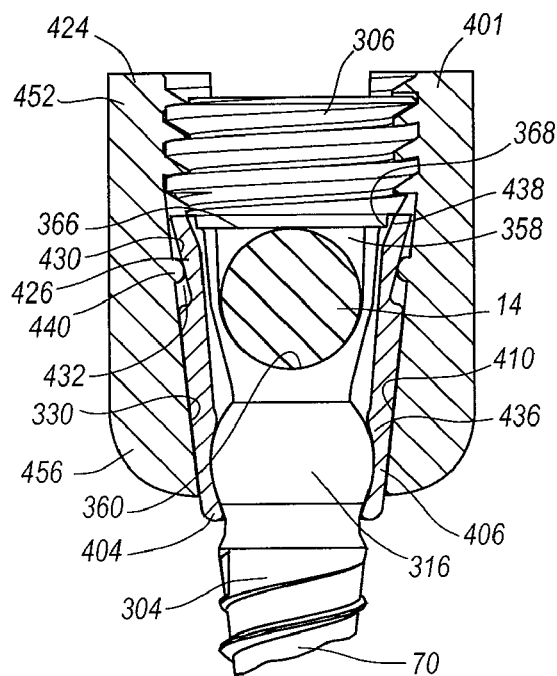
FIG. 25 is another cross sectional side view of the anchor assembly shown in FIG. 21 showing the fastener in a third position in which the fastener biases against the stabilizing rod

A method of inserting and using anchor 401 is now described and depicted in FIGS. 23-25. Inserting and using anchor 401 occurs in much the same manner as with anchor 301 detailed above.

Initially, anchor 401 is mounted onto a vertebra in a similar manner to anchor 301. Methods and drivers discussed previously can also be used with anchor 401.

Similar to anchor assembly 300, after head 316 of screw 304 is seated within clamping assembly 402, rod 14 is received within transverse passage 358 of collar 424. Because collar 424 can pivot about head 316 of screw 304, collar 424 can be pivoted to allow correct alignment of collar 424 to rod 14.

Screw 304 is secured to clamping assembly 402 in substantially the same manner as discussed above regarding clamping assembly 308. Once stabilizing rod 14 is positioned within transverse passage 358 of collar 424, fastener 306 is positioned at first end 352 of collar 424 and screwed into first end 352. As fastener 306 is screwed down into first end 352, fastener 306 comes to a first position, as depicted in FIG. 23, at which edge portion 368 of bottom end face 366 comes into contact with first tapered portion 438 of both clamp arms 404 and 406. When fastener 306 is at this first position, collar 424 remains pivotable about head 316 of screw 304 and rod 14 is movable and rotatable within transverse passage 358.

As fastener 306 is further screwed into first end 352, fastener 306 continues to bias against clamp arms 404 and 406, pushing clamp arms 404 and 406 further towards second end 356 of collar 424. Because longitudinal passage 346 uniformly tapers inwardly towards second end 356, clamp arms 404 and 406 are pushed inward with more force, which causes head retention portions 436 to further engage and clamp head 316 of screw 304. At a certain point before fastener 306 comes into contact with rod 14, fastener 306 comes to a second position, as depicted in FIG. 24, at which the clamping force between head retention portions 436 of clamp arms 404 and 406 is sufficient to fixedly secure screw head 316 to clamping assembly 402 and the outward force exerted by clamp arms 404 and 406 causes clamp arms 404 and 406 to be fixedly secured to collar 424. Thus, when fastener 306 is at this second position, collar 424 is fixedly secured to screw 304 and prevented from rotating or pivoting relative to screw 304, while rod 14 can still be moved and rotated within transverse passage 358.

As with anchor assembly 300, rod 14 can be inserted into transverse passage 358 either before or after fastener 306 is attached to collar 424.

Collar 424 is secured to rod 14 using fastener 306 in substantially the same manner as discussed above regarding collar 302. As fastener 306 is screwed further into first end 352 of collar 424, edge portion 368 of bottom end face 366 further pushes against clamp arms 404 and 406. At a certain point, however, clamp arms 404 and 406 are prevented from moving further toward second end 356 of collar 424 due to the sloping interior surface 330 of collar 424. To allow fastener 306 to be further screwed into first end 352 of collar 424, clamp arms 404 and 406 flex outward at the point where channel 426 is narrowest as edge portion 368 of bottom end face 366 pushes against first tapered portions 438. This may occur before or after screw 304 is secured to clamp arms 404 and 406. Eventually, fastener 306 comes to a third position, as depicted in FIG. 25, at which at least a portion of bottom end face 366 biases stabilizing rod 14 against floors 360 of channels 362 and 364 of transverse passage 358. When fastener 306 is at this third position, stabilizing rod 14 is secured from unwanted movement by being compressed between fastener 306 and floors 360 of collar 424. Thus, at the third position, the anchor assembly is rigidly interconnected and rigidly secured to the rod. Similar to anchor assembly 300, the fastener does not bias the rod against the screw.

Similar to anchor assembly 300, anchor assembly 400 is designed so that individual anchor assemblies 400 can be moved longitudinally along rod 14 relative to each other after corresponding collars 424 have been secured to screws 304 so that a doctor may further separate or bring together vertebrae that have been crushed or otherwise affected. Once a plurality of anchor assemblies 400 are in desired positions, each anchor assembly 400 is then secured to rod 14 by screwing fastener 306 further into longitudinal passage 346, as described above.

Figure 26:
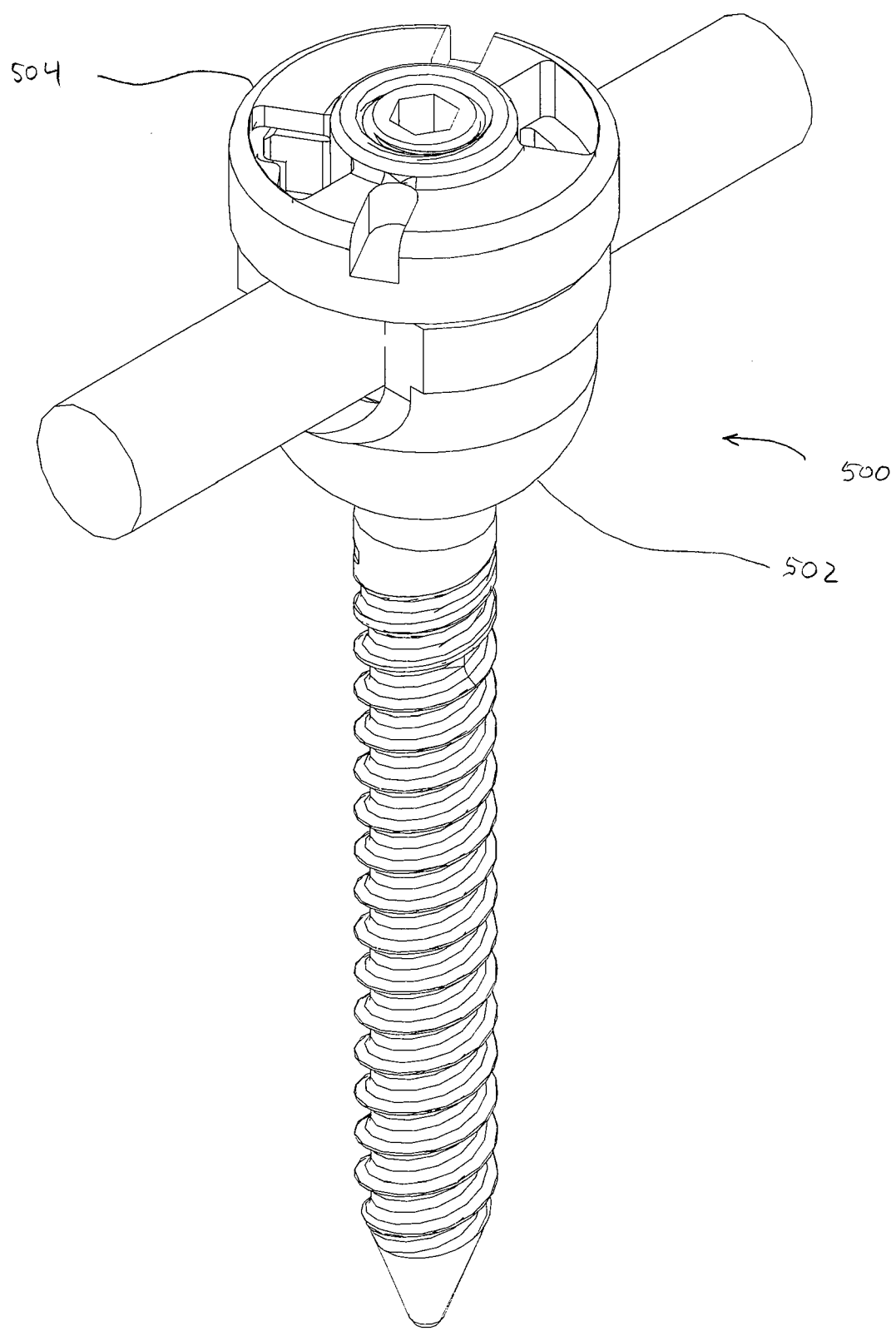
FIG. 26 is a perspective view of another alternative embodiment of an anchor assembly.
Figure 27:
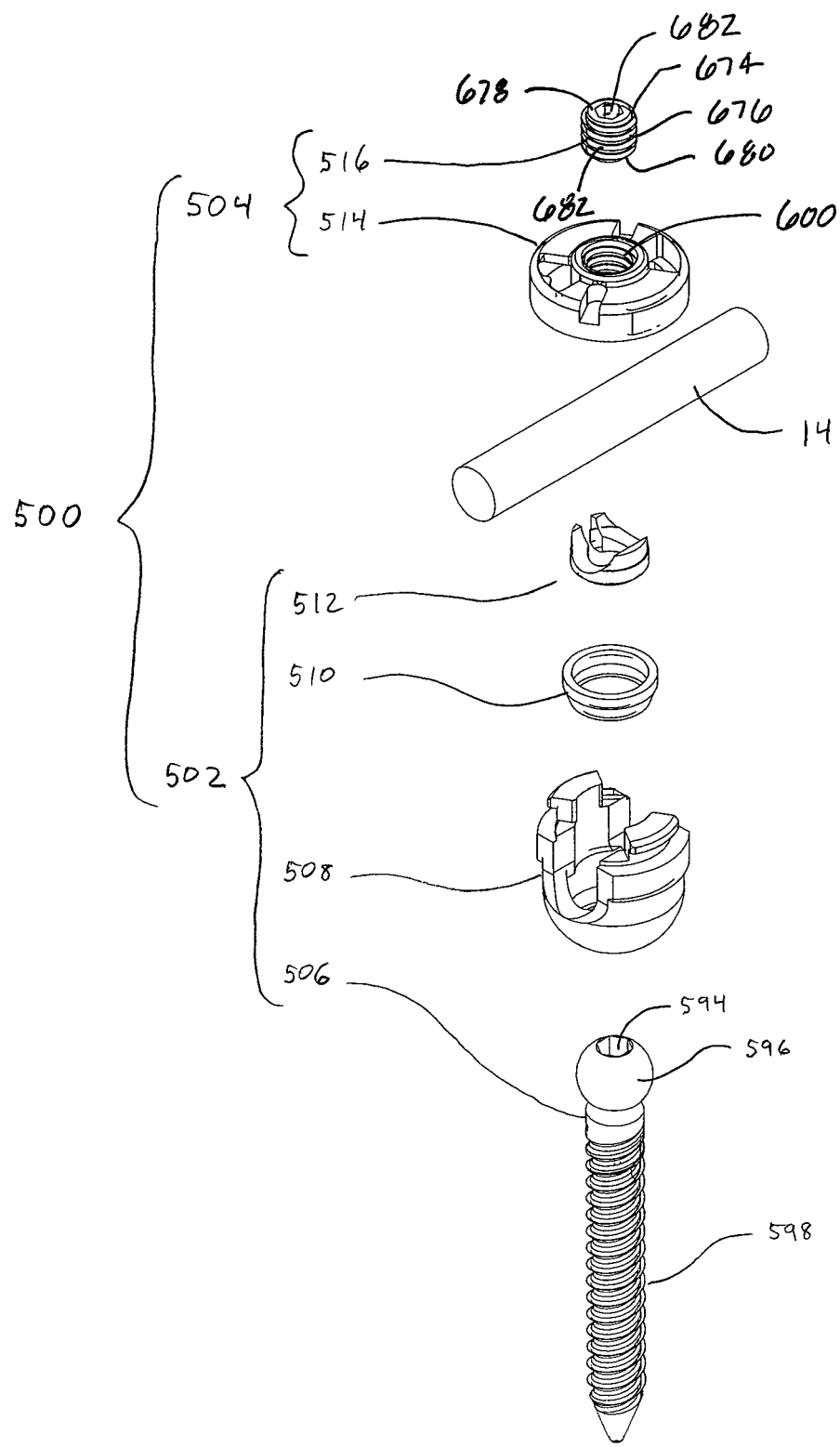
FIG. 27 is an exploded perspective view of the anchor assembly shown in FIG. 26.

Depicted in FIG. 26 is another alternative embodiment of an anchor assembly 500 incorporating features of the present invention. Like elements between previously described anchor assemblies and anchor assembly 500 are identified by like reference characters. Similar to previously described anchor assemblies, anchor assembly 500 comprises an anchor 502 on which a cap assembly 504 selectively engages. As shown in FIG. 27, anchor 502 comprises an elongated screw 506, a collar 508 pivotally mounted on screw 506, and a locking ring 510 and a collet 512, both received within collar 508. Cap assembly 504 comprises a locking cap 514 adapted to be attached to collar 508 and a fastener 516 adapted to be threaded into locking cap 514, as described in further detail below.

Figure 28:
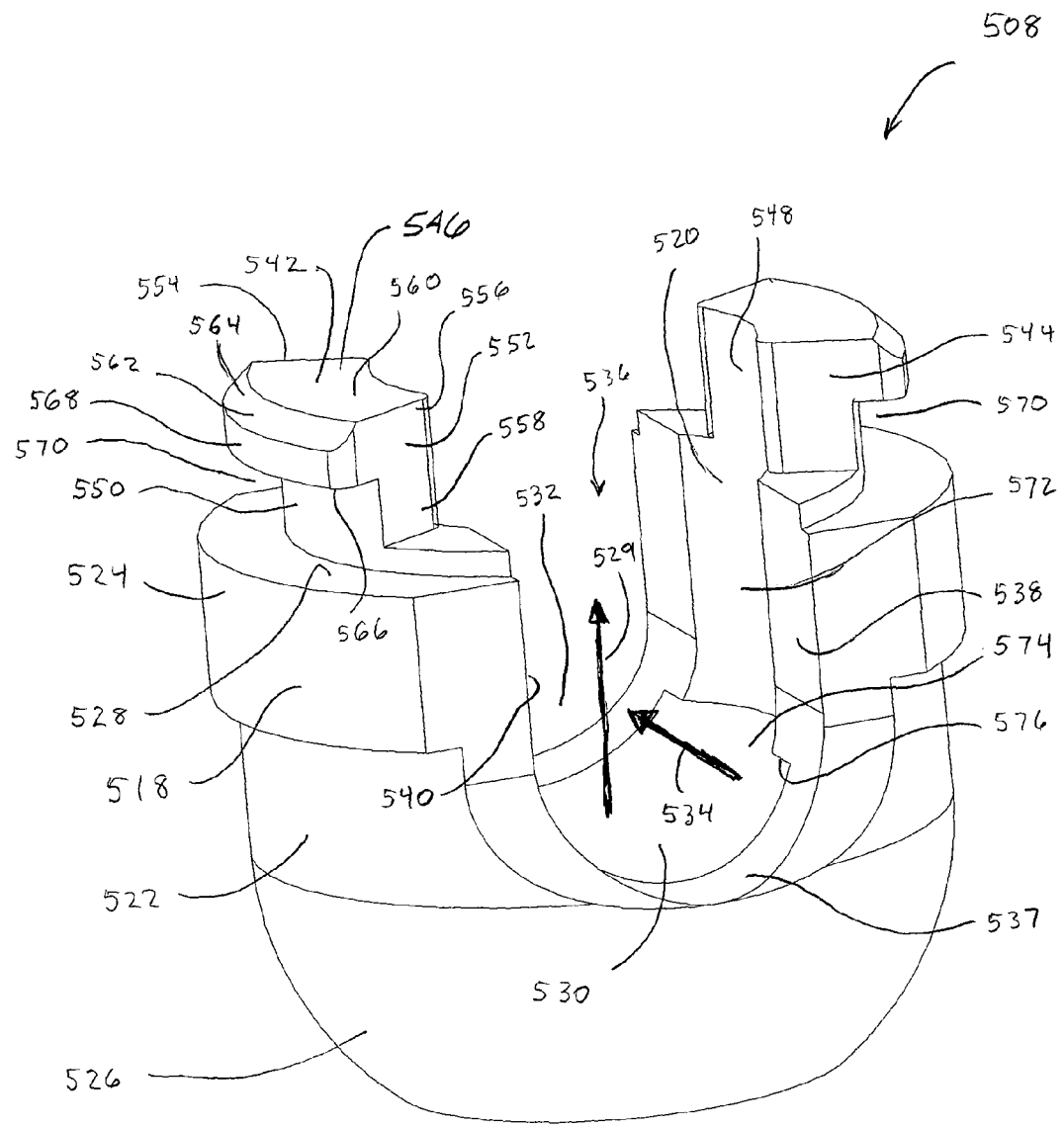
FIG. 28 is a top perspective view of the collar of the anchor assembly shown in FIG. 26.

As depicted in FIG. 28 and similar to collar 22, collar 508 comprises a tubular side wall 518 having an interior surface 520 and an exterior surface 522 that each extend between a first end 524 and an opposing second end 526. First end 524 terminates at a terminal end face 528. Interior surface 520 bounds a longitudinal passage (denoted by arrow 529) that longitudinally extends through collar 508.

Figure 29:
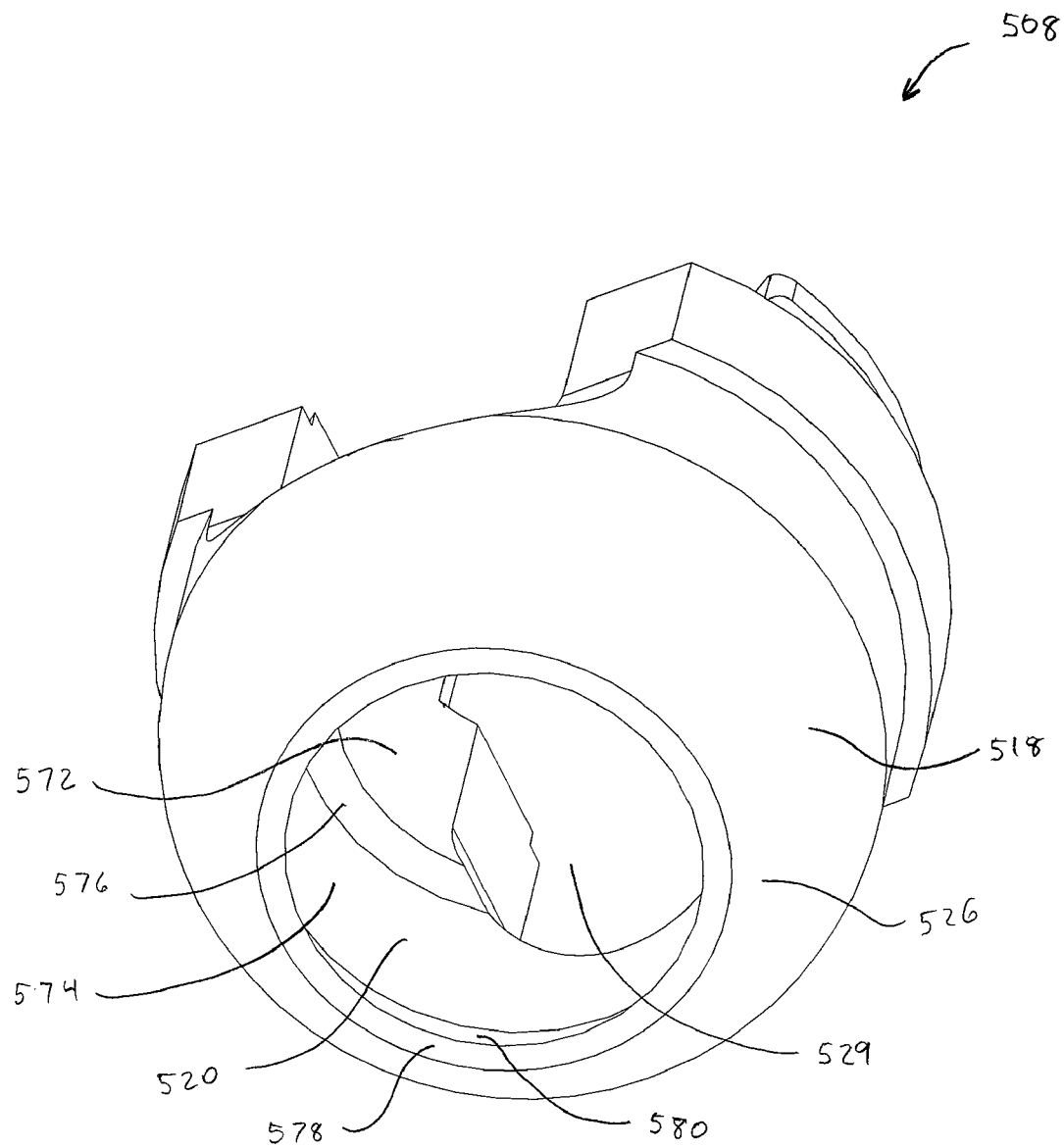
FIG. 29 is a bottom perspective view of the collar shown in FIG. 28.

Turning to FIG. 29 in conjunction with FIG. 28, as opposed to collar 22 in which interior surface 30 is a substantially contiguously smooth surface from first end 34 to second end 36, interior surface 520 comprises a first section 572 that extends from first end 524 towards second end 526 and a second section 574 that extends from second end 526 towards first end 524 and is recessed further away from longitudinal passage 529. Because of the recession of second section 574, a ledge 576 is formed between the two sections where the two sections overlap. Ledge 576 lies in a plane that is substantially orthogonal to the direction of longitudinal passage 529. See also FIG. 33 for a cross-sectional view of first section 572, second section 574, and ledge 576.

Returning to FIG. 28, as opposed to collar 22, exterior surface 522 of collar 508 has a substantially circular transverse cross section. It is appreciated, however, that exterior surface 522 can alternatively be substantially polygonal, similar to previously described embodiments, substantially ovoid, or can be a combination of these shapes. Other shapes can also be used.

Side wall 518 is formed having a pair of channels 530 and 532 which are substantially similar to channels 42 and 44 of collar 22 (FIG. 2). As such, channels 530 and 532 are disposed on opposing sides of side wall 518 and transversely extend through side wall 518 forming a transverse passage (denoted by arrow 534). In the embodiment depicted, channels 530 and 532 each have a substantially U-shaped configuration, but as discussed with regard to channels 42 and 44, other configurations can be used. Each channel 530 and 532 has an open mouth 536 that extends through end face 528 and an opposing floor 537 that is rounded. Similar to channels 42 and 44, each channel 530 and 532 is configured so that stabilizing rod 14 can be received therein. Each of channels 530 and 532 are bounded by opposing side surfaces 538 and 540. Similar to channels 42 and 44, side surfaces 538 and 540 can be in substantially parallel alignment or not, as discussed previously. Channels 538 and 540 form a portion of transverse passage 534 so as to intersect with the longitudinal passage 529 that also extends through collar 508.

A pair of bayonet prongs 542 and 544 extend longitudinally away from first end 524 of collar 508 on each side of transverse passage 534, respectively. Bayonet prongs 542 and 544 are configured to engage with corresponding bayonet slots 648 and 650 formed on locking cap 514 so as to provide a removably secure connection between locking cap 514 and collar 508, as discussed below. Bayonet prongs 542 and 544 are substantially similar. Thus, all disclosure with regard to bayonet prong 542 is also applicable to bayonet prong 544.

Bayonet prong 542 comprises a body 546 having an interior surface 548 and an exterior surface 550 that each extend between a pair of side walls 552 and 554 and between a first end 556 and an opposing second end 558. First end 556 terminates at a terminal end face 560, and second end 558 couples with collar 508. In the embodiment depicted, interior surface 548 of bayonet prong 542 longitudinally and transversally aligns with interior surface 520 at first end 524 of collar 508 and matches the curvature of interior surface 520 at first end 24 of collar 508. As such, interior surface 548 can be thought of as simply an extension of interior surface 520. It is appreciated that in other embodiments, interior surface 548 may not align with interior surface 520, but instead may be offset from interior surface 520. For example interior surface 548 may be offset transversally so that a shoulder is formed between interior surface 548 and interior surface 520.

A tab 562 transversally extends outward from exterior surface 550 of body 546 at or near first end 556. Tab 562 has a first surface 564 and an opposing second surface 566 which extend from exterior surface 550 to an end surface 568. Second surface 566 of tab 562, external surface 550 of body 546, and end face 528 of collar 508 bound a channel 570 into which a portion of locking cap 514 can be inserted and secured, as described in detail below.

Returning to FIG. 29, collar 508 further comprises a shoulder 578 that radially inwardly projects from second end 526 of side wall 518 so as to encircle longitudinal passage 529, similar to collar 22. Shoulder 578 has a tapered interior surface that forms an annular seat 580. See also FIG. 33 for a cross-sectional view of collar 508 showing shoulder 578 and seat 580.

Figure 30:
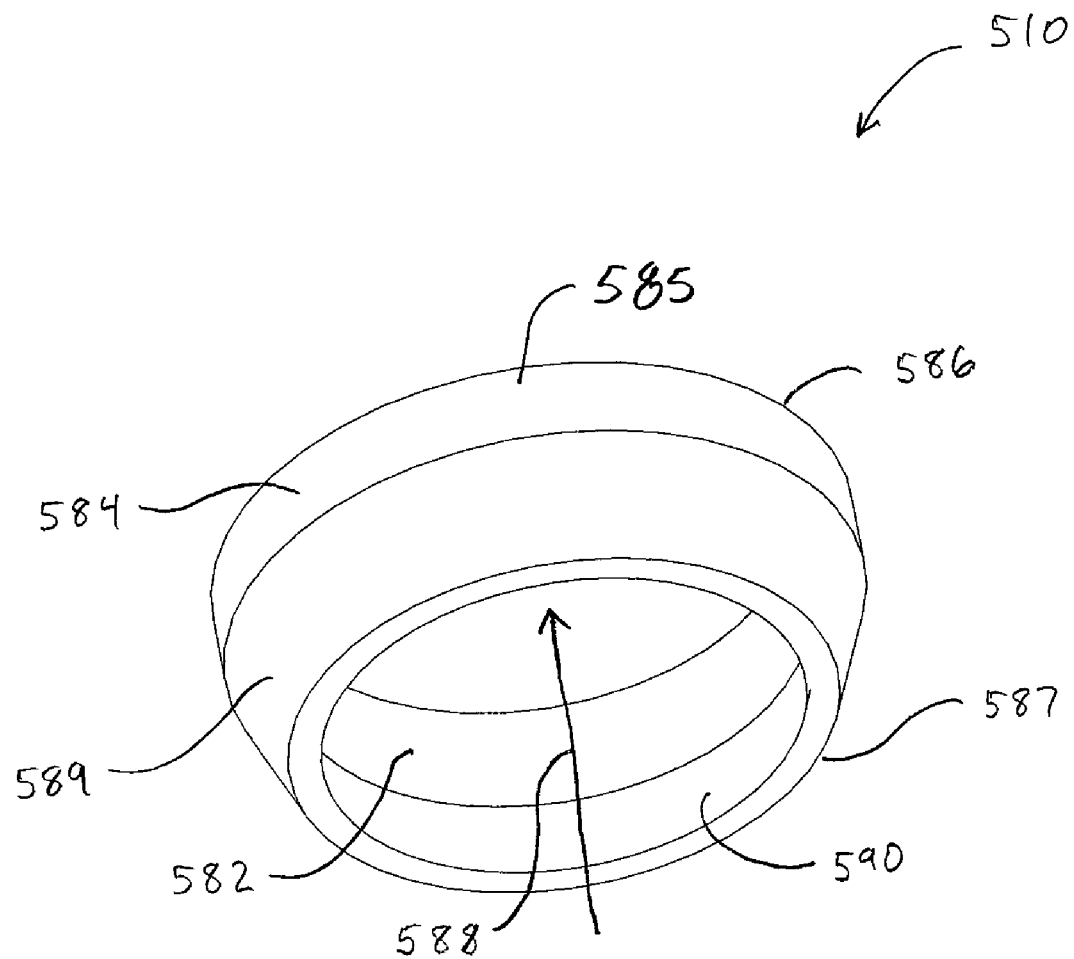
FIG. 30 is a bottom perspective view of a locking ring of the anchor assembly shown in FIG. 26.

As depicted in FIG. 30, Locking ring 510 is ring-shaped and has an interior surface 582 and an exterior surface 584 that each extend between a first end 586 and an opposing second end 587. Interior surface 582 and exterior surface 584 each have a substantially circular transverse cross section. Interior surface 582 of locking ring 510 bounds a longitudinal passage (denoted by arrow 588) that longitudinally extends through locking ring 510.

Locking ring 510 can further be defined as comprising an annular ring shaped body 585 having an annular constricting shoulder 589 that downwardly and radially inwardly projects from the lower end of body 585. Shoulder 589 has a tapered interior surface that forms an annular seat 590. As will be discussed below in greater detail, when assembled, a portion of screw 506 rests against seat 590 of locking ring 510, and a portion of exterior surface 584 of locking ring 510 rests against seat 580 of collar 508 so that collar 508 can pivot relative to screw 506. See also FIG. 33 for a cross-sectional view of locking ring 510 showing shoulder 589 and seat 590.

Returning to FIG. 27, screw 506 is substantially similar to screw 252 shown in FIG. 14, except that socket 594 is smaller than socket 260 and not recessed in head 596 and helical threads 598 are not self-tapping. It is appreciated that many of the attributes of the other screws described previously alternatively can be used in screw 506. For example, threads 598 can have a variety of different pitches and configurations, and, if desired, can be self-tapping. Similar to socket 260, socket 594 is formed on the top end of head 596 and has a polygonal shape. In some embodiments, socket 594 is sized smaller than socket 260. One benefit of this is that if desired, a tightening tool (not shown) can be inserted through a hole 600 of locking cap 514 (FIG. 34) while locking cap 514 is secured to collar 508 and tighten or loosen screw 506 before fastener 516 is inserted into hole 600 and before rod 14 is received within collar 508, as described below.

It is appreciated that if the functionality of inserting a tool through hole 600 to tighten or loosen screw 506 is not desired, socket 560 can be the same size as socket 260 or can be other sizes. It is also appreciated that many of the heads of previously described embodiments can alternatively be used as head 596. For example, head 258 of screw 252 can be used as head 596.

Figure 31:
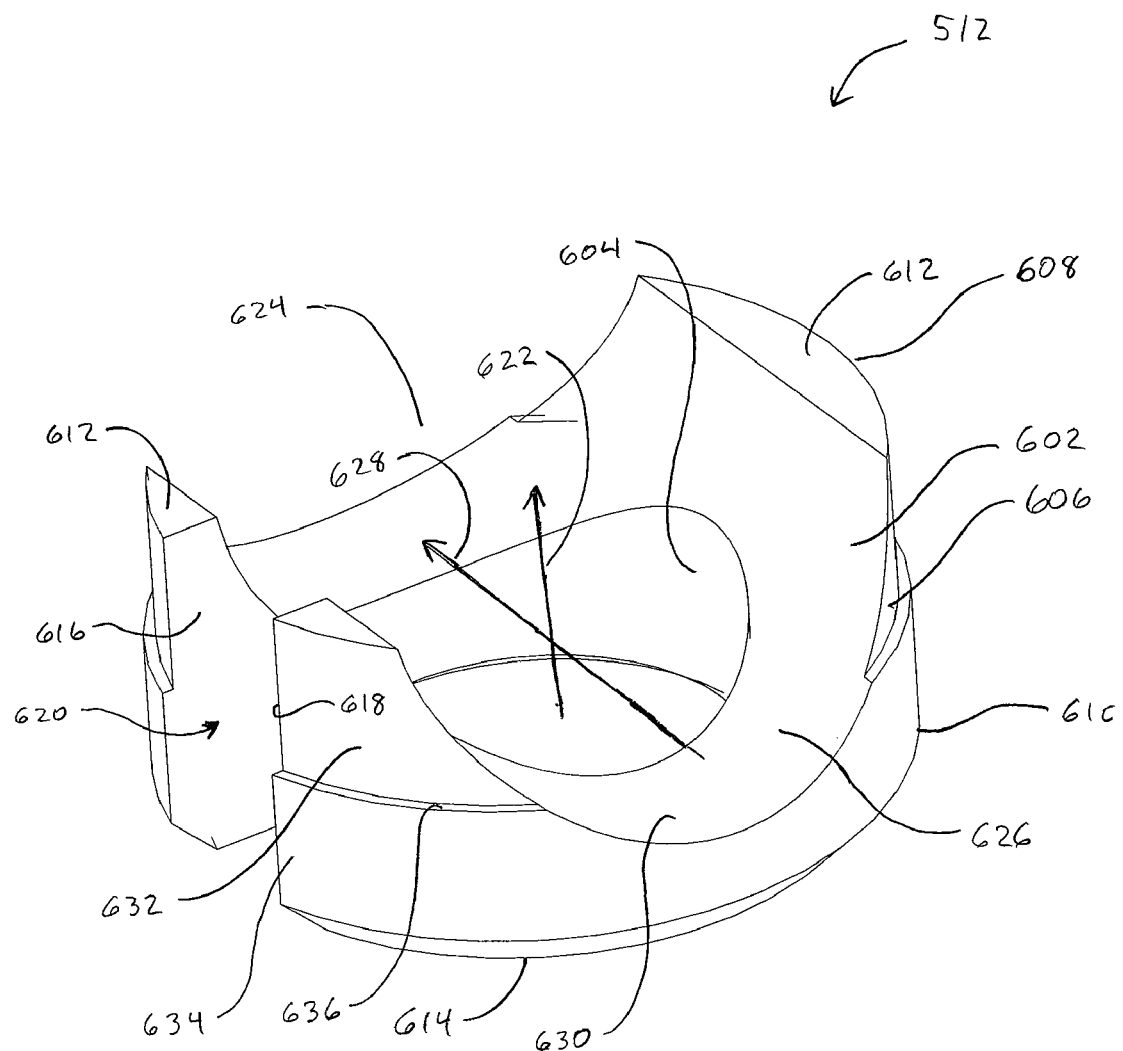
FIG. 31 is a top perspective view of a collet of the anchor assembly shown in FIG. 26.

Turning to FIG. 31, collet 512 comprises a tubular side wall 602 having an interior surface 604 and an exterior surface 606 that each extend between a first end 608 and an opposing second end 610. First end 608 terminates at a first end face 612 and second end 610 terminates at second end face 614. In the embodiment depicted, collet 512 has a c-shaped transverse cross section with interior surface 604 and exterior surface 606 extending annularly between a first side face 616 and a second side face 618. Side faces 616 and 618 extend between first end face 612 and second end face 614 and between interior surface 604 and exterior surface 606 so as to bound a gap 620. It is appreciated that alternatively collet 512 can have a substantially annular transversal cross section without a gap. One benefit of having a gap within collet 512 is that it can allow collet 512 to be slightly transversally compressible which could allow easier insertion into collar 508 during assembly.

Similar to collar 508, interior surface 604 of side wall 602 bounds a longitudinal passage (denoted by arrow 622) that longitudinally extends through collet 512. Also similar to collar 508, side wall 602 is formed having a pair of channels 624 and 626 that are disposed on opposing sides of side wall 602 and that transversely extend through side wall 602 forming a transverse passage (denoted by arrow 628). Each channel 624 and 626 has a floor 630 that is rounded. Each channel 624 and 626 is configured so that stabilizing rod 14 can be received therein and bias against floor 630.

Exterior surface 606 comprises a first section 632 towards first end 608, a second section 634 towards second end 610, and a ledge 636 connecting first section 632 to second section 634 where the two sections overlap. The radius of second section 634 is greater than the radius of first section 632 which causes ledge 636 to face towards second end 610. Exterior surface 606 of collet 512 is configured to prevent collet 512 from being removed once collet 512 has been inserted into collar 508. In the embodiment depicted, this is accomplished by making the diameter of second section 634 of exterior surface 606 larger than the diameter of first section 572 of interior surface 520 of collar 508 while making the diameter of first section 632 of exterior surface 606 smaller or the same size as the diameter of first section 572. Collet 512 is configured to snap fit into collar 508, as described below, so that ledge 636 of collet 512 will pass by ledge 576 of interior surface 520 of collar 508. Once inserted into collar 508, ledge 576 will prevent collet 512 from being removed from collar 508.

Figure 32:
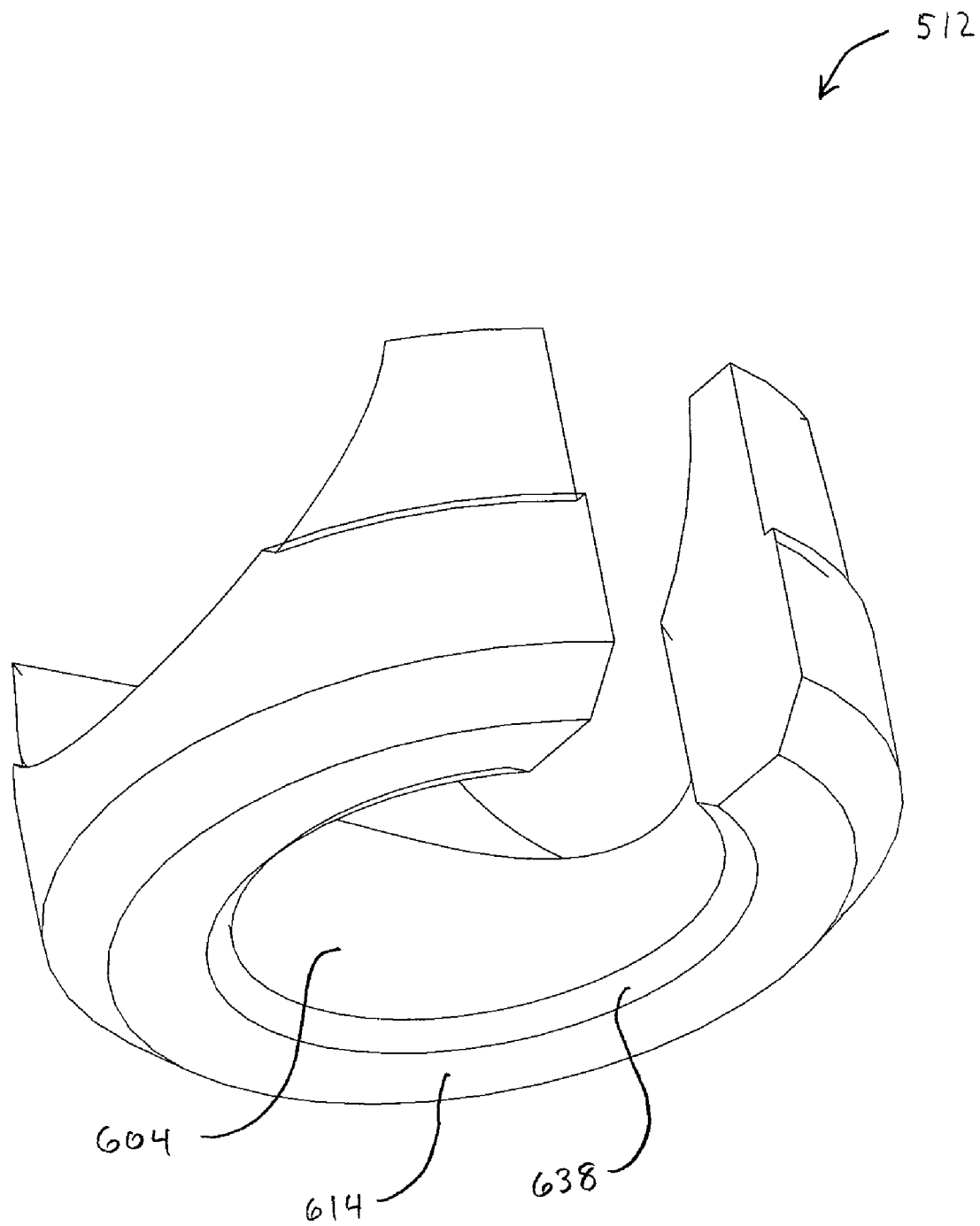
FIG. 32 is a bottom perspective view of the collet shown in FIG. 31.

Turning to FIG. 32 in conjunction with FIG. 31, collet 512 is configured to bias against head 596 of screw 506 (FIG. 27). To accomplish this, collet 512 has a tapered edge 638 formed in the transition between second end face 614 and interior surface 604. It is appreciated that the transition between second end face 614 and interior surface 604 can be rounded, have no taper, or have some other shape to allow collet 512 to more easily bias head 596. Furthermore, the amount of taper in tapered edge 638 can be greater or less than that depicted to allow more or less contact with head 596.

Figure 33:
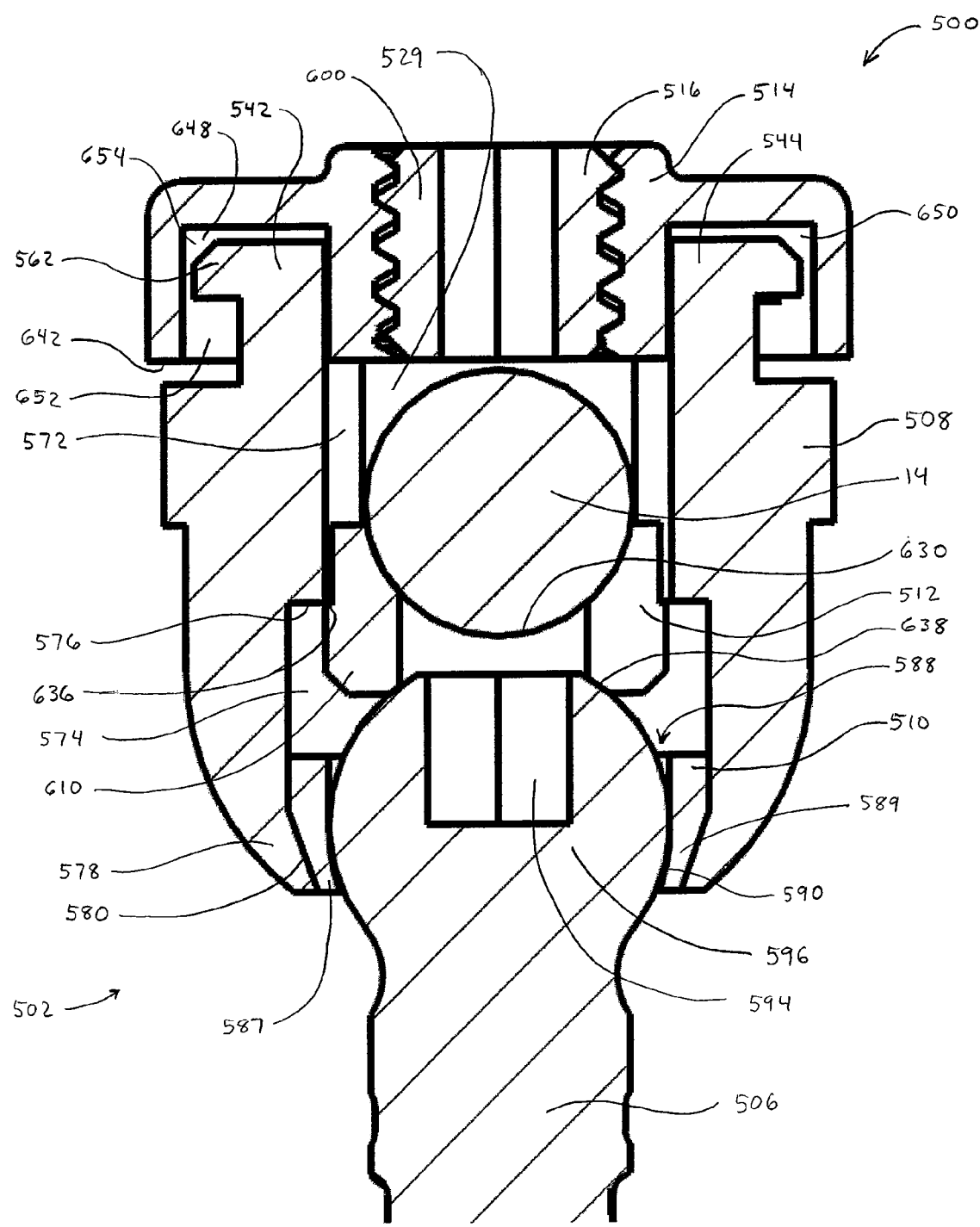
FIG. 33 is a cross sectional side view of the anchor assembly shown in FIG. 26.

As shown in FIG. 33, during assembly of anchor 502, second end 587 of locking ring 510 is passed down through longitudinal passage 529 of collar 508 so that shoulder 589 of locking ring 510 rests against seat 580 of collar 508 and is prevented from passing through longitudinal passage 529. Screw 506 is then advanced down through longitudinal passage 529 of collar 508 and longitudinal passage 588 of locking ring 510 so that head 596 rests against seat 590 of locking ring 510 and is also prevented from passing through longitudinal passage 529. Finally, second end 610 of collet 512 is passed down through longitudinal passage 529 of collar 508 and snap-fit into position so that ledge 636 of collet 512 passes by ledge 576 of collar 508 and tapered edge 638 of collet 512 rests against head 596 of screw 506. Screw 506, collar 508, locking ring 510, and collet 512 as thus assembled collectively comprise anchor 502. As a result of this configuration, once anchor 502 is assembled, collar 508 can pivot relative to head 596, and screw 506, locking ring 510, and collet 512 are prevented from being removed from collar 508.

With respect to previously described embodiments, by including locking ring 510 in anchor 502, an additional tapered surface 589 is added (along with tapered edge 638 of collar 512). This additional tapered surface allows a greater range of pivoting of screw 506 to occur with respect to collar 508. As such, in the depicted embodiment the amount of pivot in one direction from longitudinal axis 80 can be as high as about 30°. Other angles can also be formed.

Figure 34:
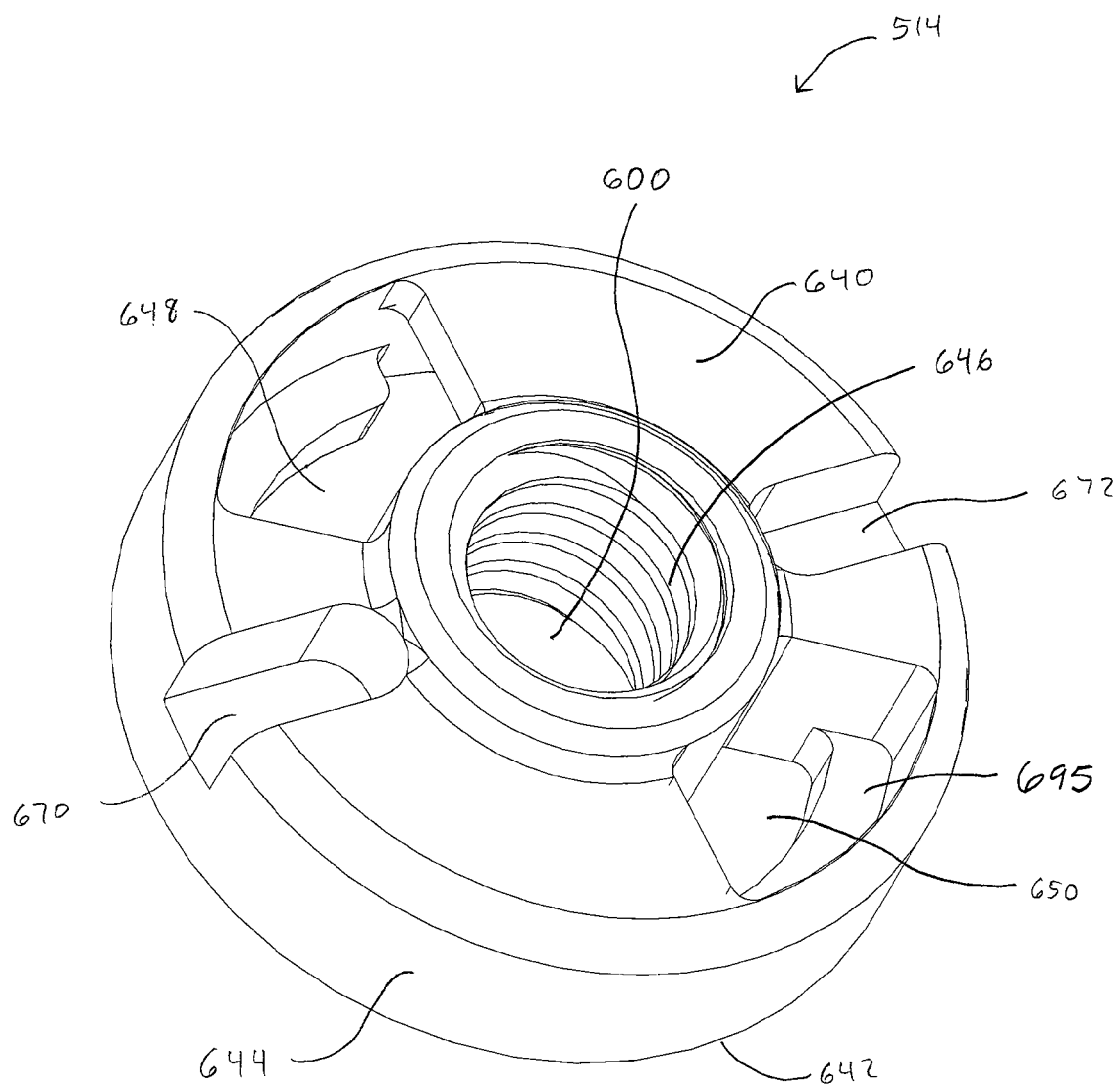
FIG. 34 is a top perspective view of a locking cap of the anchor assembly shown in FIG. 26.

As noted previously, cap assembly 504 comprises locking cap 514 adapted to be attached to collar 508 and fastener 516 adapted to be screwed into locking cap 514. As depicted in FIG. 34, locking cap 514 has a top surface 640 and an opposing bottom surface 642 that are both substantially circular with a side wall 644 extending therebetween. Hole 600 is formed in locking cap 514 and is bounded by a threaded side wall 646 that longitudinally extends all the way through locking cap 514.

As noted above, bayonet slots 648 and 650 are formed on locking cap 514 and are configured to engage with bayonet prongs 542 and 544, respectively, formed on collar 508 so as to provide a removably secure connection between locking cap 514 and collar 508. In the embodiment depicted, this is accomplished in a bayonet type of connection. Bayonet slots 648 and 650 are substantially similar. Thus, all disclosure with regard to bayonet slot 648 is also applicable to bayonet slots 650.

Figure 35:
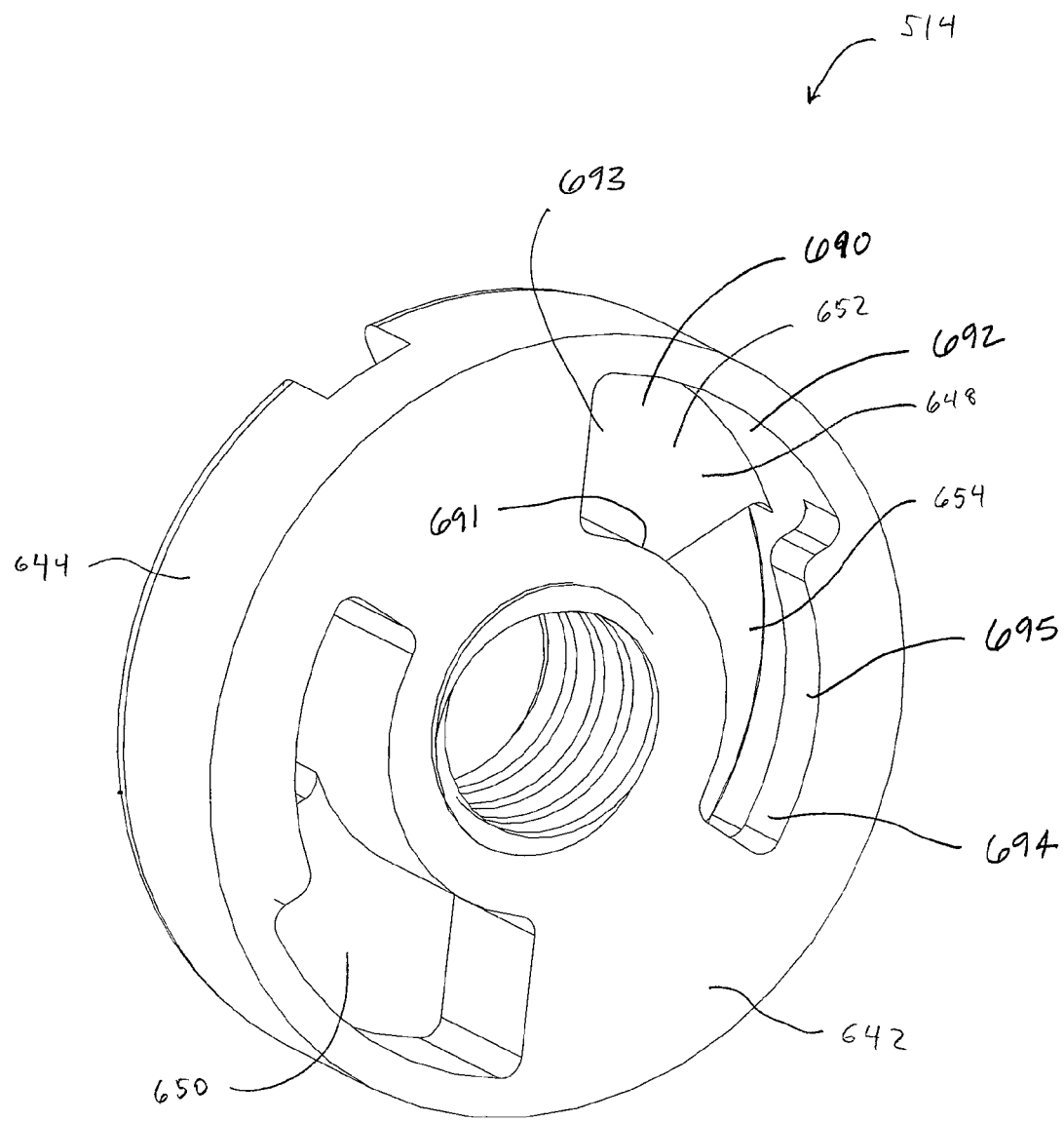
FIG. 35 is a bottom perspective view of the locking cap shown in FIG. 34.

As depicted in FIG. 35 in conjunction with FIG. 34, bayonet slot 648 comprises an elongated curved slot extending from bottom surface 642 to locking cap 514 to top surface 640. Slot 648 is bounded by an interior surface 691 and an opposing exterior surface 692 that extend between a first end 693 and an opposing second end 694. An elongated catch 695 projects from interior surface 691 into slot 648 along a portion of the length of slot 648 starting at second end 694. As a result, bayonet slot 648 comprises an enlarged entrance hole 652 at first end 693 and a constricted channel 654 that extends from entrance hole 652 to second end 694 along catch 695. With reference to FIGS. 28 and 35, entrance hole 652 is sized to receive bayonet prong 542. Channel 654 is configured so that when locking cap 514 is rotated relative to collar 508, body 546 of bayonet prong 542 is received within channel 654 while tab 562 extends over catch 695. As such, the engagement between catch 695 and tab 562 secures locking cap 514 to collar 508. In turn, locking cap 514 can be released from collar 508 by rotating locking cap 514 in the opposite direction.

In one embodiment of the present invention, means are provided for securing locking cap 514 to collar 508 so as to restrict outward radial expansion of collar 508. One example of such means includes bayonet slots 648 and 650 and bayonet prongs 542 and 544 as discussed above. In an alternative embodiment, it is appreciated that catches 695 can be formed on interior surfaces 691 of the bayonet slots while tabs 562 can be positioned on the interior surfaces 548 of the bayonet prongs. In yet another embodiment, locking cap 514 can comprise a cap that includes a circular top having an annular flange that downwardly projects from the perimeter edge thereof. Threaded hole 600 can be centrally formed on the circular top while screw threads are also be formed on the interior surface of the annular flange. Collar 508 can be modified so that corresponding threads are formed on the exterior surface 550 of the bodies 546. As a result, the cap could be threaded onto collar so as to prevent unwanted expansion of the collar and yet still enable the use fastener 516. Other embodiments can also be used.

Returning to FIG. 34, a pair of grooves 670 and 672 are formed on top surface 640. Grooves 670 and 672 are provided to allow a tool to be used to rotate locking cap 514 to secure or remove locking cap 514 to or from collar 508. The tool (not shown) can have corresponding teeth that are received within grooves 670 and 672 so that locking cap 514 will rotate as the tool is rotated. Alternately, grooves 670 and 672 can be used to keep locking cap from rotating when fastener 516 is threaded into hole 600.

Returning to FIG. 27, fastener 516 is similar to fastener 24 shown in FIG. 2, except that fastener 516 is radially smaller so as to fit within threaded hole 600 of locking cap 514. As such, fastener 516 comprises a body 674 having an encircling side wall 676 that extends between a top end face 678 and an opposing bottom end face 680. Helical threads 682 are shaped so as to threadedly engage with threaded hole 600. Because fastener 516 is radially smaller than fastener 24, polygonal socket 682 is smaller than polygonal socket 120.

A number of benefits are realized by configuring cap assembly 504 thusly. For example, the bayonet style connection used to connect locking cap 514 to collar 508 also provides the added benefit of preventing the opposing sides of collar 508 separated by channels 538 and 540 from spreading apart during insertion and after. Another benefit is that fastener 516 can be pre-inserted into locking cap 516 at the factory or elsewhere before it is sent out to a doctor to use. By doing this, any potential cross threading or stripped threading problems caused when the doctor inserts the anchor can be avoided.

Returning to FIG. 33, a method of using anchor assembly 500 is now discussed. Initially, anchor 502, assembled as discussed above, is mounted onto a vertebra in a similar manner as previous embodiments discussed above, using a driver or other type of attaching mechanism to secure screw 506 within a hole in the vertebra. Methods and drivers discussed previously can also be used with anchor 502. In the embodiment depicted, a tool is used to engage socket 594 of bone screw 506 and screw bone screw 506 into the bone.

After screw 506 has been secured to the bone, stabilizing rod 14 is inserted into collar 508 such that stabilizing rod 14 extends transversally through transverse passage 529 defined by collar 508 and biases against floor 630 of channels 624 and 626 of collet 512. To facilitate this, collet 512 may first need to be rotated within collet 508 to align channels 624 and 626 of collet 512 with channels 530 and 532 of collar 508.

After stabilizing rod 14 has been inserted into collar 508, locking cap 514 is positioned above collar 508 so that entrance holes 652 of bayonet slots 648 and 650 are aligned with tabs 562 of bayonet prongs 542 and 544, respectively, of collar 508. Locking cap 514 is then secured to collar 508 by pushing down on locking cap 514 so that tabs 562 are received within entrance holes 652 and then rotating locking cap 514 to secure tabs 562 within channels 654.

Collar 508 is then pivoted with respect to screw 506 until a desired angle is achieved. Once the desired angle is achieved, fastener 516 is then screwed into threaded hole 600 of locking cap 514 if fastener 516 was not pre-inserted into hole 600, as discussed above. Fastener 516 is tightened so that fastener 516 biases stabilizing rod 14 against collet 512, which in turn biases against head 596 of screw 506. In this configuration, stabilizing rod 14 is secured from unwanted movement by being compressed between fastener 516 and collet 512. Furthermore, as collet 512 pushes against head 596, head 596 is wedged against seat 590 of locking ring 510 and locking ring 510 is wedged against seat 580 of collar 508, thereby also locking collar 508 relative to screw 506.

Although in the foregoing discussion bone screw 506 is secured to the bone before locking cap 514 is secured to collar 508, it is appreciated that in some embodiments locking cap 514 can be secured first to collar 508. For example, in the embodiment depicted in FIG. 33, socket 594 is transversally smaller than hole 600 formed on locking cap 514. In this embodiment, locking cap 514 alternatively can first be secured to collar 508 before screw 506 is secured to the bone, if desired. When screw 506 is secured to the bone in this manner, locking cap 514 can subsequently be removed to allow stabilizing rod 14 to be inserted into longitudinal passage 529.

Figure 36:
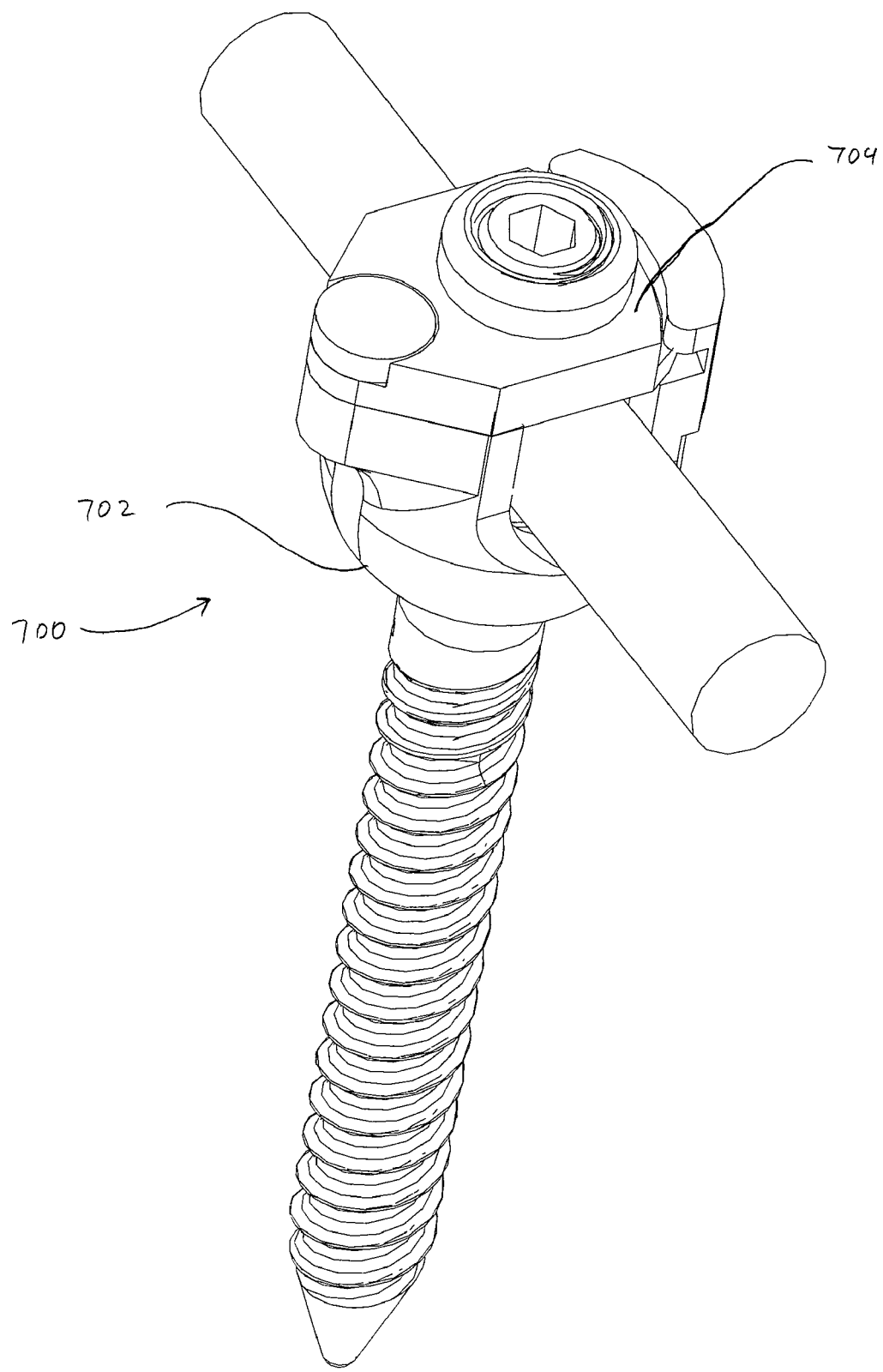
FIG. 36 is a perspective view of another alternative embodiment of an anchor assembly.
Figure 37:
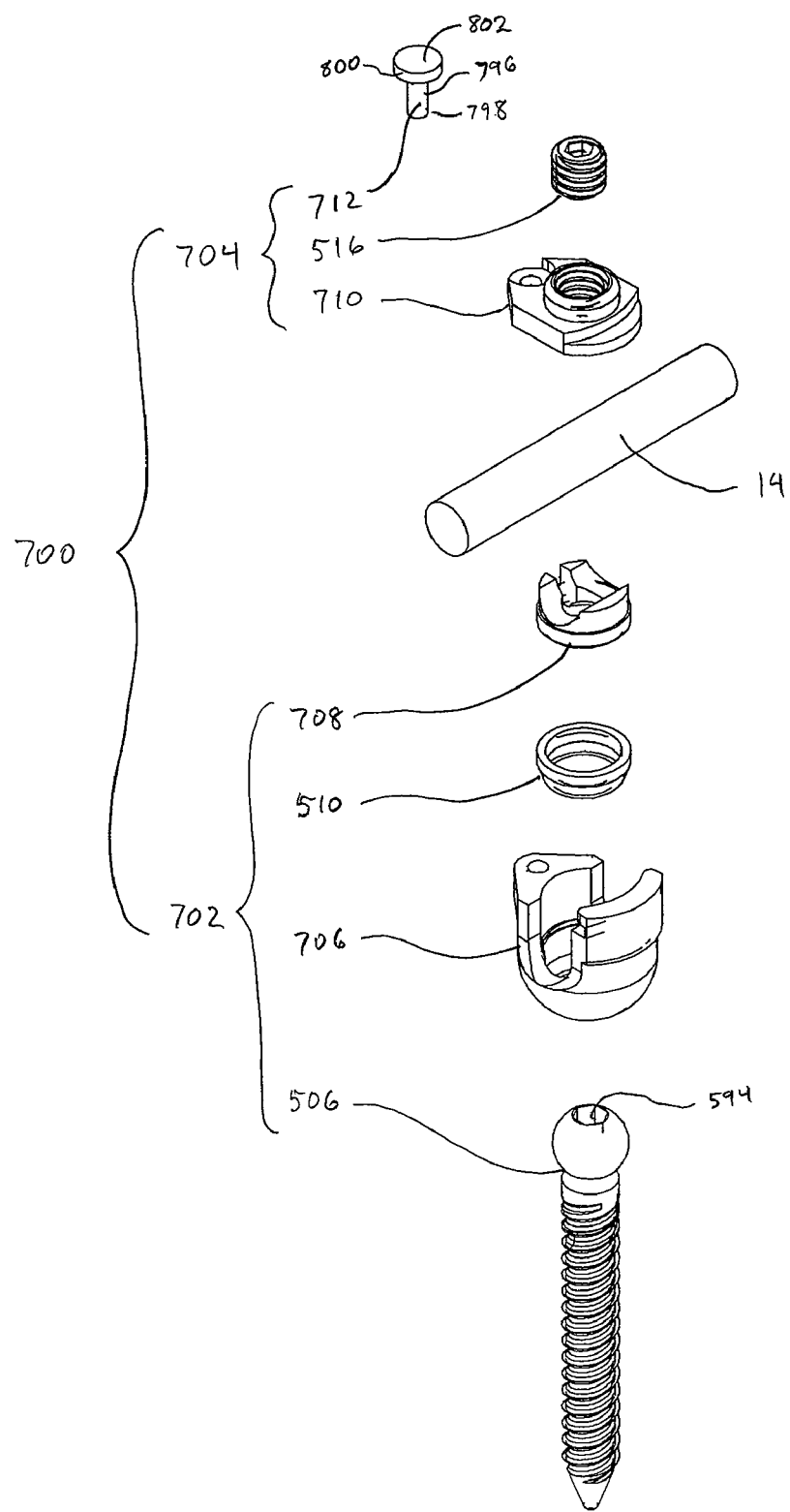
FIG. 37 is an exploded perspective view of the anchor assembly shown in FIG. 36.

Depicted in FIG. 36 is another alternative embodiment of an anchor assembly 700 incorporating features of the present invention. Like elements between previously described anchor assemblies and anchor assembly 700 are identified by like reference characters. Similar to previously described anchor assemblies, anchor assembly 700 comprises an anchor 702 on which a cap assembly 704 selectively engages. As shown in FIG. 37 and similar to anchor 502, anchor 702 comprises an elongated screw 506, a collar 706 pivotally mounted on screw 506, and a locking ring 510 and a collet 708, both received within collar 706. Similar to cap assembly 504, cap assembly 704 comprises a locking cap 710 adapted to be attached to collar 706 and a fastener 516 adapted to be screwed into locking cap 710. Cap assembly 704 further includes a locking pin 712 to pivotally secure locking cap 710 to collar 706, as described in further detail below.

Figure 38:
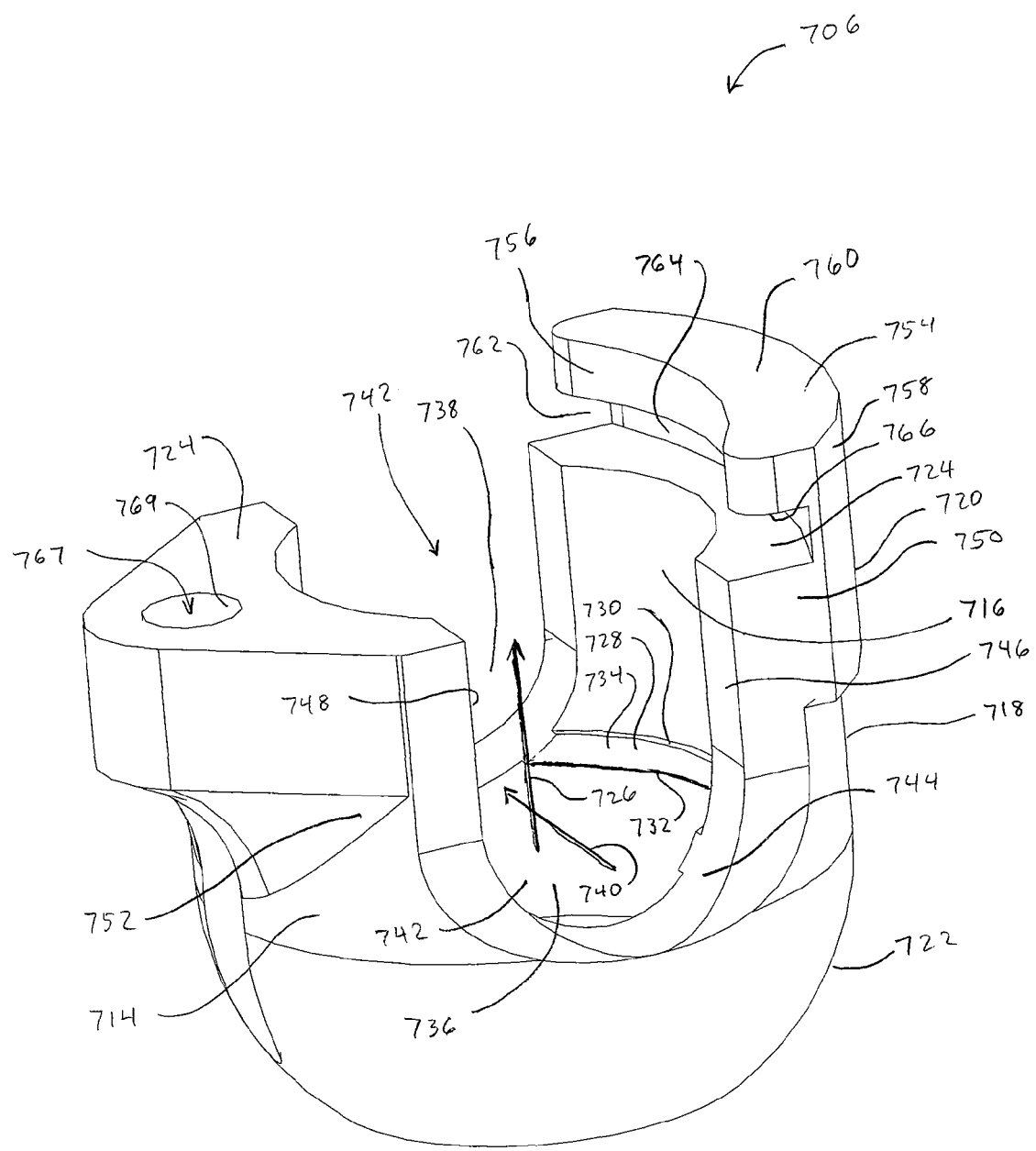
FIG. 38 is a top perspective view of the collar of the anchor assembly shown in FIG. 36.

As depicted in FIG. 38 and similar to collar 508, collar 706 comprises a tubular side wall 714 having an interior surface 716 and an exterior surface 718 that each extend between a first end 720 and an opposing second end 722. First end 720 terminates at a terminal end face 724. Interior surface 716 bounds a longitudinal passage (denoted by arrow 726) that longitudinally extends through collar 706.

An annular ring 728 is formed on interior surface 716 of collar 706. Annular ring 728 comprises a top surface 730 and an opposing bottom surface 732 that both project into longitudinal passage 726 from interior surface 716 of collar 706. Similar to ledge 576 of collar 508, bottom surface 732 lies in a plane that is substantially orthogonal to the direction of longitudinal passage 529. An interior surface 734 extends between top surface 730 and bottom surface 732 opposite interior surface 716. See also FIG. 42 for a cross-sectional view of annular ring 728. It is appreciated that in other embodiments, the ledge arrangement described previously with regard to collar 508 can be used in place of ring 728 in collar 706 and ring 728 can be used alternatively in collar 508.

As opposed to previously described embodiments, exterior surface 718 of collar 706 has a multi-shaped transverse cross section. As discussed previously with other collars, many types of shapes alternatively can be used.

Side wall 714 is formed having a pair of channels 736 and 738 which are substantially similar to channels 42 and 44 of collar 22. As such, similar to channels 42 and 44, channels 736 and 738 are disposed on opposing sides of side wall 714 and transversely extend through side wall 714 forming a transverse passage (denoted by arrow 740). In the embodiment depicted, channels 736 and 738 each have a substantially U-shaped configuration, but as discussed with regard to channels 42 and 44, other configurations can be used. Each channel 736 and 738 has an open mouth 742 that extends through end face 724 and an opposing floor 744 that is rounded. Similar to channels 42 and 44, each channel 736 and 738 is configured so that stabilizing rod 14 can be received therein. Each of channels 736 and 738 are bounded by opposing side surfaces 746 and 748. Similar to channels 42 and 44, side surfaces 746 and 748 can be in substantially parallel alignment or not, as discussed previously. Channels 736 and 738 form a portion of transverse passage 740 so as to intersect with the longitudinal passage 726 that also extends through collar 508. Channels 736 and 738 divide side wall 714 at first end 720 into a first arm 750 and a second arm 752.

A retainer 754 longitudinally extends away from first end 720 of first arm 750 of collar 706. Retainer 754 comprises an interior surface 756 and an opposing exterior surface 758 extending from end face 724 of collar 708 to a top surface 760. Retainer 754 has an inverted "L" cross-sectional shape such that interior surface 756 near top surface 760 is more inwardly projecting than interior surface 756 nearer terminal end face 724 of first arm 750. In this manner, a channel 762 is bounded by end face 724 of collar 708 and by a back wall 764 and a bottom wall 766 of retainer 754. Channel 762 is configured to allow securing member 788 of locking cap 710 to be selectively received by sliding in a direction substantially transversal to the direction of longitudinal passage 726, as will be discussed in more detail below.

As shown in the embodiment depicted, side wall 714 flares out at first end 720 of second arm 752 of collar 706. An aperture 767 bounded by a sidewall 769 is located in flared out second arm 752. Aperture 767 extends downward from end face 724 and completely through flared out side wall 714.

Figure 39:
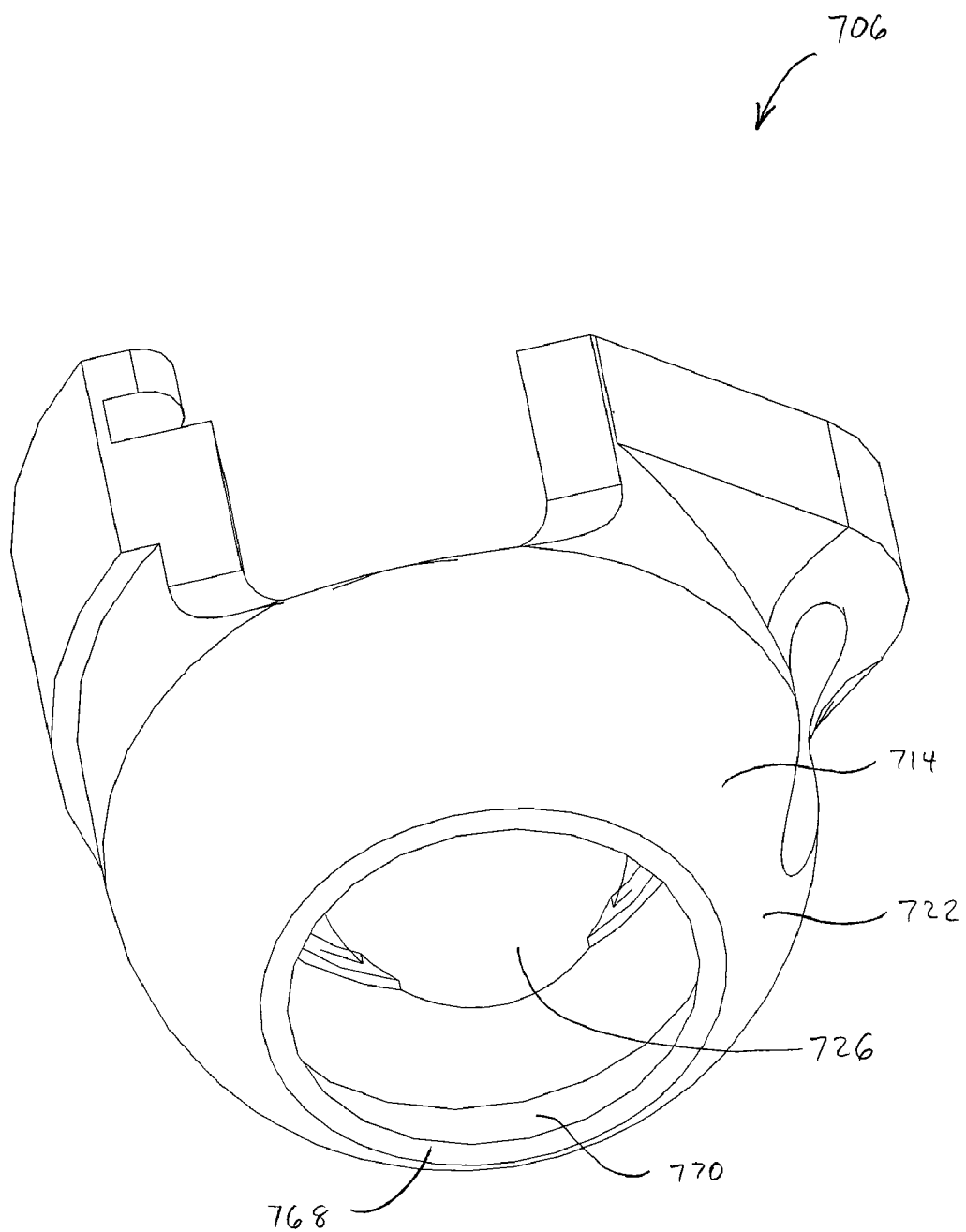
FIG. 39 is a bottom perspective view of the collar shown in FIG. 38.

Turning to FIG. 39 and similar to collar 508, collar 706 further comprises a shoulder 768 that radially inwardly projects from second end 722 of side wall 714 so as to encircle longitudinal passage 726. Shoulder 768 has a tapered interior surface that forms an annular seat 770. See also FIG. 42 for a cross-sectional view of collar 706 showing shoulder 768 and seat 770.

Figure 40:
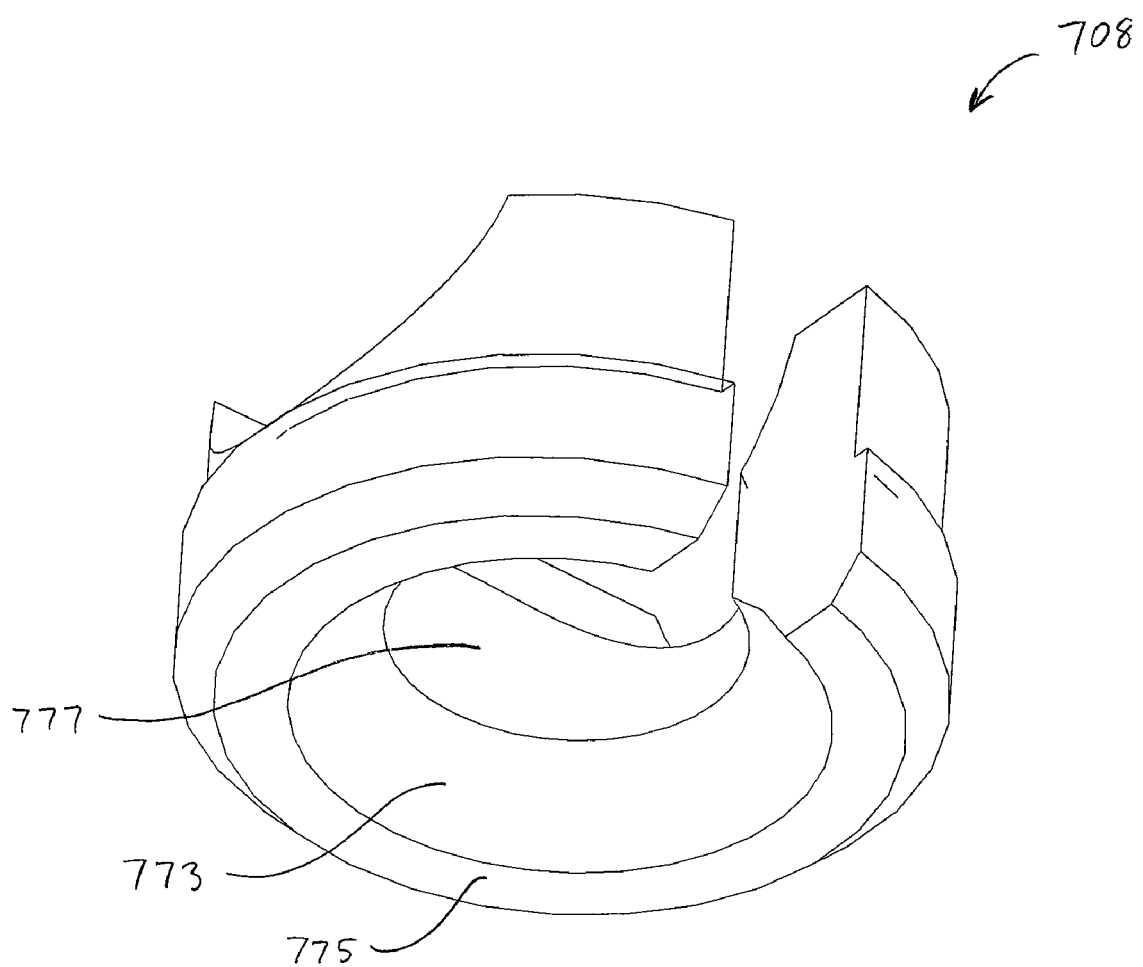
FIG. 40 is a top perspective view of a collet of the anchor assembly shown in FIG. 36.
Figure 41:
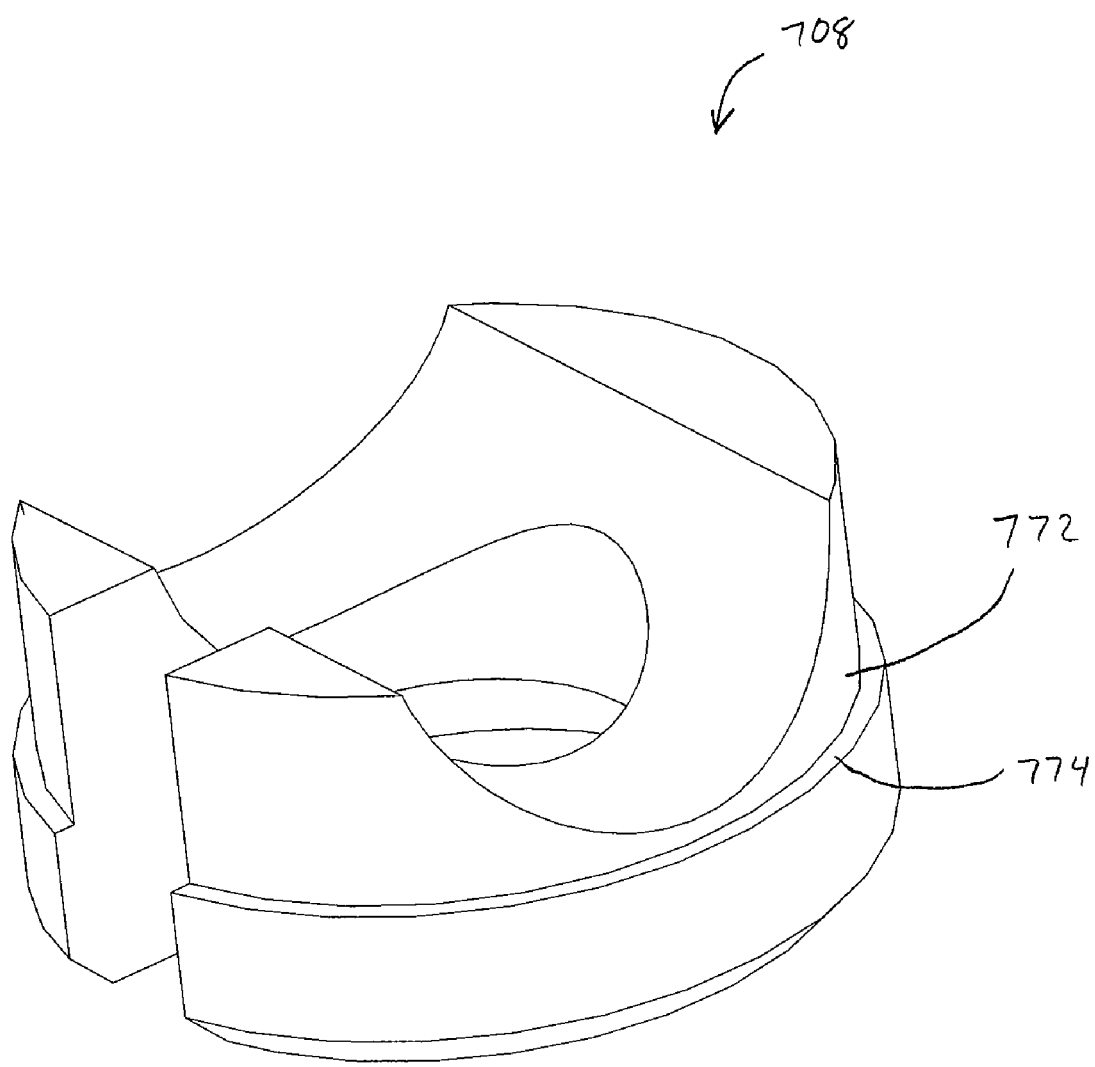
FIG. 41 is a bottom perspective view of the collet shown in FIG. 40.

As depicted in FIGS. 40 and 41, collet 708 is substantially similar to collet 512 except that side wall 772 of collet 708 is longitudinally longer than side wall 602 of collet 512, allowing ledge 774 to more completely encircle side wall 772. Also, the tapered edge 773 formed in the transition between second end face 775 and interior surface 777 has more of a taper than tapered edge 638 of collet 512. However, the functionality of collet 708 is substantially similar to collet 512.

Figure 42:
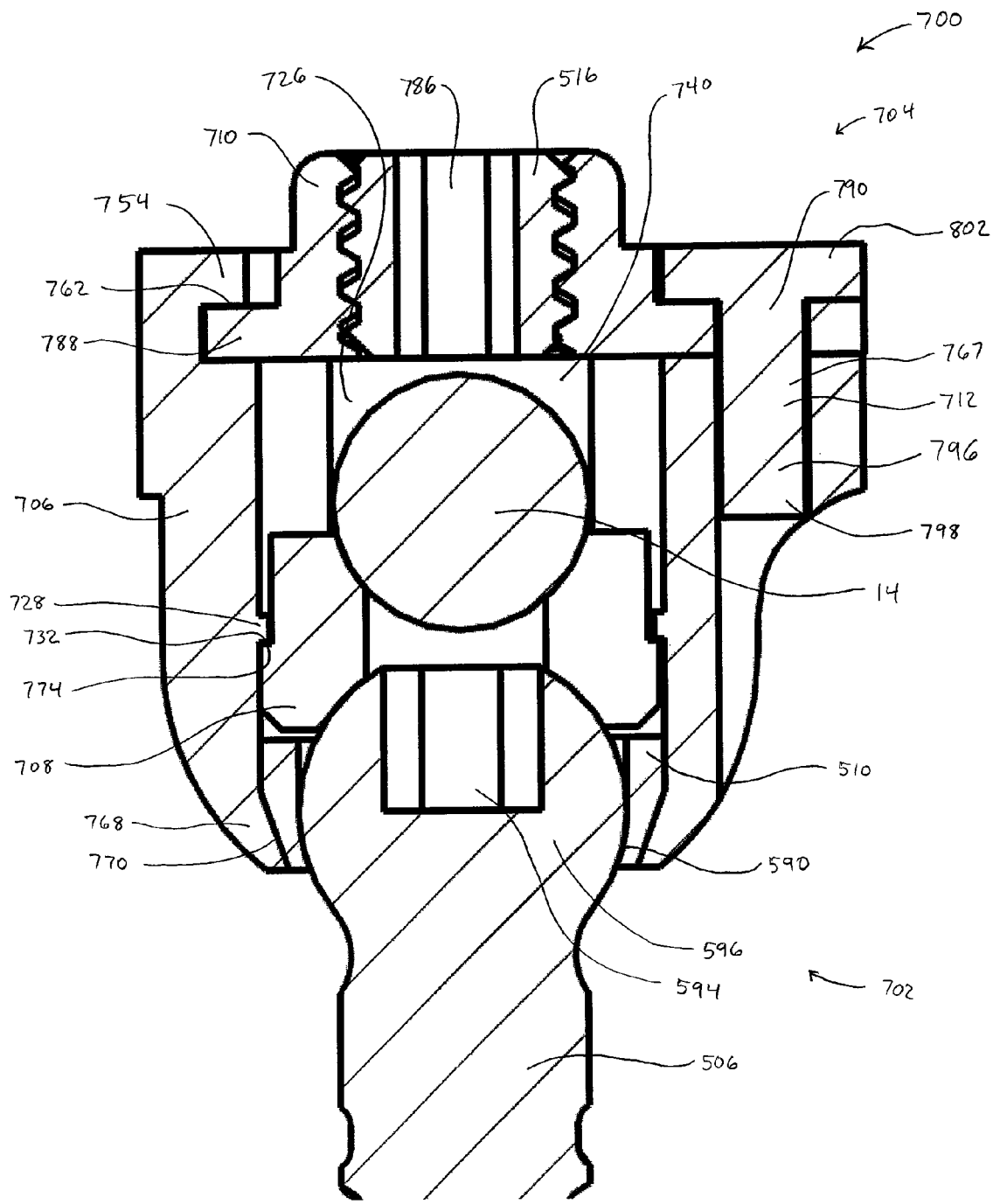
FIG. 42 is a cross sectional side view of the anchor assembly shown in FIG. 36.

Turning to FIG. 42, assembly of anchor 702 is performed in substantially the same manner as assembly of anchor 502, discussed previously. As such, locking ring 510 is first inserted into collar 706, followed by screw 506 and collet 708, in that order. Ring 728 formed on collar 706 prevents collet 708 from being removed from collar 706 in substantially the same manner as described with regard to anchor 502. That is, once collet 708 has been inserted such that ledge 774 formed on collet 708 has passed beyond ring 728, bottom surface 732 of ring will prevent collet 708 from being removed. Screw 506, collar 706, locking ring 510, and collet 708 as thus assembled collectively comprise anchor 702. Similar to anchor 502, once anchor 702 is assembled, collar 706 can pivot relative to head 596, and screw 506, locking ring 510, and collet 708 are prevented from being removed from collar 706.

Figure 43:
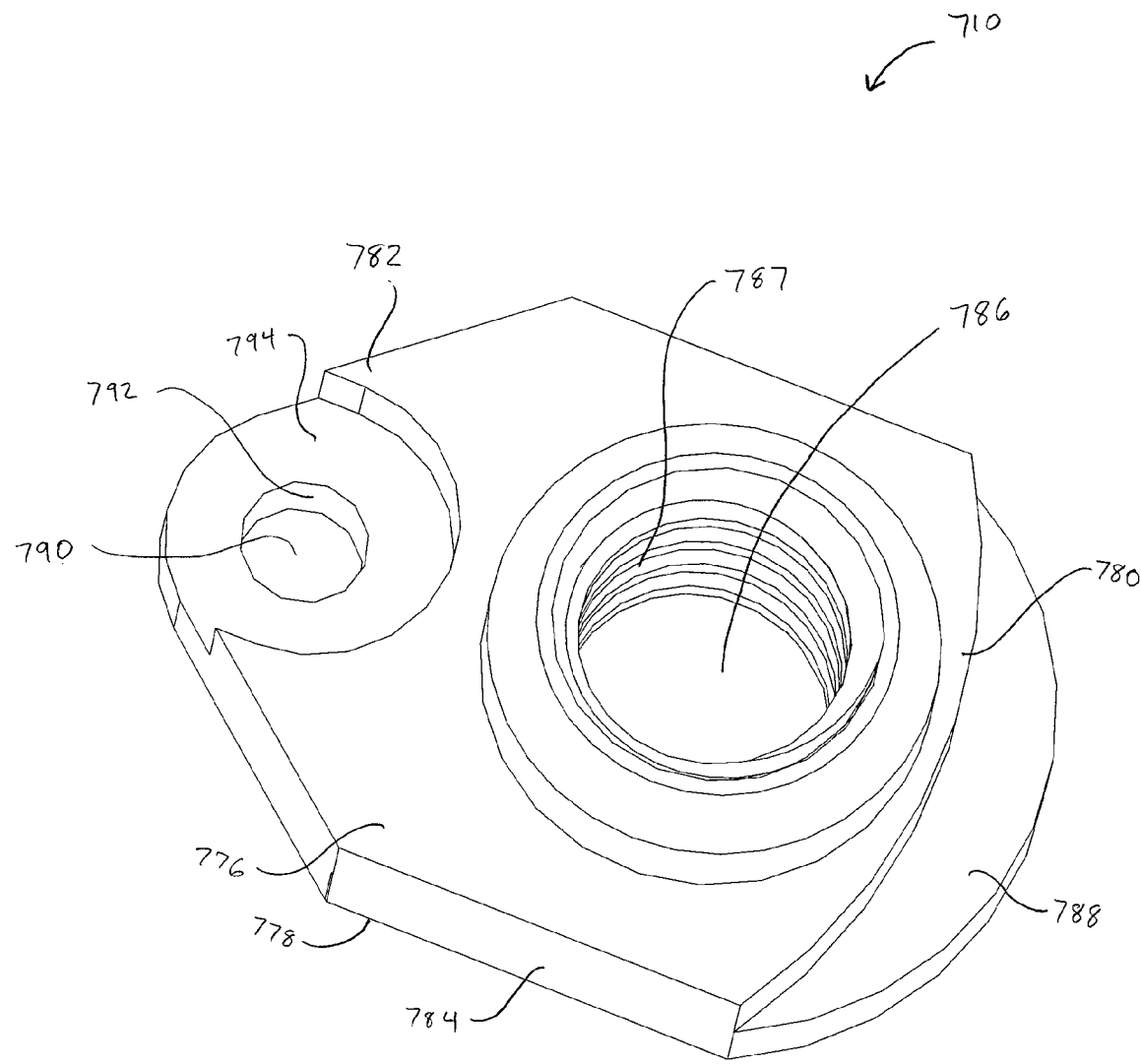
FIG. 43 is a top perspective view of a locking cap of the anchor assembly shown in FIG. 36.

As noted previously, cap assembly 704 comprises locking cap 710 adapted to be attached to collar 706, fastener 516 adapted to be screwed into locking cap 710, and locking pin 712 configured to pivotally secure locking cap 710 to collar 706. As depicted in FIG. 43, locking cap 710 has a top surface 776 and an opposing bottom surface 778 both extending from a first end 780 to a second end 782 with a sidewall 784 extending between top surface 776 and bottom surface 778. Similar to threaded hole 600 of locking cap 514, a hole 786 is formed in locking cap 710 bounded by a threaded side wall 787 that longitudinally extends all the way through locking cap 710. Threaded hole 786 may be raised, as in the embodiment depicted, or may be flush with top surface 776.

A securing member 788 projects out from first end 780 of locking cap 710. Securing member 788 is configured to be selectively received within channel 762 of retainer 754 on collar 706 by sliding in a direction substantially transversal to the direction of longitudinal passage 726.

A passageway 790 extending completely through locking cap 710 is formed at second end 782 of locking cap 710. Passageway 790 is bounded by an interior wall 792 formed in locking cap 710. In some embodiments, a recess 794 is formed around passageway 790.

Returning to FIG. 37, locking pin 712 has a substantially cylindrical shaft 796 extending from a first end 798 to an opposing second end 800. A head 802 is formed at second end 798 of locking pin 712. Head 802 has a larger diameter than shaft 796. Locking pin 712 is configured to attach locking cap 710 to collar 706 so as to allow locking cap 710 to pivot about locking pin 712 while attached to collar 706.

One advantage of the depicted embodiment is that cap assembly 704 can be preattached to anchor 702 at the factory or elsewhere before it is sent out to a doctor to use. By doing this, the doctor only has to worry about a single part (the preassembled anchor assembly), making it easier for the doctor to keep track of and use. Returning to FIG. 42, to attach cap assembly 704 to anchor 702, fastener 516 is screwed into threaded hole 786 on locking cap 710, and first end 798 of locking pin 712 is inserted down through passageway 790 formed on locking cap 710 and into aperture 767 in collar 706 of completed anchor 702. Head 802 of locking pin 712 prevents locking pin 712 from passing completely through locking cap 710. Once inserted through locking cap 710 and into collar 708, shaft 796 of locking pin 712 is secured to collar at first end 798 in a manner that will allow locking cap 710 to be able to pivot about locking pin 712. This can be done in a number of ways. For example, first end 798 of locking pin 712 can be threaded, welded, glued, press fit or otherwise attached to collar 706. Alternately, aperture 767 and shaft 796 can be configured to produce a snap-fit type of connection. In other embodiments, locking pin 712 can comprise a rivet. Furthermore, collar can be integrally formed with a post that is received within passageway 790 of locking cap 710 or locking cap can be integrally formed with a post that is received within aperture 767 of collar 706. It is appreciated that there are yet a variety of other ways to pivotably mount locking cap 710 on collar 706. In one embodiment of the present invention means are provided for pivotably mounting locking cap 710 on collar 706. Examples of such means include the examples set forth above.

Referring to FIG. 42, a method of using anchor assembly 700 is now discussed. Initially, anchor assembly 700, assembled as discussed above, is mounted onto a vertebra in a similar manner as discussed above with regard to anchor 502, using a driver or other type of attaching mechanism to secure screw 506 within a hole in the vertebra. Methods and drivers discussed previously can also be used with anchor 702. In the embodiment depicted, a tool (not shown) is used to engage socket 594 of bone screw 506 and screw bone screw 506 into the bone. Because cap assembly 704 is preattached to anchor 702, locking cap 710 must be rotated out of the way before bone screw 506 can be secured into the bone. Alternatively, as discussed with regard to anchor assembly 500, if socket 594 on screw 506 is transversally smaller than hole 786 formed on locking cap 710, locking cap 710 can first be closed and secured to collar 706, as described below, before screw 506 is secured to the bone using a tool that can be inserted through hole 786. If mounting is performed in this manner, then locking cap 710 can be rotated out of the way to complete the installation of anchor 700.

After screw 506 has been secured to the bone, stabilizing rod 14 is inserted into collar 706 such that stabilizing rod 14 extends transversally through transverse passage 740 defined by collar 706 and biases against collet 708 in a manner similar to that discussed previously with regard to anchor 502.

After stabilizing rod 14 has been inserted into collar 706, locking cap 710 is rotated about locking pin 712 to slide securing member 788 into channel 762 on retainer 754 of collar 706 and to align threaded hole 786 with longitudinal passage 726.

Collar 706 is then pivoted with respect to screw 506 until a desired angle is achieved. Once the desired angle is achieved, fastener 516 is then screwed into threaded hole 786 of locking cap 710 in a similar manner as discussed above with regard to anchor assembly 500. Fastener 516 is tightened so that fastener 516 biases stabilizing rod 14 against collet 708, which in turn biases against head 596 of screw 506. As discussed above, in this configuration stabilizing rod 14 is secured from unwanted movement by being compressed between fastener 516 and collet 708. Furthermore, as collet 708 pushes against head 596, head 596 is wedged against seat 590 of locking ring 510 and locking ring 510 is wedged against seat 770 of collar 706, thereby also locking collar 706 relative to screw 506.

There are a variety of different anchor assemblies disclosed herein. It is appreciated that the components, features, elements and designs of the different embodiments can be mixed and matched to form other embodiments that are within the scope of the present invention.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A bone stabilizing system comprising:
    a collar comprising:
        a tubular sidewall having an interior surface and an exterior surface each extending between a first end and an opposing second end, the interior surface at least partially bounding a longitudinal passage extending therethrough;
        a pair of opposing spaced apart channels transversely extending through the sidewall at the first end thereof; and
        a pair of spaced apart bayonet prongs projecting from the first end of the tubular sidewall;
    a screw having a threaded portion and a head disposed on an end thereof, the head of the screw being disposed within the longitudinal passage of the collar;
    a locking cap having a top surface and an opposing bottom surface, with a perimeter side wall extending therebetween, a threaded hole extending through the locking cap between the top and bottom surfaces, and a pair of spaced apart bayonet slots formed on the bottom surface and extending therefrom toward the top surface, the bayonet slots each having an entrance opening formed on the bottom surface of the locking cap, each entrance opening being completely and separately encircled by the bottom surface at spaced apart locations so that each entrance opening comprises a separate and distinct opening, the bayonet slots being configured to receive and engage with the pair of bayonet prongs so as to secure the locking cap to the collar; and
    a fastener received within the threaded hole formed on the locking cap.

2. The bone stabilizing system as recited in claim 1, wherein the locking cap encircles the pair of bayonet prongs when the locking cap is secured to the collar so as to prevent unwanted expansion of the collar.

3. The bone stabilizing system as recited in claim 1, wherein the pair of bayonet prongs each include an outwardly projecting tab, the tabs of the pair of bayonet prongs being positioned so as to face away from each other.

4. The bone stabilizing system as recited in claim 1, further comprising an annular locking ring disposed within the longitudinal passage of the collar, the head of the screw being encircled by and supported by the locking ring to prevent the head of the locking screw from contacting the second end of the collar.

5. The bone stabilizing system as recited in claim 1, wherein the head of the screw has a socket formed thereon, the socket having a maximum diameter that is equal to or smaller than a maximum diameter of the threaded hole formed on the locking cap.

6. The bone stabilizing system as recited in claim 1, further comprising:
    the spaced apart channels at least partially bounding a transverse passage that transversely extends through the collar and intersects with the longitudinal passage; and
    a stabilizing rod disposed within the transverse passage so as to extend through the spaced apart channels.

7. The bone stabilizing system as recited in claim 6, further comprising a collet disposed within the longitudinal passage of the collar, the collet being disposed between the head of the screw and the stabilizing rod with the stabilizing rod being supported on the collet.

8. The bone stabilizing system as recited in claim 1, further comprising a collet disposed within the longitudinal passage of the collar, the collet being disposed between the head of the screw and the fastener.

9. The bone stabilizing system as recited in claim 8, wherein the collet has a substantially C-shaped annular cross section.

10. The bone stabilizing system as recited in claim 9, further comprising a pair of aligned, spaced apart channels formed on the collet.

11. The bone stabilizing system as recited in claim 8, further comprising:
    the spaced apart channels on the collar at least partially bounding a transverse passage that transversely extends through the collar and intersects with the longitudinal passage; and
    a stabilizing rod disposed within the transverse passage of the collar and being supported on the collet.

12. The bone stabilizing system as recited in claim 1, wherein the bottom surface of the locking cap is free of any integral structure projecting downward therefrom.

13. The bone stabilizing system as recited in claim 1, wherein the bayonet slots extend through the locking cap between the bottom and top surfaces.

14. The bone stabilizing system as recited in claim 1, wherein each entrance opening of each bayonet slot comprises an enlarged entrance hole and an adjacent constricted channel, the constricted channel being bounded by a catch lip.

15. The bone stabilizing system as recited in claim 1, wherein the pair of bayonet prongs are secured within the bayonet slots of the locking cap.

16. The bone stabilizing system as recited in claim 1, wherein the locking cap is integrally formed as a unitary structure from a single piece of material.

17. The bone stabilizing system as recited in claim 1, wherein the bottom surface of the locking cap is substantially planar.

18. The bone stabilizing system as recited in claim 1, wherein the threaded hole is completely encircled by the bottom surface of the locking cap at a spaced apart location from the entrance openings so that the threaded hole and the entrance openings each comprise separate and distinct openings on the bottom surface.

19. A bone stabilizing system comprising:
    a collar comprising:
        a tubular sidewall having an interior surface and an exterior surface each extending between a first end and an opposing second end, the interior surface at least partially bounding a longitudinal passage extending therethrough;
        a pair of opposing spaced apart channels transversely extending through the sidewall at the first end thereof; and
        a pair of spaced apart prongs projecting from the first end of the tubular sidewall;

a screw having a threaded portion and a head disposed on an end thereof, the head of the screw being disposed within the longitudinal passage of the collar;

a locking cap having a top surface and an opposing bottom surface, with a perimeter side wall extending therebetween, a threaded hole extending through the locking cap between the top and bottom surfaces, and a pair of spaced apart slots formed on the bottom surface, each slot being completely encircled at spaced apart locations by separate and distinct inside perimeter walls of the locking cap extending from the bottom surface toward the top surface, the slots being configured to receive the pair of prongs; and a fastener received within the threaded hole formed on the locking cap.

20. The bone stabilizing system as recited in claim 19, wherein the bottom surface of the locking cap completely encircles each spaced apart slot such that a separate and distinct entrance opening is formed on the bottom surface corresponding to each slot.

21. The bone stabilizing system as recited in claim 19, wherein the slots extend through the locking cap between the bottom and top surfaces.

22. The bone stabilizing system as recited in claim 19, wherein the pair of prongs are secured within the slots of the locking cap.

23. A bone stabilizing system comprising:

a collar comprising:

a tubular sidewall having an interior surface and an exterior surface each extending between a first end and an opposing second end, the interior surface at least partially bounding a longitudinal passage extending therethrough;

a pair of opposing spaced apart channels transversely extending through the sidewall at the first end thereof; and a pair of spaced apart bayonet prongs projecting from the first end of the tubular sidewall;

a screw having a threaded portion and a head disposed on an end thereof, the head of the screw being disposed within the longitudinal passage of the collar;

an annular locking ring disposed within the longitudinal passage of the collar, the head of the screw being encircled by and supported by the locking ring to prevent the head of the screw from contacting the second end of the collar;

a collet disposed within the longitudinal passage of the collar;

a locking cap having a threaded hole extending therethrough and a pair of spaced apart bayonet slots formed thereon, the bayonet slots being configured to receive and engage with the pair of bayonet prongs so as to secure the locking cap to the collar, each bayonet slot having an entrance opening formed on a bottom surface of the locking cap, each entrance opening being completely and separately encircled by the bottom surface at spaced apart locations so that each entrance opening comprises a separate and distinct opening; and a fastener received within the threaded hole formed on the locking cap, the collet being disposed between the head of the screw and the fastener.

* * * * *

UNITED STATES PATENT AND TRADEMARK OFFICE
CERTIFICATE OF CORRECTION

| | |
|---|---|
| PATENT NO. | : 8,016,862 B2 |
| APPLICATION NO. | : 11/863133 |
| DATED | : September 13, 2011 |
| INVENTOR(S) | : Felix et al. |

It is certified that error appears in the above-identified patent and that said Letters Patent is hereby corrected as shown below:

Column 3
Line 49, change "rod" to --rod;--

Column 5
Line 41, change "side wall 50" to --side wall 28--

Column 7
Line 63, change "first retainer 130" to --first retainer 136--
Line 64, change "first retainer 126" to --first retainer 136--

Column 8
Line 19, change "screw 25" to --screw 26--
Line 55, change "complimentary" to --complementary--

Column 9
Line 17, change "transverse passages 54" to --transverse passage 54--
Line 42, change "complimentary" to --complementary--
Line 57, change "complimentary" to --complementary--

Column 10
Line 53, change "second end 248" to --second end 247--

Column 11
Line 17, change "shaft 264" to --shaft 254--
Lines 27-28, change "screw 254" to --screw 252--

Column 12
Line 32, change "second tapered portion" to --second tapered portion 344--

Signed and Sealed this
Seventh Day of February, 2012

David J. Kappos
*Director of the United States Patent and Trademark Office*

CERTIFICATE OF CORRECTION (continued)
U.S. Pat. No. 8,016,862 B2

Column 19
Line 42, change "first end 24" to --first end 524--

Column 22
Line 38, change "are also be formed" to --are also formed--

Column 26
Line 46, change "anchor 700" to --anchor 702--